United States Patent
Bos et al.

(10) Patent No.: US 8,163,295 B2
(45) Date of Patent: Apr. 24, 2012

(54) OUTER MEMBRANE VESICLES AND USES THEREOF

(75) Inventors: Martine Petronella Bos, Utrecht (NL);
Jan Poolman, Rixensart (BE); Boris Tefson, Utrecht (NL); Johannes Petrus Maria Tommassen, Utrecht (NL)

(73) Assignees: GlaxoSmithKline Biologicals S.A., Rixensart (BE); University of Utrecht, Utrecht (NL)

( * ) Notice: Subject to any disclaimer, the term of this patent is extended or adjusted under 35 U.S.C. 154(b) by 0 days.

(21) Appl. No.: 13/211,977

(22) Filed: Aug. 17, 2011

(65) Prior Publication Data
US 2012/0039942 A1    Feb. 16, 2012

Related U.S. Application Data

(63) Continuation of application No. 12/611,393, filed on Nov. 3, 2009, now Pat. No. 8,029,807, which is a continuation of application No. 10/584,362, filed as application No. PCT/EP2004/014770 on Dec. 21, 2004, now Pat. No. 7,628,995.

(30) Foreign Application Priority Data

Dec. 23, 2003  (GB) .................................. 0329827.0
Jul. 22, 2004   (GB) .................................. 0416398.6

(51) Int. Cl.
*A61K 39/095*  (2006.01)
(52) U.S. Cl. .................................................. 424/249.1
(58) Field of Classification Search .................. None
See application file for complete search history.

(56) References Cited

U.S. PATENT DOCUMENTS
2004/0126389 A1    7/2004   Berthet et al.

FOREIGN PATENT DOCUMENTS
WO    2004014418 A2    2/2004

OTHER PUBLICATIONS

Bos et al; "Identification of an outer membrane protein required for the transport of lipopolysaccharide to the bacterial cell surface"; Proceedings of the National Academy of Sciences; 2004; vol. 101, No. 25; pp. 9417-9422.
Braun et al.; "Imp/OstA is required for cell envelope biogenesis in *Escherichia coli*"; Molecular Microbiology; 2002; vol. 45, No. 5; pp. 1289-1302.
Morley et al.; "Vaccine prevention of meningococcal disease, coming soon?"; Vaccine; 2001; vol. 20, Nos. 5-6; pp. 666-687.
Genevrois et al.; "The Omp85 Protein of Neisseria meningitidis is required for lipid export to the outer membrane"; EMBO Journal; 2003; vol. 22, No. 8; pp. 1780-1789.
Bowie et al.; "Deciphering the Message in Protein Sequences: Tolerance to Amino Acid Substitutions"; Science; 1990; vol. 247, No. 4948; pp. 1306-1310.
Steeghs et al.; "Meningitis bacterium is viable without endotoxin"; Nature; 1998; vol. 392, No. 6675; pp. 449-450.
Moudallal et al.; "Monoclonal antibodies as probes of the antigenic structure of tobacco mosaic virus"; EMBO Journal; 1982; vol. 1; pp. 1005-1010.
Cruse et al.; Illustrated Dictionary of Immunology, 2nd ed.; 2003; pp. 46, 166, 382.
McGuinness et al.; "Class 1 outer membrane protein of Neisseria meningitidis: epitope analysis of the antigenic diversity between strains, implications for subtype definition and molecular epidemiology"; Molecular Microbiology; 1993; vol. 7; pp. 505-514.
Greenspan et al.; "Defining epitopes: It's not as easy as it seems"; Nature Biotechnology; 1999; vol. 17; pp. 936-937.
Steeghs et al.; "Immunogenicity of Outer Membrane Proteins in a Lipopolysaccharide-Deficient Mutant of Neisseria meningitidis: Influence of Adjuvants on the Immune Response"; Infection and Immunity; 1999; vol. 67; pp. 4988-4993.

*Primary Examiner* — Nita M Minnifield
*Assistant Examiner* — Brian J Gangle
(74) *Attorney, Agent, or Firm* — Kathryn L. Coulter

(57) ABSTRACT

The present invention discloses a Gram negative bacterium in which the expression of a protein involved in LPS transport to the outer membrane is functionally down-regulated such that the level of LPS in the outer membrane is decreased compared to a wild-type Gram negative bacterium. Down regulation of Imp and MsbA proteins can result in such a bacterium. Outer membrane vesicle preparations derived from the Gram negative bacterium of the invention can be used in vaccines to provide protection against bacterial infection.

2 Claims, 16 Drawing Sheets

```
Imp/OstA - SEQ ID No 1
Predicted extracellular loops are indicated in bold

LARLFSLKPLVLALGLCFGTHCAAADAVAAEETDNPTAGESVRSVSEPIQPTSLSLGSTC   60
LFCSNESGSPERTEAAVQGSGEASIPEDYTRIVADRMEGQSQVQVRAEGNVVVERNRTTL  120
NTDWADYDQSGDTVTAGDRFALQQDGTLIRGETLTYNLEQQTGEAHNVRMEIEQGGRRLQ  180
SVSRTAEMLGEGHYKLTETQFNTCSAGDAGWYVKAASVEADREKGIGVAKHAAFVFGGVP  240
IFYTPWADFPLDGNRKSGLLVPSLSAGSDGVSLSVPYYFNLAPNLDATFAPSVIGERGAV  300
FDGQVRYLRPDYAGQSDLTWLPHDKKSGRNNRYQAKWQHRHDISDTLQAGVDFNQVSDSG  360
YYRDFYGNKEIAGNVNLNRRVWLDYGGRAAGGSLNAGLSVLKYQTLANQSGYKDKPYALM  420
PRLSVEWRKNTGRAQIGVSAQFTRFSHDSRQDGSRLVVYPDIKWDFSNSWGYVRPKLGLH  480
ATYYSLNRFGSQEARRVSRTLPIVNIDSGATFERNTRMFGGEVLQTLEPRLFYNYIPAKS  540
QNDLPNFDSSESSFGYGQLFRENLYYGNDRINTANSLSAAVQSRILDGATGEERFRAGIG  600
QKFYFKDDAVMLDGSVGKKPRNRSDWVAFASGSIGSRFILDSSIHYNQNDKRAENYAVGA  660
SYRPAQGKVLNARYKYGRNEKIYLKSDGSYFYDKLSQLDLSAQWPLTRNLSAVVRYNYGF  720
EAKKPIEVLAGAEYKSSCGCWGAGVYAQRYVTGENTYKNAVFFSLQLKDLSSVGRNPADR  780
MDVAVPGYITAHSLSAGRNKRP                                       802 loop 1: 252-271
loop 2: 295-332
loop 3: 357-416
loop 4: 444-455
loop 5: 482-501
loop 6: 537-576
loop 7: 606-624
loop 8: 648-697
loop 9: 721-740
```

FIG. 7

```
Imp-FAM18   LARLFSLKPLVLALGFCFGTHCAAADAVAAEETDNPTAGGSVRSVSEPIQPTSLSLGSTC  60
NMB0280     LARLFSLKPLVLALGLCFGTHCAAADAVAAEETDNPTAGESVRSVSEPIQPTSLSLGSTC  60
NMA2207     MARLFSLKPLVLALGFCFGTHCAAADAVAAEETDNPTAGGSVRSVSEPIQPTSLSLGSTC  60
            :*************:***************************.*****************

Imp-FAM18   LFCSNESGSPERTEAAVRGSGEASIPEDYTRIVADKVEGQSQVQVRAEGNVVVERNRTTL  120
NMB0280     LFCSNESGSPERTEAAVQGSGEASIPEDYTRIVADRMEGQSQVQVRAEGNVVVERNRTTL  120
NMA2207     LFCSNESGSPERTEAAVQGSGEASIPEDYTRIVADRMEGQSQVQVRAEGNVVVERNRTTL  120
            *****************:*****************:;***********************

Imp-FAM18   NTDWADYDQSGDTVTAGDRFALQQDGTLIRGETLTYNLEQQTGEAHNVRMETEHGGRRLQ  180
NMB0280     NTDWADYDQSGDTVTAGDRFALQQDGTLIRGETLTYNLEQQTGEAHNVRMEIEQGGRRLQ  180
NMA2207     NADWADYDQSGDTVTAGDRFALQQDGTLIRGETLTYNLEQQTGEAHNVRMETEHGGRRLQ  180
            *:************************************************ *:*****

Imp-FAM18   SVSRTAEMLGEGHYKLTETQFNTCSAGDAGWYVKAASVEADREKGIGVAKHAAFVFGGVP  240
NMB0280     SVSRTAEMLGEGHYKLTETQFNTCSAGDAGWYVKAASVEADREKGIGVAKHAAFVFGGVP  240
NMA2207     SVSRTAEMLGEGHYKLTETQFNTCSAGDAGWYVKAASVEADREKGIGVAKHAAFVFGGVP  240
            ************************************************************

Imp-FAM18   IFYTPWADFPLDGNRKSGLLVPSLSAGSDGVSLSVPYYFNLAPNLDATFAPSVIGERGAV  300
NMB0280     IFYTPWADFPLDGNRKSGLLVPSLSAGSDGVSLSVPYYFNLAPNLDATFAPSVIGERGAV  300
NMA2207     IFYTPWADFPLDGNRKSGLLVPSLSAGSDGVSLSVPYYFNLAPNLDATFAPGVIGERGAV  300
            **************************************************.*******

Imp-FAM18   FDGQVRYLRPDYAGQSDLTWLPHDKKSGRNNRYQAKWQHRHDISDTLQAGVDFNQVSDSG  360
NMB0280     FDGQVRYLRPDYAGQSDLTWLPHDKKSGRNNRYQAKWQHRHDISDTLQAGVDFNQVSDSG  360
NMA2207     FDGQVRYLRPDYAGQSDLTWLPHDKKSGRNNRYQAKWQHRHDISDTLQAGVDFNQVSDSG  360
            ************************************************************

Imp-FAM18   YYRDFYGNKEIAGNVNLNRRVWLDYGGRAAGGSLNAGLSVLKYQTLANQSGYKDKPYALM  420
NMB0280     YYRDFYGNKEIAGNVNLNRRVWLDYGGRAAGGSLNAGLSVLKYQTLANQSGYKDKPYALM  420
NMA2207     YYRDFYGNKEIAGNVNLNRRVWLDYGGRAAGGSLNAGLSVLKYQTLANQSGYKDKPYALM  420
            ************************************************************

Imp-FAM18   PRLSADWRKNTGRAQIGVSAQFTRFSHDSRQDGSRLVVYPDIKWDFSNSWGYVRPKLGLH  480
NMB0280     PRLSVEWRKNTGRAQIGVSAQFTRFSHDSRQDGSRLVVYPDIKWDFSNSWGYVRPKLGLH  480
NMA2207     PRLSADWRKNTGRAQIGVSAQFTRFSHDSRQDGSRLVVYPDIKWDFSNSWGYVRPKLGLH  480
            ****.:******************************************************

Imp-FAM18   ATYYSLNRFGSQEARRVSRTLPIVNIDSGATFERNTRMFGGGVLQTLEPRLFYNYIPAKS  540
NMB0280     ATYYSLNRFGSQEARRVSRTLPIVNIDSGATFERNTRMFGGEVLQTLEPRLFYNYIPAKS  540
NMA2207     ATYYSLNRFGSQEARRVSRTLPIVNIDSGMTFERNTRMFGGGVLQTLEPRLFYNYIPAKS  540
            *****************************.**********.******************

Imp-FAM18   QNDLPNFDSSESSFGYGQLFRENLYYGNDRINTANSLSAAVQSRILDGATGEERFRAGIG  600
NMB0280     QNDLPNFDSSESSFGYGQLFRENLYYGNDRINTANSLSAAVQSRILDGATGEERFRAGIG  600
NMA2207     QNDLPNFDSSESSFGYGQLFRENLYYGNDRINTANSLSAAVQSRILDGATGEERFRAGIG  600
            ************************************************************

Imp-FAM18   QKFYFKDDAVMLDGSVGKKPRNRSDWVAFASGSIGSRFILDSSIHYNQNDKRAENYAVGA  660
NMB0280     QKFYFKDDAVMLDGSVGKKPRNRSDWVAFASGSIGSRFILDSSIHYNQNDKRAENYAVGA  660
NMA2207     QKFYFKNDAVMLDGSVGKKPRSRSDWVAFASSGIGSRFILDSSIHYNQNDKRAENYAVGA  660
            ******:**************.********:.*****************************

Imp-FAM18   SYRPAQGKVLNARYKYGRNEKIYLKSDGSYFYDKLSQLDLSAQWPLTRNLSAVVRYNYGF  720
NMB0280     SYRPAQGKVLNARYKYGRNEKIYLKSDGSYFYDKLSQLDLSAQWPLTRNLSAVVRYNYGF  720
NMA2207     SYRPAQGKVLNARYKYGRNEKIYLKSDGSYFYDKLSQLDLSAQWPLTRNLSAVVRYNYGF  720
            ************************************************************

Imp-FAM18   EAKKPIEMLAGAEYKSSCGCWGAGVYAQRYVTGENTYKNAVFFSLQLKDLSSVGRNPADR  780
NMB0280     EAKKPIEVLAGAEYKSSCGCWGAGVYAQRYVTGENTYKNAVFFSLQLKDLSSVGRNPADR  780
NMA2207     EAKKPIEVLAGAEYKSSCGCWGAGVYAQRYVTGENTYKNAVFFSLQLKDLSSVGRNPADR  780
            *******:****************************************************

Imp-FAM18   MDVAVPGYIPAHSLSAGRNKRP  802   (SEQ ID NO: 27)
NMB0280     MDVAVPGYITAHSLSAGRNKRP  802   (SEQ ID NO: 28)
NMA2207     MDVAVPGYIPAHSLSAGRNKRP  802   (SEQ ID NO: 29)
            *********.************
```

FIG. 8

A (SEQ ID NO: 2)

MIEKLTFGLFKKEDARSFMRLMAYVRPYKIRIVAALIAIFGVAATESYLAAFIAPLINHG
FSAPAAPPELSAAAGIISTLQNWREQFTYMVWGTENKIWTVPLFLIILVVIRGICRFTST
YLMTWVSVMTISKIRKDMFAKMLTLSSRYHQETPSGTVLMNMLNLTEQSVSNASDIFTVL
TRDTMIVTGLTIVLLYLNWQLSLIVVLMFPLLSLLSRYYRDRLKHVISDSQKSIGTMNNV
IAETHQGHRVVKLFNGQAQAANRFDAVNRTIVRLSKKITQATAAHSPFSELIASIALAVV
IFIALWQSQNGYTTIGEFMAFIVAMLQMYAPIKSLANISIPMQTMFLAADGVCAFLDTPP
EQDKGTLAPQRVEGRISFRNVDVEYRSDGIKALDNFNLDIRQGERVALVGRSGSGKSTVV
NLLPRFVEPSAGNICIDGIDIADIKLDCLRAQFALVSQDVFLFDDTLFENVRYSRPDAGE
AEVLFALQTANLQSLIDSSPLGLHQPIGSNGSNLSGGQRQRVAIARAILKDAPILLLDEA
TSALDNESERLVQQALERLMENRTGIIVAHRLTTIEGADRIIVMDDGKIIEQGTHEQLMS
QNGYYTMLRNISNKDAAVRTA

B (SEQ ID NO: 4)
MLAWRPGRPDGCQAAGGRRYNPGHDCIKASVSLNSAARNAPAGSQPVKAELWKRVYSRVGSYWKGLVLAVLLMAG
AAATQ
PTLAVIMKPLLDDGFSGAKPHYVWFLPLAVVGLILLRGICNPFSDYLLAWVANNVLRGIRGEMFERLLGLPDADF
KRGDT
GRLLNRFTIDAGNVTGYATDVITVLVRETLVVIALIGVLLYMSWALTLIILVMLPVSVGIARAFTRRLRRINRET
VNMNA
ELTRVVSEGIDGQRVIKLFDGYDAERRRFDFVNSRLRRFAMRSATADAALTPLTQVCISVAVGAVIAVALSQANS
GALTV
GSFASFMAALAQIFDPIKRLTNLAGKMQKMLVAAESVPTLVDQTPEADAGTRALPEPVRGKVEFRAVSHRFPDAD
RDTVS
AVSFLVEPGQTVALVGRSGSGKTTLVNMLPRFVLPDGGDILFDDVPIQDLTLRSLRSHLSLVSQDVVLFDDTIAA
NVGYG
AGGTVDDARVRDALAAANLLEFVDGLPLGIHTPVGQNAARLSGGQRQRLAIARALIKNAPVLILDEATSALDNES
ERQVQ
ASLERLMRGRTTLVIAHRLSTVQNADRIIVLDAGKIVEHGPHSELLAANGLYASLYNMQFRED

FIG. 14

(SEQ ID NO: 3)

```
atgatagaaaaactgactttcggactgtttaaaaaagaagacgcgcgcagctttatgcgc
ctgatggcgtacgtccgcccctacaaaatccgcatcgttgccgccctgattgccattttc
ggcgttgccgccaccgaaagctaccttgccgccttcatcgccccctgattaaccacggc
ttttccgcacctgccgcgccgcccgagctgtctgccgccgccggcatcatttccaccctg
caaaactggcgcgaacagtttacctatatggtttgggggacggaaaacaaaatctggacc
gtcccgctcttcctcatcatcctcgtcgtcatccgtggcatctgccgctttaccagcacc
tatctgatgacttgggtctccgtgatgaccatcagcaaaatccgcaaagatatgtttgcc
aaaatgctgacccttcctcccgctaccatcaggaaacgccgtccggcaccgtactgatg
aatatgctcaacctgaccgaacagtcggtcagcaacgccagcgacatcttcaccgtcctc
acgcgcgacacgatgatcgttaccggcctgaccatcgtcctgctttacctcaactggcag
ctcagcctcatcgtcgtcctgatgttcccctgctctccctgctctcgcgctactaccgc
gaccgtctgaaacacgtcatttccgactcgcaaaaagcataggcacgatgaacaacgtg
attgccgaaacccatcagggacaccgcgtcgtcaagctgttcaacggggcaggcgcaggcg
gcaaaccggttcgacgcggtcaaccgcaccatcgtccgcctcagcaaaaaaatcacgcag
gcaacggcggcacattccccgttcagcgaactgatcgcctcgatcgccctcgccgtcgtc
atcttcatcgccctgtggcaaagccaaaacggctacaccaccatcggcgaatttatggca
ttcatcgtcgcgatgctgcaaatgtacgccccatcaaaagccttgccaacatcagcatc
cctatgcagacgatgttcctcgccgccgacggtgtatgtgcatttctcgacaccccgccc
gaacaggacaagggcacgctcgcaccgcagcgtgtcgaagggcgcatcagcttccgcaac
gtcgatgtcgaataccgttcagacggcatcaaagccctcgacaacttcaacctcgacatc
agacaaggcgaacgcgtcgccctggtcggacgttccggcagcggcaaatccaccgtcgtc
aacctgctgccccgctttgtcgaaccgtctgccggcaacatctgcatagacggtatcgac
atcgccgacatcaaactcgactgcctgcgcgcccaattcgccctcgtctcccaagacgta
ttcctgtttgacgacaccctgtttgaaaacgtccgatacagccgtcccgacgcgggcgaa
gccgaagtcctgttcgccctccaaaccgccaacctgcaaagcctgattgacagctccccg
ctcggactgcaccagcccatcggatcgaacggcagcaacttatccggcggacagcggcaa
cgcgtcgccattgcccgcgccattgaaagacgcgccgatattattggacgaagcc
accagcgcattagacaacgaatccgaacgcctcgtccaacaggcgctcgaacgcctgatg
gaaaaccgcaccggcatcatcgtcgcccaccgcctgaccaccatcgaagggccgaccgc
atcatcgtgatggacgacggcaaaatcatcgaacaaggcacacacgaacaactgatgtcc
caaaacggttactacacgatgttacgcaatatctcaaacaaagatgccgccgtccggacg
gcataa
```

FIG. 15A (SEQ ID NO: 5)

```
atgctggcgtggcggccgggtcggccggacggttgtcaggcggcgggtggccgacggtacaatcccgggcacgat
gtat
taaagcgagtgtttccttgaattctgccgcacgcaatgcgcccgccggctcccagccggtcaaggccgaactctg
gaagc
gggtctacagccgcgtaggctcttactggaaggggctggtgctggccgtcctgctgatggccggcgccgccgcga
cccag
cccacgctggcagtcatcatgaagccgctgctcgacgatggcttctcgggcgccaagccgcattatgtctggttc
ctgcc
gctggcggtggtggggctgatcctgctgcgcggaatctgcaatttcttcagcgactacctgctggcctgggtggc
caaca
acgtgctgcgcggcatccggggcgagatgttcgagcggctgctgggcctgcccgatgccgacttcaagcgcggcg
acacc
ggccgcctgctcaaccgcttcaccatcgacgcgggcaacgtcaccggctacgccaccgacgtcatcacggtgctg
gtgcg
cgaaaccctggtcgtcatcgccctgatcggcgtgctgctgtacatgtcgtgggcgctgacgctgatcatcctcgt
catgc
tgccggtgtcggtgggcatcgcccgcgccttcacgcgccggctgcgccgcatcaaccgcgaaaccgtcaacatga
acgcc
gagctcacccgcgtggtcagcgagggcatcgacgggcagcgtgtcatcaagctgttcgacggctatgacgccgag
cgccg
ccgtttcgacttcgtcaactcgcgcctgcgccgcttcgcgatgcgcagcgccaccgccgacgcggcgctcacgcc
gctca
cgcaggtgtgcatctcggtcgccgtgggcgcggtcatcgccgtggccctcagccaggccaacagcggcgcgctca
ccgtc
ggcagcttcgcctcgttcatggccgcgctggcgcagatcttcgatccgatcaagcgcctgaccaacctggccggc
aaaat
gcagaaaatgctggtggccgccgaaagcgtgttcaccctggtggaccagacgcccgaggccgacgccggcacgcg
cgcct
tgcccgaaccggtgcgcggcaaggtcgaattccgtgcggtcagccatcgcttcccggacgccgatcgcgataccg
tcagc
gccgtgtcgttcctggtcgagccgggccagaccgtggccctggtcggacgctcgggcagcggcaagaccactctg
gtcaa
catgctgccgcgctttgtcctgcccgatggcggcgacatcctgttcgacgatgtgcccatccaggatctcacctt
gcgca
gcctgcgctcgcatctgtcgctggtcagccaggacgtggtgctgttcgacgacaccattgccgccaacgtgggtt
atggc
gccggcggcaccgtcgacgacgcgcgcgttcgcgacgcgctggccgcggccaacctgctggagttcgtcgacggc
ttgcc
gctgggcatccacacgccggtgggccagaatgccgcccgcctgtcgggcggccagcgccagcgcctggcgatcgc
ccgcg
ccctgatcaagaacgcgccggtcctgatcctcgacgaggcgacctcggcgctggacaacgaatccgagcgccagg
tgcag
gcatcgctggagcggctgatgcgcgggcgcaccacgctggtcatcgcccaccggctgtccaccgtgcagaacgcc
gaccg
catcatcgtgctggacgccggcaagatcgtcgagcacgggccgcacagcgagctgttggccgccaacggcctgta
cgcct
cgctctacaacatgcagttccgcgaggactga
```

FIG. 15B

OUTER MEMBRANE VESICLES AND USES THEREOF

CROSS-REFERENCE TO RELATED APPLICATIONS

This application is a Continuation of U.S. application Ser. No. 12/611,393 filed Nov. 3, 2009, now allowed; which is a Continuation of U.S. application Ser. No. 10/584,362 filed Jun. 23, 2006, issued U.S. Pat. No. 7,628,995; which was filed pursuant to 35 U.S.C. §371 as a U.S. National Phase Application of International Patent Application No. PCT/EP2004/014770 filed Dec. 21, 2004, which claims priority from GB Application No. 0416398.6 filed Jul. 22, 2004 and GB Application No. 0329827.0 filed Dec. 23, 2003.

BRIEF DESCRIPTION OF THE INVENTION

The present invention relates to Gram negative bacteria in which the expression of a protein involved in the transport of lipopolysaccharide (LPS) to the outer membrane of the bacterium is functionally downregulated. Examples of such proteins are the Imp and MsbA proteins. The invention also relates to Neisserial strains containing mutated imp and/or msbA genes which exhibit disruption in lipopolysaccharide (LPS) transport to the outer membrane and/or contain a lower amount of LPS. A further aspect of the invention relates to outer membrane vesicle preparations made from such strains. The present invention includes mutated Imp proteins and particularly chimeric Imp proteins. The invention also relates to vaccines and immunogenic compositions containing mutated Imp proteins or whole bacteria or fractions of bacteria with disruption of transport of LPS to the outer membrane and their use in the treatment or prevention of Neisserial infection.

BACKGROUND

Gram negative bacteria are the causative agents for a number of human pathologies and there is a need for effective vaccines to be developed against many of these bacteria. In particular *Bordetella pertussis*, *Borrelia burgdorferi*, *Brucella melitensis*, *Brucella ovis*, *Chlamydia psittaci*, *Chlamydia trachomatis*, *Esherichia coli*, *Haemophilus influenzae*, *Legionella pneumophila*, *Neisseria gonorrhoeae*, *Neisseria meningitidis*, *Pseudomonas aeruginosa* and *Yersinia enterocolitica* are Gram negative bacteria which cause pathologies which could be treated by vaccination.

*Neisseria meningitidis* is an important pathogen, particularly in children and young adults. Septicemia and meningitis are the most life-threatening forms of invasive meningococcal disease (IMD). This disease has become a worldwide health problem because of its high morbidity and mortality.

Thirteen *N. meningitidis* serogroups have been identified based on antigenic differences in the capsular polysaccharides, the most common being A, B and C which are responsible for 90% of disease worldwide. Serogroup B is the most common cause of meningococcal disease in Europe, USA and several countries in Latin America.

Vaccines based on the capsular polysaccharide of serogroups A, C, W and Y have been developed and have been shown to control outbreaks of meningococcal disease (Peltola et al 1985 Pediatrics 76; 91-96). However serogroup B is poorly immunogenic and induces only a transient antibody response of a predominantly IgM isotype (Ala'Aldeen D and Cartwright K 1996, J. Infect. 33; 153-157). There is therefore no broadly effective vaccine currently available against the serogroup B meningococcus which is responsible for the majority of disease in most temperate countries. This is particularly problematic since the incidence of serotype B disease is increasing in Europe, Australia and America, mostly in children under 5. The development of a vaccine against serogroup B meningococcus presents particular difficulties because the polysaccharide capsule is poorly immunogenic owing to its immunologic similarity to human neural cell adhesion molecule. Strategies for vaccine production have therefore concentrated on the surface exposed structures of the meningococcal outer membrane but have been hampered by the marked variation in these antigens among strains.

Further developments have led to the introduction of vaccines made up of outer membrane vesicles which will contain a number of proteins that make up the normal content of the bacterial membrane. One of these is the VA-MENGOC-BC® Cuban vaccine against *N. meningitidis* serogroups B and C (Rodriguez et al 1999 Mem Inst. Oswaldo Cruz, R10 de Janeiro 94; 433-440). This vaccine was designed to combat an invasive meningococcal disease outbreak in Cuba which had not been eliminated by a vaccination programme using a capsular polysaccharide AC vaccine. The prevailing serogroups were B and C and the VA-MENGOC-BC® vaccine was successful at controlling the outbreak with an estimated vaccine efficiency of 83% against serogroup B strains of *N. meningitidis* (Sierra et al 1990 In *Neisseria*, Walter Gruyter, Berlin, m. Atchman et al (eds) p 129-134, Sierra et al 1991, NIPH Ann 14; 195-210). This vaccine was effective against a specific outbreak, however the immune response elicited would not protect against other strains of *N. meningitidis*.

Subsequent efficacy studies conducted in Latin America during epidemics caused by homologous and heterologous serogroup B meningococcal strains have shown some efficacy in older children and adults but its effectiveness was significantly lower in younger children who are at greatest risk of infection (Milagres et al 1994, Infect. Immun. 62; 4419-4424). It is questionable how effective such a vaccine would be in countries with multistrain endemic disease such as the UK. Studies of immunogenicity against heterologous strains have demonstrated only limited cross-reactive serum bactericidal activity, especially in infants (Tappero et al 1999, JAMA 281; 1520-1527).

A second outer membrane vesicle vaccine was developed in Norway using a serotype β isolate typical of those prevalent in Scandinavia (Fredriksen et al 1991, NIPH Ann, 14; 67-80). This vaccine was tested in clinical trials and found to have a protective efficacy after 29 months of 57% (Bjune et al 1991, Lancet, 338; 1093-1096).

However, the use of outer membrane vesicles in vaccines is associated with some problems. For instance, the OMV contain toxic lipopolysaccharides (LPS). The toxicity of outer membrane vesicles may be decreased by treatment with detergents to remove the majority of LPS in order to prevent toxic reactions in vaccinees. This procedure unfortunately also removes other potentially important vaccine components such as surface exposed lipoproteins.

The imp gene encodes the Imp/OstA protein which is an outer membrane protein of Gram negative bacteria. Imp/OstA has been most extensively studied in *E. coli* where it was first described as having a role in outer membrane permeability (Sampson et al 1989 Genetics 122, 491-501). Imp/OstA was subsequently found to determine organic solvent tolerance in *E. coli* (Aono et al 1994 Appl. Environ. Microbiol. 60, 4624-4626). It has been proposed that Imp/OstA contributes to n-hexane resistance of *E. coli* by reducing the influx of n-hexane (Abe et al 2003, Microbiology 149, 1265-1273).

The msbA gene was first identified in *E. coli* as a multi-copy-suppressor of the mutation in the htrB (lpxL) gene, which encodes an enzyme involved in a late step of lipid A biosynthesis (Karow and Georgeopoulos, 1993. Mol. Microbiol. 7, 69-79). The MsbA protein belongs to a family of ABC (ATP-binding cassette) transporters. A temperature-sensitive msbA mutant of *E. coli* has been reported to accumulate LPS as well as three major PL in the inner membrane when shifted to the restrictive growth temperature (Doerrler, et al 2001 J. Biol. Chem. 276, 11461-11464). This result indicated a role for MsbA in the translocation of both LPS and PL across the inner membrane and/or, as proposed earlier (Polissi and Georgopoulos, 1996 Mol. Microbiol. 20, 1221-1233), in a later step of the transport process.

There is a need for improved vaccines for use in treatment and prevention of Gram negative bacterial infection, particularly Neisserial infection. It is particularly important to address the problem of LPS toxicity in vaccines comprising whole bacteria, or outer membrane vesicle preparations whilst ensuring that desirable antigens are retained in the outer membrane. The present application discloses the general concept of outer membrane vesicle vaccines prepared from Gram negative bacterial mutant strains, particularly Neisserial strains such as *N. meningitidis*, which have reduced LPS compared to wild type strains, or no LPS on its surface. Such vaccines have the advantage that the outer membrane vesicles may be produced using a protocol involving extraction with low or no detergent thus retaining protective antigens such as lipoproteins on the outer membrane vesicle surface. It is particularly preferred if a low level (less than 50, 40, 30, or 10% of wild-type level) of LPS is maintained in the mutant strain so that one or both of the following advantages are realised: i) the LPS can still be used as an antigen in its own right, and ii) the strain may grow better for production purposes. The inventors have found that disruption of either the Imp or MsbA proteins can produce such strains and outer membrane vesicle vaccines. A particularly preferred mutant for these purposes is a functional disruption of the imp gene.

The present invention further provides a mutated Imp or MsbA protein, for example a chimeric protein comprising a backbone polypeptide which is derived from an Imp protein and at least one insert region derived from a different protein wherein part or all of at least one Imp extracellular loop is replaced with one or more polypeptide sequence from at least one additional protein. Also provided are vaccine components comprising a chimera of part or all of at least one Imp extracellular loop with a different carrier protein which provides T-helper epitopes.

The present application discloses proteins that regulate the transport of LPS to the outer membrane of Gram negative bacteria. In particular, a function has been provided for Imp in regulating the transport of LPS to the outer membrane of Gram negative bacteria. It further discloses that MsbA regulates the transport of LPS to the outer membrane of *Neisseria* and the disruption of this protein does not lead to a disruption of phospholipid transport to the outer membrane. Downregulation of Imp or MsbA, either by downregulation of expression of the imp or msbA gene or by disrupting the structure of the Imp or MsbA protein so that it no longer transports LPS to the outer membrane, leads to most (but not all) of the LPS failing to reach the cell surface as shown in FIGS. 5 and 10. Downregulation of Imp MsbA also leads to a decrease in the amount of LPS present in the bacteria due to feedback inhibition on LPS synthesis by mislocalised LPS. Downregulation of Imp or MsbA therefore produces a Gram negative bacterium (preferably a Neisserial bacterium) with a low level of LPS, equivalent or lower to the level achieved after detergent treatment. Such a bacterium has lower toxicity whilst retaining sufficient LPS to enable the LPS to contribute to the immunogenicity of the bacterium/vaccine composition.

A further advantageous aspect of some embodiments of the invention is that the Imp protein is used as a scaffold to display advantageous heterologous antigens on the outer membrane of Gram negative bacteria, preferably a Neisserial strain, more preferably *N. meningitidis*. These antigens are positioned at the site of one of the Imp extracellular (surface exposed) loops.

A further advantage of some embodiments of the invention is realised when at least some of the extracellular loops of Imp are retained in the chimeric protein of the invention. The amino acid sequence of the extracellular loops are well conserved and antibodies against an extracellular loop of Imp should crossreact with a wide range of bacterial, preferably Neisserial strains.

In a preferred embodiment, the invention provides a Gram negative bacterium in which a protein involved in the transport of LPS to the outer membrane, for instance Imp or MsbA, is down regulated such that LPS transport to the outer membrane is disrupted.

In a further embodiment, the invention provides a polynucleotide comprising a sequence encoding the mutated or chimeric protein of the invention, an expression vector comprising a sequence encoding the chimeric protein of the invention and a host cell comprising said expression vector. Polynucleotides of the invention do not encompass a bacterial genome.

In a further embodiment, the invention provides an outer membrane vesicle preparation, from a strain in which the expression of a protein regulating LPS transport to the outer membrane, for instance Imp or MsbA, is downregulated such that the outer membrane vesicle has a lower LPS content than outer membrane vesicles derived from a similar strain of Gram negative bacterium in which transport of LPS to the outer membrane has not been disrupted.

In a further embodiment, the invention provides a method for producing the chimeric protein or outer membrane vesicle preparation of the invention.

In a further embodiment, the invention provides a pharmaceutical preparation, preferably a vaccine comprising the Gram negative (preferably Neisserial) bacterium of the invention or a fraction or membrane thereof, the chimeric protein of the invention, or the outer membrane vesicle preparation of the invention, and a pharmaceutically acceptable carrier.

In a further embodiment, the invention provides methods of treatment or prevention of Gram negative bacterial infection, preferably Neisserial infection.

DESCRIPTION OF DRAWINGS

FIG. 7. Sequence of Imp (SEQ ID NO. 1) showing position of the nine extracellular loops.

FIG. 8. Alignment of meningococcal Imp sequences.

The kanamycin-resistance cassette (KAN) replaces msbA in the mutant, leaving only 131 bp at the 3' end (M). Primers used for the disruption procedure and cloning of msbA are indicated with arrows. Primer sequences are (A) CCCAAAGCGAAGTGGTCGAA (SEQ ID NO: 6); (B) GTCGACTATCGGTAGGGCGGGAACTG (AccI restriction site is underlined) (SEQ ID NO:7); (C) GTCGACGAC-CGCATCATCGTGATGGA (AccI restriction site is underlined) (SEQ ID NO: 8); (D) TTCGTCGCTGCCGACCTGTT (SEQ ID NO: 9); (E) TTCATATGATAGAAAAACT-GACTTTCGG (NdeI restriction site is underlined) (SEQ ID NO: 10); (F) GACGTCCCATTTCGGACGGCATTTTGT (AatII restriction site is underlined) (SEQ ID NO: 11). Predicted promoter (P) and terminator (T) sequences are indicated. ORFs indicated with NMB1918 and NMB1920 putatively code for a malonyl CoA-acyl carrier protein transacylase and GMP synthase, respectively.

Figure 10:
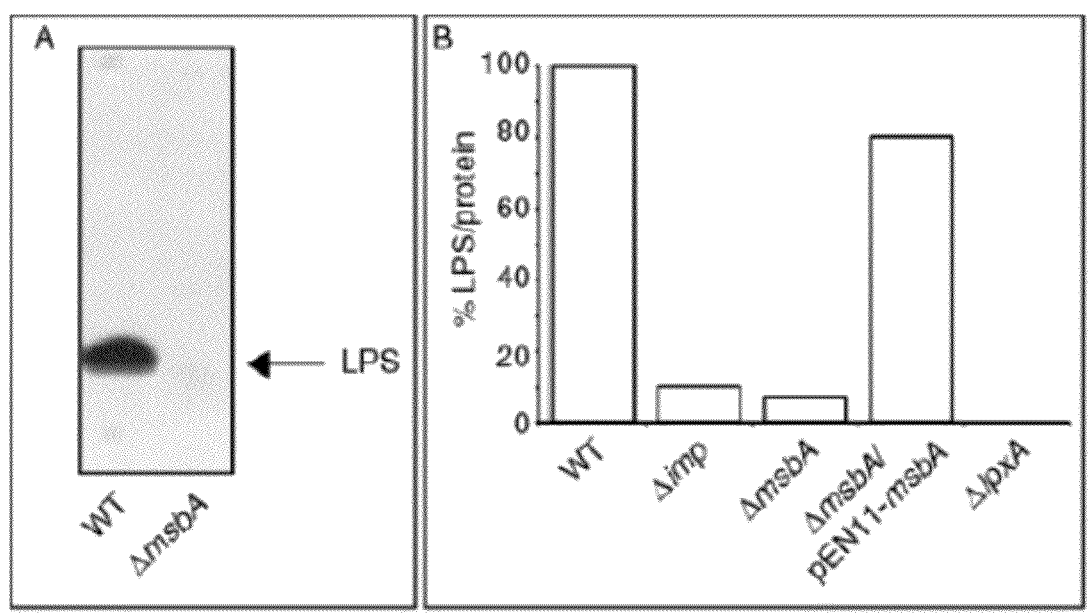

FIG. 10. LPS content in the msbA mutant.

A. Cells from strain HB-1 (WT) and its msbA-mutant derivative (AmsbA) were resuspended from plate and the LPS content was analyzed by Tricine-SDS-PAGE.

B. KDO and protein concentrations were measured from cell envelopes isolated from different strains derived from H44/76. The KDO concentrations measured were corrected for the background value measured in the lpxA mutant, and the ratio of the LPS and protein concentration in the wild-type strain was set to 100%.

Figure 11:
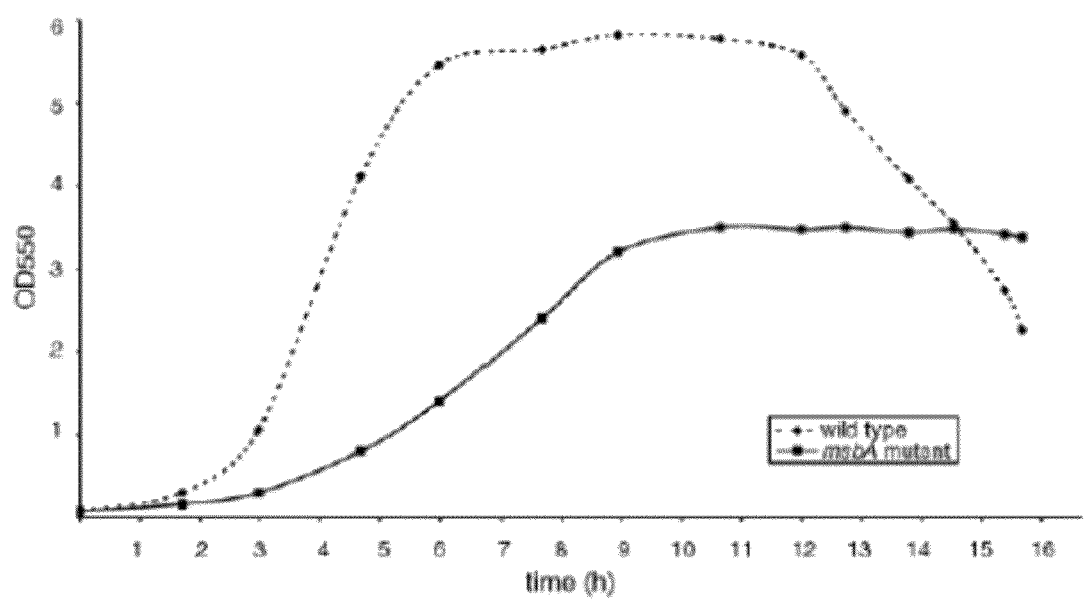

FIG. 11. Growth of the msbA mutant. Strain HB-1 (wild type) and its msbA-mutant derivative were grown on plate overnight and resuspended in 5 ml of TSB. The $OD_{550}$ was measured in time during incubation at 37° C. while shaking at 180 rpm.

Figure 12:
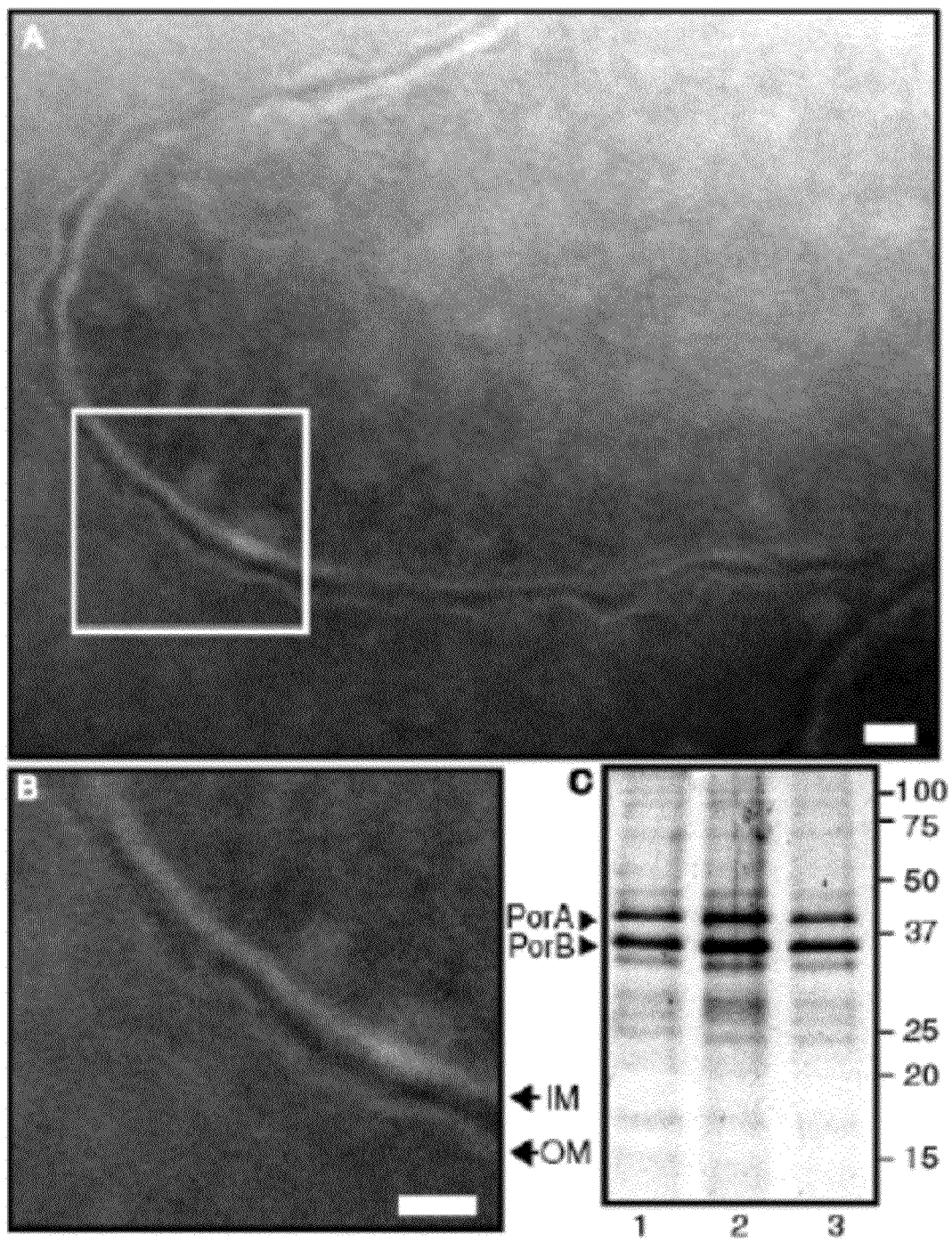

FIG. 12. Morphology and cell envelope protein profile of the msbA mutant.

A. Electron micrograph of an ultrathin section of the msbA mutant derived from H44/76. The area inside the white rectangle is shown at a higher magnification in panel B. The inner (IM) and outer membrane (OM) are indicated with arrows. Scale bars are 100 nm. C. Cell envelope protein profiles of wild-type strain H44/76 (lane 1), its msbA mutant derivative (lane 2) and the msbA mutant complemented with pEN11-msbA (lane 3). PorA and PorB are indicated at the left.

Figure 13:
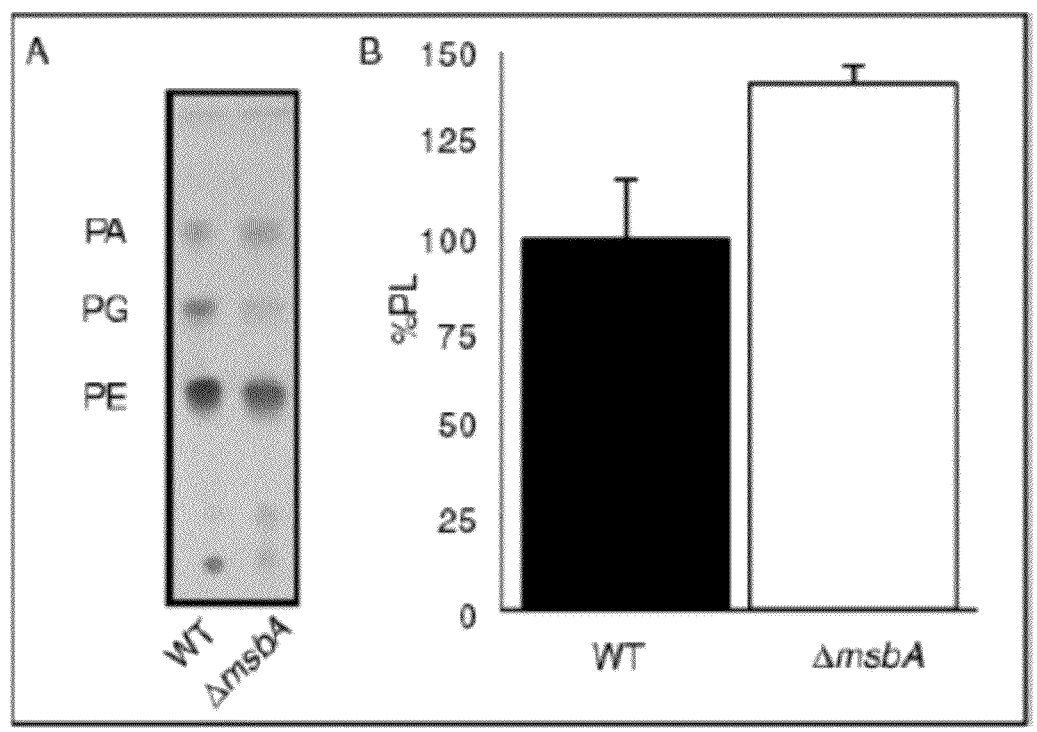

FIG. 13. Phospholipids analysis of wild-type and msbA-mutant strain.

A. Cells from strain HB-1 (WT) and its msbA-mutant derivative (.msbA) were labeled with [14C]acetate, and their phospholipids were isolated and analyzed by TLC. The positions of the major PL species are indicated.

B. Cells grown on plate were resuspended, and, based upon the OD550, equal amounts of cells were used for PL isolation. The PL were quantified for their phosphorus content. Wild-type amounts were set at 100% and compared with amounts isolated from the msbA mutant. Mean values are derived from 6 independent experiments.

FIG. 14. A—Amino Acid sequence of MsbA from *N. meningitidis* (SEQ ID NO:2).

B—Amino Acid sequence of MsbA from *B. parapertussis* (SEQ ID NO:4).

FIG. 15. A—Nucleic acid sequence of MsbA from *N. meningitidis* (SEQ ID NO:3).

B—Nucleic acid sequence of MsbA from *B. pertussis* (SEQ ID NO:5).

DETAILED DESCRIPTION

The terms "comprising", "comprise" and "comprises" herein are intended by the inventors to be optionally substitutable with the terms "consisting of", "consist of" and "consists of", respectively, in every instance.

The terms lipopolysaccharide (LPS) and lipooligosaccharide (LOS) are interchangeable and the correct term for the bacterial strain in question should be adopted.

Gram Negative bacterium with reduced LPS transport to the outer membrane One aspect of the invention is a Gram negative bacterium in which the expression of a protein involved in LPS transport to the outer membrane is downregulated such that the level of LPS in the outer membrane is decreased compared to a wild-type Gram negative bacterium or such that LPS transport to the outer membrane is disrupted. Examples of proteins involved in LPS transport to the outer membrane are Imp and MsbA. 1, 2, 3, 4 or 5 or more proteins involved in LPS transport to the outer membrane may be functionally down-regulated.

The wild-type Gram negative bacterium is defined as the corresponding Gram negative bacterium in which the expression of proteins involved in LPS transport to the outer membrane has not been disrupted.

Functional downregulation of the protein involved in LPS transport should not result in a lethal phenotype. For instance, in the case of MsbA downregulation, the Gram negative bacterium is preferably not a strain of *E. Coli* in which phospholipids transport is disrupted.

Imp and/or MsbA expression is downregulated by either downregulating expression from the imp and/or msbA gene or by disrupting the structure of the Imp and/or MsbA protein so that it no longer transports LPS to the outer membrane efficiently, i.e. so that the amount of LPS present in the outer membrane is reduced.

Downregulated preferably means functionally downregulated. This may be accomplished by downregulation of expression, or disruption of the gene so that no expression occurs. It may also be accomplished by altering the structure of the protein involved in transport of LPS to the outer membrane (e.g. Imp or MsbA) by deletion of amino acids, insertion of amino acids or substitution of amino acids so that the resultant protein transports LPS to the outer membrane of a Gram negative bacterium less effectively that the unmutated protein.

The functional downregulation of the protein involved in the transport of LPS to the outer membrane (e.g. Imp or MsbA) results in a decrease of the amount of LPS on the outer membrane of at least 10%, 20%, 30%, 40%, 50%, 60%, 70%, preferably 80%, 90% or 95% or 99% or 100% compared to a similar strain of Gram negative bacteria in which Imp and/or MsbA is not down regulated.

Where the level of expression of the protein involved in the transport of LPS to the outer membrane (e.g. Imp or MsbA) is disrupted, the amount of the protein involved in the transport of LPS to the outer membrane (e.g. Imp or MsbA) in the outer membrane is decreased by at least 20%, 30%, 40%, 50%, preferably 60%, 70%, 80%, 90%, 95%, 98% or 100%. Optionally the level of expression of both Imp and MsbA is disrupted.

In a preferred embodiment, the Gram negative bacterium of the invention comprises a mutated protein involved in the transport of LPS to the outer membrane (for instance, Imp and/or MsbA) in which the structure of the protein is disrupted by removing part of the sequence to form a truncated protein, or by changing the sequence so that LPS transporting activity is decreased or lost, or by deleting part of the sequence of the protein and replacing it with a sequence from a different protein to make a chimeric protein.

In a preferred embodiment, at least part of at least 1, 2, 3, 4, 5, 6, 7, 8 or 9 extracellular loops of the Imp protein are removed. The deleted sequence(s) are optionally replaced with the sequence from a different protein to make a chimeric protein. The inventors have found that Imp protein provides a very good scaffold for the display of heterologous peptide or epitopes in a useful conformation, particularly when inserted into or if replacing an Imp extracellular loop. Such Imp proteins and outer membrane vesicles containing these, form an independent aspect of the present invention.

The Gram negative bacterium of the invention preferably comprises at least one of the mutated or chimeric proteins of the invention described below.

The Gram negative bacterium is selected from any suitable strain of Gram negative bacterium. Where Imp expression is targeted, the wild-type Gram negative bacterium must express an Imp homolog (therefore for this aspect of the invention Gram negative bacteria are not from *Thermotoga maritima, Deinococcus radiodurans, Borrelia burgdorfferi* or *Treponema paffidium*). Where MsbA expression is targeted, the MsbA downregulation does not lead to a lethal phenotype, therefore for this aspect of the invention, the Gram negative bacterium is not Esherichia coli. Preferred Gram negative bacteria include *Bordetella pertussis, Moraxella catarrhalis, Brucella melitensis, Brucella ovis, Chlamydia psittaci, Chlamydia trachomatis, Esherichia coli, Haemophilus influenzae, Legionella pneumophila, Neisseria gonorrhoeae, Neisseria meningitidis, Pseudomonas aeruginosa* and *Yersinia enterocolitica*. Most preferably, the Gram negative bacterium is *Neisseria meningitidis.*

Proteins and Chimeric Proteins

A further aspect of the invention is a mutated MsbA or Imp protein in which the function of transporting LPS to the outer membrane has been disrupted. This may be achieved by deleting regions of MsbA and/or Imp to form truncated proteins or by mutating amino acids within the polypeptide sequence. A chimeric protein wherein one or more region(s) of the sequence of MsbA or Imp are exchanged for sequence from other protein(s) may also be used to disrupt the function of transporting LPS to the outer membrane.

A chimeric protein is a protein containing polypeptide sequence derived from two or more different proteins. It contains a backbone polypeptide into which sequence derived from at least one other protein is inserted or adjoined. The backbone polypeptide typically makes up the majority of the chimeric protein and in the case of the present invention, is derived from a protein involved in the transport of LPS to the outer membrane, for instance an Imp or an MsbA protein. In some embodiments of the invention, the protein involved in LPS transport to the outer membrane (e.g. Imp or MsbA) will make up a small fraction of the chimeric protein.

Where the chimeric protein of the invention is an Imp mutant, it comprises at least one part (optionally at least 2, 3, 4, 5, 6, 7, 8, 9 or 10 parts) which are derived from an Imp protein and at least one part (optionally at least 2, 3, 4, 5, 6, 7, 8, 9 or 10 parts) which are derived from at least one different protein (optionally at least 2, 3, 4, 5, 6, 7, 8, 9 or 10 different proteins).

'Derived from' indicates the origin of the protein sequence. A derived sequence encompassed both the complete protein sequence and a portion of the complete protein sequence.

Preferred embodiments of the invention include chimeric proteins in which the majority of the protein is Imp and the extracellular loops are adapted to carry peptides from other proteins, optionally by deleting at least some of the Imp extracellular loop(s). They also include chimeric proteins containing at least one extracellular loop(s) of Imp incorporated into the structure of a different protein, preferably a bacterial outer membrane protein. They also include at least one extracellular loop from Imp linked to a carrier of T-cell epitopes. The link could be a peptide bond, covalent bonds formed by a conjugation process, preferably as described below, or non-covalent interactions.

Optionally, the chimeric protein is derivable from the Gram negative bacterium of the invention.

Preferably, the Gram negative bacteria and chimeric proteins of the invention contain an Imp or MsbA polypeptide derived from any Gram negative bacterium, preferably from *Bordetella pertussis, Moraxella catarrhalis, Brucella melitensis, Brucella ovis, Chlamydia psittaci, Chlamydia trachomatis, Esherichia coli, Haemophilus influenzae, Legionella pneumophila, Neisseria gonorrhoeae, Neisseria meningitidis, Pseudomonas aeruginosa* and *Yersinia enterocolitica*, most preferably from *Neisseria meningitidis*. Most preferably, a chimeric protein of the invention contains an Imp polypeptide with a sequence sharing at least 70%, 80%, 85%, 90%, 95% or 99% identity with the corresponding sequence of SEQ ID No. 1. Most preferably, a chimeric protein of the invention contains an MsbA polypeptide with a sequence sharing at least 70%, 80%, 85%, 90%, 95% or 99% identity with the corresponding sequence of SEQ ID No. 2. Since the chimeric protein contains only part of the sequence of the Imp or MsbA protein, the degree of sequence identity is calculated on the basis of corresponding sequences. This means that the parts of the Imp or MsbA sequence deleted and/or replaced are not included in this sequence identity calculation.

Alternatively, where the Imp or MsbA polypeptide makes up at least 50% of the chimeric protein, the complete sequence of the chimeric protein shares at least 40%, 50%, 60%, preferably 70%, 75%, 80%, 85%, 90% or 95% with the sequence of SEQ ID NO. 1 or SEQ ID NO:2.

The inventors have elucidated a topology model of Imp which indicates the presence of 9 extracellular (surface-exposed) loops. At least some amino acids from at least 1, 2, 3, 4, 5, 6, 7, 8 or 9 of the surface loops of the Imp protein may be replaced by non-natural, i.e. heterologous sequence as an insert. At least some of any of the loops may be replaced with heterologous sequence, however, preferred loops to be inserted into, replaced, altered or deleted are one or more of loop 3, loop 8, loop 6 and loop 2. Preferred combination of loops to change include loop 3; loop 8; loops 3 and 8; loop 6; loops 3 and 6; loops 6 and 8; loops 3, 6 and 8; loop 2; loops 2 and 3; loops 2 and 6; loops 2 and 8; loops 2, 3 and 6; loops 2, 3 and 8; loops 2, 6 and 8; loops 2, 3, 6 and 8. The preferred combinations of loops replaced by heterologous sequence (or altered or deleted) are optionally combined with replacement (or alteration of deletion) of one or more of loops 1, 4, 5, 7 and 9. In a further preferred embodiment at least some of all 9 loops are deleted or deleted and replaced with heterologous sequence.

The size of deletion of the extracellular loop is at least 6, 10, 15, 20, 30, 40 or 50 amino acids. The deleted sequence is optionally replaced with an insert sequence of at least 6, 10, 15, 20, 30, 40, 50, 60 or 70 amino acids.

Preferred chimeric proteins contain an Imp backbone in which sequence(s) corresponding to 1, 2, 3, 4, 5, 6, 7, 8 or 9 of; amino acids 357-416, 648-697, 537-576, 295-332, 252-271, 444-455, 606-624, 482-501, or 721-740 of SEQ ID No 1 is/are absent from the backbone polypeptide. At least 6, 10, 15, 20, 30, 40 or 50 amino acids may be absent from one or more of the above sequences.

The replacement sequence or insert (if employed) is from a different protein. It can be from the same strain or a different strain of bacteria and is preferably from a bacterial outer membrane protein. It is preferred that such replacement sequences are conserved and/or surface exposed, i.e. able to generate an immune response, preferably against more than one strain of a bacterial organism. Preferably, one loop or part thereof, is replaced with an insert sequence from a single protein. Where multiple loops are replaced, they are preferably replaced with inserts from different proteins or the same protein from different strains of bacteria, preferably Neisseria.

In one embodiment the replacement sequence is derived from Neisserial outer membrane proteins, such as Neisseria gonorrhoeae or Neisseria meningitidis. An example of such a suitable outer membrane protein is given in U.S. Pat. No. 5,912,336 which describes a Neisserial iron regulated protein, designated TbpA. Replacement sequence could conveniently be derived from any one or more of loops 2, 3, 4, 5 and 8 of TbpA. These loops correspond generally to amino acids 226-309; 348-395; 438-471; 512-576 and 707-723 of TbpA respectively. Preferably one or more of loops 4, 5 and 8 are incorporated. An insert is derived from TbpA-high molecular weight and/or TbpA-low molecular weight (as described later). In a preferred embodiment, an insert of TbpA-high molecular weight replaces at least part of an Imp extracellular loop and an insert of TbpA-low molecular weight replaces at least part of a different Imp extracellular loop. Preferably the preferred loop combinations described above are replaced.

Another example of such a suitable outer membrane protein is given in WO01/55182, which describes the NhhA (or Hsf) surface antigen from Neisseria meningitidis. Replacement sequence could conveniently be derived from one or more constant regions of an NhhA protein generally designated as C1, C2, C3, C4 and C5. An example of another replacement sequence which could be used in the present invention is described in EP 0 586 266.

Further Neisserial OMP loops that may be substituted for Imp loops (particularly loops 3 and/or 8) are PorA loop 4 [or variable region 2]; PorA loop 5 (described in "Topology of outer membrane porins in pathogenic Neisseria spp", van der Ley, Poolman, etc., Infect Immun 1991, 59, 2963-71; its sequence in PorA P1.7, 16 (H44/76) loop 5 being: RHAN-VGRNAFELFLIGSGSDQAKGTDPLKNH, SEQ ID NO: 12); LbpA surface exposed loops 4, 5, 7, 10 and 12, corresponding to amino acids 210-342, 366-441, 542-600, 726-766 and 844-871, respectively, with 12 being preferred (sequence KGKNPDELAYLAGDQKRYSTKRASSSWST, SEQ ID NO: 13) [see Prinz et al. 1999 J. Bacter. 181:4417 for further details on LbpA surface loops incorporated by reference herein]; NspA surface exposed loops 1, 2, 3 or 4, corresponding to amino acid sequence 25-54, 61-87, 103-129 and 149-164, respectively, preferably where loop 2 (e.g. FAVDYTRYKNYKAPSTDFKLYSIGASA, SEQ ID NO: 14) and/or 3 (e.g. ARLSLNRASVDLGGSDSF-SQTSIGLGVL, SEQ ID NO: 15) is inserted (as these loops are quite small not all the Imp loop 2 and/or 8 would be ideally removed to introduce these loops, and if both are to be introduced, it is preferred that they are introduced on loop 2 or 8 (or vice versa) in order to try to preserve the conformational epitope that exists between loops 2 and 3 of NspA) [see Vandeputte-Rutten et al 2003 JBC 278:24825 for more details on NspA loops, incorporated by reference herein]; any of the surface exposed loops of Omp85 (see Science 2003 299:262-5, and supporting online material Fig S4, incorporated by reference herein).

Alternatively peptide mimotopes of bacterial carbohydrate antigens may be incorporated into Imp in the above way. Preferably mimotopes of Neisserial LOS are incorporated into loops 2 and/or 8 to advantageously stimulate an immune response against this important antigen without having its toxic effects in a vaccine. LOS mimotopes are well known in the art (see WO 02/28888 and references cited therein, incorporated by reference herein).

In a preferred embodiment of the invention, the chimeric protein comprises all or part of at least one extracellular loop from Imp. As shown in FIG. 7, the Imp protein is well conserved between Gram negative bacterial strains and is therefore an antigen that elicits cross-reactive antibodies which react with different strains of Gram negative bacteria, preferably Neisseria. Preferably the chimeric protein of the invention comprises at least 6, 10, 15, 20, 30, 40 or 50 amino acids of at least 1, 2, 3, 4, 5, 6, 7, 8 or 9 of the Imp extracellular loops 1, 2, 3, 4, 5, 6, 7, 8 and/or 9. Preferred combinations of Imp extracellular loops to be retained are loops 3 and 8, loops 3 and 6, loops 6 and 8, loops 3, 6 and 8 or all 9 extracellular loops.

In one embodiment of the invention, the extracellular loop(s) of Imp (preferably substantially devoid of Imp sequence not part of an extracellular loop) is covalently linked to sequence from a different protein. This may be achieved through peptide bonds linking the polypeptide sequence of at least one Imp extracellular loop to the polypeptide sequence of at least one different protein (acting as a carrier) to form a chimeric protein. Alternatively, the Imp extracellular loop(s) is conjugated to a carrier molecule, preferably a protein or a polysaccharide or oligosaccharide or lipopolysaccharide using conjugation methods as described below. The carrier is preferably a protein comprising T-cell epitopes, such as tetanus toxoid, tetanus toxoid fragment C, diphtheria toxoid, CRM197, pneumolysin, Protein D (U.S. Pat. No. 6,342,224).

It will be appreciated that the mutant proteins of the present invention may be prepared using conventional protein engineering techniques. For example, polynucleotides of the invention or coding for a wild-type Imp may be mutated using either random mutagenesis, for example using transposon mutagenesis, or site-directed mutagenesis.

It will be understood that protein sequences of the invention or for use in the invention are provided as guidelines and the invention is not limited to the particular sequences or fragments thereof given here but also include homologous sequences obtained from any source, for example related bacterial proteins, and synthetic peptides, as well as variants (particularly natural variants) or derivatives thereof. Loop sequences given are meant as guidelines, and it is envisaged that any loop sequence comprising an epitope present in the loops described above may be utilised.

Thus, the present invention encompasses variants, homologues or derivatives of the amino acid sequences of the present invention or for use in the invention, as well as variants, homologues or derivatives of the amino acid sequences.

In the context of the present invention, a homologous sequence is taken to include an amino acid sequence which is at least 60, 70, 80 or 90% identical, preferably at least 95 or 98% identical at the amino acid level. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps.

Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Where a protein is specifically mentioned herein, it is preferably a reference to a full-length protein but it may also encompass antigenic fragments thereof (particularly in the context of subunit vaccines). Preferred fragments include those which include an epitope. Particularly preferred fragments include those with at least one surface loop. With respect to the mutants of the present invention this loop is preferably other than loop 7 and/or loop 5. These fragments may contain or comprise at least 10 amino acids, preferably 20 amino acids, more preferably 30 amino acids, more preferably 40 amino acids or most preferably 50 amino acids, taken contiguously from the amino acid sequence of the protein. In addition, antigenic fragments denotes fragments that are immunologically reactive with antibodies generated against the Neisserial proteins (or other Gram negative bacteria) or with antibodies generated by infection of a mammalian host with *Neisseria*. Antigenic fragments also includes fragments that when administered at an effective dose, elicit a protective immune response against Neisserial (or other Gram negative bacterial) infection, more preferably it is protective against *N. meningitidis* and/or *N. gonorrhoeae* infection, most preferably it is protective against *N. meningitidis* serogroup B infection.

The present invention also includes variants of the proteins mentioned herein, that is proteins that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, 1-3, 1-2 or 1 amino acids are substituted, deleted, or added in any combination.

The chimeric protein produced by the present invention is preferably a product which displays at least some of the immunological activity of the wild type Imp protein. Preferably it will show at least one of the following:

An ability to induce the production of antibodies which recognise the wild type Imp (if necessary when the Imp protein of the present invention is coupled to a carrier);

An ability to induce the production of antibodies that can protect against experimental infection; and/or An ability to induce, when administered to an animal, the development of an immunological response that can protect against Gram negative bacterial infection, preferably Neisserial infection such as *Neisseria meningitidis* or *Neisseria gonorrhoeae* infection.

Preferably the mutant protein of the present invention is cross-reactive and more preferably cross-protective.

The chimeric protein of the present invention is useful in prophylactic, therapeutic and diagnostic composition for preventing treating and diagnosing diseases caused by Gram negative bacteria, preferably *Neisseria*, particularly *Neisseria meningitidis*; although it may also have similar applications in relation to, e.g. *Neisseria gonorrhoeae* or *Neisseria lactamica*.

Standard immunological techniques may be employed with the chimeric protein of the present invention in order to use it as an immunogen and as a vaccine. In particular, any suitable host may be injected with a pharmaceutically effective amount of the chimeric protein to generate monoclonal or polyclonal anti-Imp antibodies or to induce the development of a protective immunological response against a *Neisseria* disease. Prior to administration, the chimeric protein may be formulated in a suitable vehicle, and thus we provide a pharmaceutical composition comprising a pharmaceutically effective amount of one or more proteins of the present invention. As used herein "pharmaceutically effective amount" refers to an amount of Imp (or other proteins of the invention) protein that elicits a sufficient titre of antibodies to treat or prevent infection. The pharmaceutical composition of the present invention may also comprise other antigens useful in treating or preventing disease.

Polynucleotide

The present invention also provides polynucleotides which code for the chimeric proteins of the present invention, including variants, derivatives and homologs thereof. Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

In one embodiment the mutant proteins of the present invention are produced using any one of the following techniques: site-directed mutagenesis including cassette mutagenesis, single primer extension, a PCR method of site-directed mutagenesis for example the four-primer method of Higuchi et al (1988) Nucleic Acids Res. 16:7351-67, unidirectional deletion; random mutagenesis; and selection of mutant proteins by phage display.

The terms "variant", "homologue" or "derivative" in relation to the nucleotide sequence of the present invention include any substitution of, variation of, modification of, replacement of, deletion of or addition of one (or more) nucleic acid from or to the sequence providing the resultant nucleotide sequence codes for a mutant Imp or MsbA polypeptide.

As indicated above, with respect to sequence homology, preferably there is at least 75%, more preferably at least 85%, more preferably at least 90% homology (preferably identity) to the polynucleotide sequences shown herein or there is at least 75%, more preferably at least 85%, more preferably at least 90% homology (preferably identity) to polynucleotides encoding polypeptide sequences shown herein. More preferably there is at least 95%, more preferably at least 98%, homology (preferably identity). Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein or to polynucleotides encoding the polypeptide sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides of the invention capable of selectively hybridising to the nucleotide sequences presented herein, polynucleotides encoding polypeptide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides. Preferred polynucleotides of the invention will comprise regions homologous to nucleotides which code for conserved regions, preferably at least 80 or 90% and more preferably at least 95% homologous (preferably identical) to these regions.

The term "selectively hybridizable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M Na$_3$ Citrate pH 7.0}).

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other bacterial homologues may be obtained and such homologues and fragments thereof in general will be capable of selectively hybridising to the sequences shown in the sequence listing herein.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein. Preferred fragments are less than 5000, 2000, 1000, 500 or 200 nucleotides in length.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Vectors, Host Cells, Expression Systems

The invention may employ vectors that comprise a polynucleotide which codes for at least a chimeric Imp or MsbA protein or may comprise polynucleotides of the present invention which code for a mutant Imp or MsbA protein with reduced LPS transporter activity of the present invention. Host cells that are genetically engineered with vectors of the invention (which may alter the genome of the cell) and the production of mutant, preferably chimeric Imp proteins by recombinant techniques are further aspects of the invention. Cell-free translation systems can also be employed to produce such proteins using RNAs derived from DNA constructs.

Recombinant proteins of the present invention may be prepared by processes well known to those skilled in the art from genetically engineered host cells comprising expression systems.

For recombinant production of the proteins of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, *E. coli, streptomyces*, cyanobacteria, *Bacillus subtilis, Moraxella catarrhalis, Haemophilus influenzae* and *Neisseria meningitidis*; fungal cells, such as cells of a yeast, *Kluveromyces, Saccharomyces*, a basidiomycete, *Candida albicans* and *Aspergillus*; insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the proteins of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a protein in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed protein. These signals may be endogenous to the protein or they may be heterologous signals. Proteins of the present invention can be recovered and purified from recombinant cell cultures by the method of the present invention.

Antibodies

The proteins of the invention can be used as immunogens to produce antibodies immunospecific for such proteins.

In certain preferred embodiments of the invention there are provided antibodies against the Imp or MsbA protein of the invention.

Antibodies generated against the proteins of the invention can be obtained by administering the proteins of the invention, or epitope-bearing fragments of either or both, analogues of either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495-497 (1975); Kozbor et al., *Immunology Today* 4: 72 (1983); Cole et al., pg. 77-96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to proteins of this invention. Also, transgenic mice, or other organisms or animals, such as other mammals, may be used to express humanized antibodies immunospecific to the proteins of the invention.

Alternatively, phage display technology may be utilized to select antibody genes with binding activities towards a protein of the invention either from repertoires of PCR amplified v-genes of lymphocytes from humans screened for possessing anti-FrpB or from naive libraries (McCafferty, et al., (1990), Nature 348, 552-554; Marks, et al., (1992) *Biotechnology* 10, 779-783). The affinity of these antibodies can also be improved by, for example, chain shuffling (Clackson et al., (1991) *Nature* 352: 628).

The above-described antibodies may be employed to isolate or to identify clones expressing chimeric or mutated Imp or MsbA proteins of the invention to purify the proteins or polynucleotides by, for example, affinity chromatography.

Thus, among others, antibodies against the Imp protein of the invention may be employed to treat infections, particularly bacterial infections, preferably Neisserial infections.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al. (1986), *Nature* 321, 522-525 or Tempest et al., (1991) *Biotechnology* 9, 266-273.

A protein of the present invention can be administered to a recipient who then acts as a source of immune globulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat Neisserial infection. Hyperimmune globulins of the invention are particularly useful for treatment or prevention of Neisserial disease in infants, immune compromised individuals or where treatment is required and there is no time for the individual to produce antibodies in response to vaccination.

An additional aspect of the invention is a pharmaceutical composition comprising a monoclonal antibody (or fragments thereof; preferably human or humanised) reactive against the pharmaceutical composition of the invention, which could be used to treat or prevent infection by Gram negative bacteria, preferably *Neisseria*, more preferably *Neisseria meningitidis* or *Neisseria gonorrhoeae* and most preferably *Neisseria meningitidis* serogroup B.

Such pharmaceutical compositions comprise monoclonal antibodies that can be whole immunoglobulins of any class e.g. IgG1-4, IgM, IgA1 or 2, IgD or IgE, chimeric antibodies or hybrid antibodies with specificity to two or more antigens of the invention. They may also be fragments e.g. F(ab')2, Fab', Fab, Fv, ScFv and the like including hybrid fragments.

Methods of making monoclonal antibodies are well known in the art and can include the fusion of splenocytes with myeloma cells (Kohler and Milstein 1975 Nature 256; 495; Antibodies—a laboratory manual Harlow and Lane 1988). Alternatively, monoclonal Fv fragments can be obtained by screening a suitable phage display library (Vaughan T J et al 1998 Nature Biotechnology 16; 535). Monoclonal antibodies may be humanised or part humanised by known methods.

Vaccines

Another aspect of the invention relates to a method for inducing an immunological response in an individual, particularly a mammal, preferably humans, which comprises inoculating the individual with the Gram negative bacterium of the invention or a fraction or membrane thereof, or with the chimeric protein of the invention or with an outer membrane vesicle of the invention or a pharmaceutical composition or vaccine of the invention, adequate to produce antibody and/or T cell immune response to protect (or treat) said individual from infection, particularly bacterial infection and most particularly *Neisseria meningitidis* infection. Also provided are methods whereby such immunological response slows bacterial replication.

A further aspect of the invention relates to a pharmaceutical composition or vaccine that when introduced into an individual, preferably a human, capable of having induced within it an immunological response, induces an immunological response in such individual to a chimeric protein of the present invention. Preferably the immunological response is against an Imp epitope and at least one insert epitope from a separate protein. The immunological response may be used therapeutically or prophylactically and may take the form of antibody immunity and/or cellular immunity, such as cellular immunity arising from CTL or CD4+ T cells.

Also provided by this invention are compositions, particularly vaccine compositions, and methods comprising the proteins of the invention and immunostimulatory DNA sequences, such as those described in Sato, Y. et al. Science 273: 352 (1996).

The invention thus also includes a vaccine formulation which comprises a Gram negative bacterium of the present invention or fraction thereof, or a chimeric protein of the present invention or an outer membrane vesicle preparation of the invention, together with a suitable carrier, such as a pharmaceutically acceptable carrier. Since the proteins may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The formulation may also be administered mucosally, e.g. intranasally.

The vaccine formulation of the invention may also include adjuvant systems for enhancing the immunogenicity of the formulation. Typically aluminium phosphate or aluminium hydroxide may be used. Preferably the adjuvant system raises preferentially a TH1 type of response.

An immune response may be broadly distinguished into two extreme categories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4 +ve T cell clones by Mosmann and Coffman (Mosmann, T. R. and Coffman, R. L. (1989) *TH1 and TH2 cells: different patterns of lymphokine secretion lead to different functional properties. Annual Review of Immunology,* 7, p 145-173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant, and is preferred. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA). Altenatively, other non-toxic derivatives of LPS may be used.

Preferably, the particles of 3D-MPL are small enough to be sterile filtered through a 0.22 micron membrane (European Patent number 0 689 454). 3D-MPL will be present in the range of 10 µg-100 µg preferably 25-50 µg per dose wherein the antigen will typically be present in a range 2-50 µg per dose.

Another preferred adjuvant comprises QS21, an Hplc purified non-toxic fraction derived from the bark of Quillaja *Saponaria* Molina. Optionally this may be admixed with 3 De-O-acylated monophosphoryl lipid A (3D-MPL), or other non-toxic LPS derivative, optionally together with a carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL:QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and TWEEN® 80 (polysorbate 80). In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 µg-200 µg, such as 10-100 µg, preferably 10 µg-50 µg per dose. Typically the oil in water will comprise from 2 to 10% squalene, from 2 to 10% alpha tocopherol and from 0.3 to 3% TWEEN® 80 (polysorbate 80). Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. TWEEN® 80 (polysorbate 80), in an aqueous carrier. The aqueous carrier may be, for example, phosphate buffered saline.

A particularly potent adjuvant formulation involving QS21, 3D-MPL and tocopherol in oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

Outer Membrane Vesicle Preparations

A preferred embodiment of the invention is an outer membrane vesicle preparation derived from the Gram negative bacterium of any one of the invention or comprising the chimeric protein of the invention.

N. meningitidis serogroup B (menB) excretes outer membrane blebs in sufficient quantities to allow their manufacture on an industrial scale. Outer membrane vesicles may also be prepared via the process of detergent extraction of the bacterial cells (see for example EP 11243).

The outer membrane vesicle preparation of the invention is therefore a convenient way of presenting many antigens including Imp epitopes and epitopes from heterologous proteins within a context of other antigens from the Gram negative bacterium.

Preferably, the outer membrane vesicle preparation of the invention contains reduced levels of LPS due to the loss of LPS transporting activity. Preferably, the presence of the chimeric protein of the invention or an Imp and/or MsbA protein with reduced LPS transporting activity results in a decrease of the amount of LPS on the outer membrane of at least 50%, 60%, 70%, preferably 80%, 90% or more preferably 95% or 99% or 100% compared to an outer membrane vesicle preparation derived from a similar strain of Gram negative bacteria in which Imp is not down regulated. This is preferably realised by isolating the outer membrane vesicles without a detergent extraction step (or using less than or equal to 0.1, 0.05 or 0.01% DOC).

Most preferably, the outer membrane vesicle preparation of the invention contains a level of LPS sufficiently low so that the toxicity is reduced to a level at which the outer membrane vesicle preparation has an acceptable level of reactogenicity when inoculated into a patient.

Additional Features of the Outer Membrane Preparation

The outer membrane vesicle preparation has preferably been engineered to have higher levels of expression of at additional antigens by recombinantly upregulating their expression. Examples of antigens which would be upregulated in such a outer membrane vesicle preparation in addition to the chimeric protein of the present invention include; NspA, Hsf, Hap, OMP85, TbpA (high), TbpA (low), LbpA, TbpB, LbpB, PilQ and PldA. Such preparations would optionally also comprise either or both of LPS immunotype L2 and LPS immunotype L3.

The manufacture of bleb preparations from Neisserial strains may be achieved by any of the methods well known or apparent to a skilled person. Preferably the methods disclosed in EP 301992, U.S. Pat. No. 5,597,572, EP 11243 or U.S. Pat. No. 4,271,147, Frederikson et al. (NIPH Annals [1991], 14:67-80), Zollinger et al. (J. Clin. Invest. [1979], 63:836-848), Saunders et al. (Infect. Immun. [1999], 67:113-119), Drabick et al. (Vaccine [2000], 18:160-172) or WO 01/09350 (Example 8) are used. In general, OMVs are extracted with a detergent, preferably deoxycholate, and nucleic acids are optionally removed enzymatically. Purification is achieved by ultracentrifugation optionally followed by size exclusion chromatography. If 2 or more different blebs of the invention are included, they may be combined in a single container to form a multivalent preparation of the invention (although a preparation is also considered multivalent if the different blebs of the invention are separate compositions in separate containers which are administered at the same time [the same visit to a practitioner] to a host). OMV preparations are usually sterilised by filtration through a 0.2 µm filter, and are preferably stored in a sucrose solution (e.g. 3%) which is known to stabilise the bleb preparations.

Upregulation of proteins within outer membrane vesicle preparations may be achieved by insertion of an extra copy of a gene into the Neisserial strain from which the OMV preparation is derived. Alternatively, the promoter of a gene can be exchanged for a stronger promoter in the Neisserial strain from which the OMV preparation is derived. Such techniques are described in WO01/09350. If an extra copy of the gene is introduced, it too can have a non-native strong promoter operably linked for overexpression. Upregulation of a protein will lead to a higher level of protein being present in OMV compared to the level of protein present in OMV derived from unmodified N. meningitidis (for instance strain H44/76). Preferably the level will be 1.5, 2, 3, 4, 5, 7, or 20 times higher.

Where the presence of the chimeric protein of the invention does not lead to sufficiently low levels of LPS being present in the outer membrane vesicle preparation and LPS is intended to be an additional antigen in the OMV, a protocol using a low concentration of extracting detergent (for example deoxycholate or DOC) may preferably be used in the OMV preparation method so as to preserve high levels of bound LPS whilst removing particularly toxic, poorly bound LPS. The concentration of DOC used is preferably 0-0.3% DOC, more preferably 0.05%-0.2% DOC, most preferably around 0.1% DOC.

"Stronger promoter sequence" refers to a regulatory control element that increases transcription for a gene encoding antigen of interest.

"Upregulating expression" refers to any means to enhance the expression of an antigen of interest, relative to that of the non-modified (i.e., naturally occurring) bleb. It is understood that the amount of 'upregulation' will vary depending on the particular antigen of interest but will not exceed an amount that will disrupt the membrane integrity of the bleb. Upregulation of an antigen refers to expression that is at least 10% higher than that of the non-modified bleb. Preferably it is at least 50% higher. More preferably it is at least 100% (2 fold) higher. Alternatively or additionally, upregulating expression may refer to rendering expression non-conditional on metabolic or nutritional changes, particularly in the case of FrpB, TbpA, TbpB, LbpA and LbpB. In general where FrpB is overexpressed in a bleb this may be done by removing regulatory sequences from the promoter, or by replacement of the promoter for a strong, non-regulated promoter such as PorA.

Again for the purpose of clarity, the terms 'engineering a bacterial strain to produce less of said antigen' or down regulation refers to any means to reduce the expression of an antigen (or the expression of a functional gene product) of interest, relative to that of the non-modified (i.e., naturally occurring bleb), preferably by deletion, such that expression is at least 10% lower than that of the non-modified bleb. Preferably it is at least 50% lower and most preferably completely absent. If the down regulated protein is an enzyme or a functional protein, the downregulation may be achieved by introducing one or more mutations resulting in a 10%, 20%, 50%, 80% or preferably a 100% reduction in enzymatic or functional activity.

The engineering steps required to modulate the expression of Neisserial proteins can be carried out in a variety of ways known to the skilled person. For instance, sequences (e.g. promoters or open reading frames) can be inserted, and promoters/genes can be disrupted by the technique of transposon insertion. For instance, for upregulating a gene's expression, a strong promoter could be inserted via a transposon up to 2 kb upstream of the gene's initiation codon (more preferably 200-600 bp upstream, most preferably approximately 400 bp upstream). Point mutation or deletion may also be used (particularly for down-regulating expression of a gene).

Such methods, however, may be quite unstable or uncertain, and therefore it is preferred that the engineering step is performed via a homologous recombination event. Preferably, the event takes place between a sequence (a recombinogenic region) of at least 30 nucleotides on the bacterial chromosome, and a sequence (a second recombinogenic region) of at least 30 nucleotides on a vector transformed within the strain. Preferably the regions are 40-1000 nucleotides, more preferably 100-800 nucleotides, most preferably 500 nucleotides). These recombinogenic regions should be sufficiently similar that they are capable of hybridising to one another under highly stringent conditions.

Methods used to carry out the genetic modification events herein described (such as the upregulation or downregulation of genes by recombination events and the introduction of further gene sequences into a Neisserial genome) are described in WO01/09350. Typical strong promoters that may be integrated in Neisseria are porA, porB, IgtF, Opa, p110, lst, and hpuAB. PorA and PorB are preferred as constitutive, strong promoters. It has been established that the PorB promoter activity is contained in a fragment corresponding to nucleotides −1 to −250 upstream of the initation codon of porB.

Down Regulation/Removal of Variable and Non-Protective Immunodominant Antigens

Many surface antigens are variable among bacterial strains and as a consequence are protective only against a limited set of closely related strains. An aspect of this invention covers outer membrane vesicles of the invention in which the expression of other proteins is reduced, or, preferably, gene(s) encoding variable surface protein(s) are deleted. Such deletion results in a bacterial strain producing blebs which, when administered in a vaccine, have a stronger potential for cross-reactivity against various strains due to a higher influence exerted by conserved proteins (retained on the outer membranes) on the vaccinee's immune system. Examples of such variable antigens in Neisseria that may be downregulated in the bleb immunogenic compositions of the invention include PorA, PorB, and Opa.

Other types of gene that could be down-regulated or switched off are genes which, in vivo, can easily be switched on (expressed) or off by the bacterium. As outer membrane proteins encoded by such genes are not always present on the bacteria, the presence of such proteins in the bleb preparations can also be detrimental to the effectiveness of the vaccine for the reasons stated above. A preferred example to down-regulate or delete is Neisseria Opc protein. Anti-Opc immunity induced by an Opc containing bleb vaccine would only have limited protective capacity as the infecting organism could easily become Opc$^-$.

For example, these variable or non-protective genes may be down-regulated in expression, or terminally switched off. This has the advantage of concentrating the immune system on better antigens that are present in low amounts on the outer surface of blebs. By down-regulation it is also meant that surface exposed, variable immunodominant loops of the above outer membrane proteins may be altered or deleted in order to make the resulting outer membrane protein less immunodominant.

Methods for downregulation of expression are disclosed in WO01/09350. Preferred combinations of proteins to be downregulated in the bleb immunogenic compositions of the invention include PorA and OpA; PorA and OpC; OpA and OpC; PorA and OpA and OpC.

Detoxification of LPS

In certain embodiments of the invention, where the outer membrane vesicle preparation has too high a level of toxicity due to the presence of LPS, the outer membrane vesicle preparation may be detoxified via methods for detoxification of LPS which are disclosed in WO01/09350. In particular methods for detoxification of LPS of the invention involve the downregulation of htrB and/or msbB enzymes are disclosed in WO01/09350. Such methods are preferably combined with methods of bleb extraction involving low levels of DOC, preferably 0-0.3% DOC, more preferably 0.05%-0.2% DOC, most preferably around 0.1% DOC.

Cross-Reactive Polysaccharides

The isolation of bacterial outer-membrane blebs from encapsulated Gram-negative bacteria often results in the co-purification of capsular polysaccharide. In some cases, this "contaminant" material may prove useful since polysaccharide may enhance the immune response conferred by other bleb components. In other cases however, the presence of contaminating polysaccharide material in bacterial bleb preparations may prove detrimental to the use of the blebs in a vaccine. For instance, it has been shown at least in the case of N. meningitidis that the serogroup B capsular polysaccharide does not confer protective immunity and is susceptible to induce an adverse auto-immune response in humans. Consequently, outer membrane vesicles of the invention may be isolated from a bacterial strain for bleb production, which has been engineered such that it is free of capsular polysaccharide. The blebs will then be suitable for use in humans. A particularly preferred example of such a bleb preparation is one from N. meningitidis serogroup B devoid of capsular polysaccharide.

This may be achieved by using modified bleb production strains in which the genes necessary for capsular biosynthesis and/or export have been impaired. Inactivation of the gene coding for capsular polysaccharide biosynthesis or export can be achieved by mutating (point mutation, deletion or insertion) either the control region, the coding region or both (preferably using the homologous recombination techniques described above), or by any other way of decreasing the enzymatic function of such genes. Moreover, inactivation of capsular biosynthesis genes may also be achieved by antisense over-expression or transposon mutagenesis. A preferred method is the deletion of some or all of the *Neisseria meningitidis* cps genes required for polysaccharide biosynthesis and export. For this purpose, the replacement plasmid pMF121 (described in Frosh et al. 1990, *Mol. Microbiol.* 4:1215-1218) can be used to deliver a mutation deleting the cpsCAD (+galE) gene cluster.

Preferably the siaD gene is deleted, or down-regulated in expression or the gene product enzymatically inactivated by any other way (the meningococcal siaD gene encodes alpha-2,3-sialyltransferase, an enzyme required for capsular polysaccharide and LOS synthesis). This mutation is preferred in order to cause minimum disruption to LPS epitopes which are preferably conserved in the preparations of the invention.

In bleb preparations, particularly in preparations extracted with low DOC concentrations LPS may be used as an antigen in the immunogenic composition of the invention. It is however advantageous to downregulate/delete/inactivate enzymatic function of either the IgtE or preferably IgtB genes/gene products in order to remove human like lacto-N-neotetraose structures. The Neisserial locus (and sequence thereof) comprising the Igt genes for the biosynthesis of LPS oligosaccharide structure is known in the art (Jennings et al Micorbiology 1999 145; 3013-3021). Downregulation/deletion of IgtB (or functional gene product) is preferred since it leaves the LPS protective epitope intact. In *N. meningitidis* serogroup B bleb preparations of the invention, the down-regulation/deletion of both siaD and IgtB is preferred, leading to a bleb preparation with optimal safety and LPS protective epitope retention.

Pharmaceutical compositions of the invention optionally comprise equal to or at least, one, two, three, four or five different outer membrane vesicle preparations. Where two or more OMV preparations are included, at least one antigen is preferably upregulated in each OMV. Such OMV preparations may be derived from Neisserial strains of the same species and serogroup or preferably from Neisserial strains of different class, serogroup, serotype, subserotype or immunotype. For example, an immunogenic composition may comprise one or more outer membrane vesicle preparation(s) which contains LPS of immunotype L2 and one or more outer membrane vesicle preparation which contains LPS of immunotype L3. L2 or L3 OMV preparations are preferably derived from a stable strain which has minimal phase variability in the LPS oligosaccharide synthesis gene locus.

Combinations

The pharmaceutical compositions of the present invention, may also comprise at least one or more of the following:

a. one or more subunit vaccines;

b. one or more outer membrane vesicles with one or more antigens upregulated; and c. a mixture of a. and b.

The pharmaceutical compositions of the invention may thus also comprise both a subunit composition and an outer membrane vesicle.

The outer membrane vesicle preparation may have at least one different antigen selected from the following list which has been recombinantly upregulated in an outer membrane vesicle: NspA, Hsf, Hap, OMP85, TbpA (high), TbpA (low), LbpA, TbpB, LbpB, NadA, TspA, TspB, PilQ and PldA; and optionally comprise either or both of LPS immunotype L2 and LPS immunotype L3.

There are several antigens that are particularly suitable for inclusion in a subunit composition due to their solubility. Examples of such proteins include; FhaB, NspA, passenger domain of Hsf, passenger domain of Hap, OMP85, FrpA, FrpC, TbpB, LbpB, PilQ.

Neisserial infections progress through several different stages. For example, the meningococcal life cycle involve nasopharyngeal colonisation, mucosal attachment, crossing into the bloodstream, multiplication in the blood, induction of toxic shock, crossing the blood/brain barrier and multiplication in the cerebrospinal fluid and/or the meninges. Different molecules on the surface of the bacterium will be involved in different steps of the infection cycle. By targeting the immune response against an effective amount of a combination of particular antigens, involved in different processes of Neisserial infection, a Neisserial vaccine with surprisingly high efficacy can be achieved.

In particular, combinations of certain Neisserial antigens from different classes with the chimeric protein of the invention can elicit an immune response which protects against multiple stages of infection. Such combinations of antigens can surprisingly lead to synergistically improved vaccine efficacy against Neisserial infection where more that one function of the bacterium is targeted by the immune response in an optimal fashion. Some of the further antigens which can be included are involved in adhesion to host cells, some are involved in iron acquisition, some are autotransporters and some are toxins.

The efficacy of vaccines can be assessed through a variety of assays. Protection assays in animal models are well known in the art. Furthermore, serum bactericidal assay (SBA) is the most commonly agreed immunological marker to estimate the efficacy of a meningococcal vaccine (Perkins et al. J Infect Dis. 1998, 177:683-691).

Some combinations of antigens can lead to improved protection in animal model assays and/or synergistically higher SBA titres. Without wishing to be bound by theory, such synergistic combinations of antigens are enabled by a number of characteristics of the immune response to the antigen combination. The antigens themselves are usually surface exposed on the Neisserial cells and tend to be conserved but also tend not to be present in sufficient quantity on the surface cell for an optimal bactericidal response to take place using antibodies elicited against the antigen alone. Combining the antigens of the invention can result in a formulation eliciting an advantageous combination of bactericidal antibodies which interact with the Neisserial cell beyond a critical threshold. At this critical level, sufficient antibodies of sufficient quality bind to the surface of the bacterium to allow efficient killing by complement and much higher bactericidal effects are seen as a consequence. As serum bactericidal assays (SBA) closely reflect the efficacy of vaccine candidates, the attainment of good SBA titres by a combination of antigens is a good indication of the protective efficacy of a vaccine containing that combination of antigens.

An additional advantage of the invention is that the combination of the antigens of the invention from different families of proteins in an immunogenic composition will enable protection against a wider range of strains.

The invention thus also relates to immunogenic compositions comprising a plurality of proteins selected from at least two different categories of protein, having different functions within *Neisseria*. Examples of such categories of proteins are adhesins, autotransporter proteins, toxins and Fe acquisition proteins. The vaccine combinations of the invention show surprising improvement in vaccine efficacy against homologous Neisserial strains (strains from which the antigens are derived) and preferably also against heterologous Neisserial strains.

In particular, the invention provides immunogenic compositions that comprise at least one, two, three, four five, six, seven, eight, nine or ten different additional Neisseria antigens (to FrpB) selected from at least one, two, three, four or five groups of proteins selected from the following:

at least one Neisserial adhesin selected from the group consisting of FhaB, Hsf, NspA, NadA, PilC, Hap, MafA, MafB Omp26, NMB0315, NMB0995 and NMB1119;

at least one Neisserial autotransporter selected from the group consisting of Hsf, Hap, IgA protease, AspA and NadA;

at least one Neisserial toxin selected from the group consisting of FrpA, FrpC, FrpA/C, VapD, NM-ADPRT, and either or both of LPS immunotype L2 and LPS immunotype L3;

at least one Neisserial Fe acquisition protein selected from the group consisting of TbpA high, TbpA low, TbpB high, TbpB low, LbpA, LbpB, P2086, HpuA, HpuB, Lipo28, Sibp, FbpA, BfrA, BfrB, Bcp, NMB0964 and NMB0293; and at least one Neisserial membrane associated protein, preferably outer membrane protein, selected from the group consisting of PldA, TspA, FhaC, NspA, TbpA(high), TbpA(low), LbpA, HpuB, TdfH, PorB, HimD, H isD, GNA1870, OstA, HlpA, MltA, NMB 1124, NMB 1162, NMB 1220, NMB 1313, NMB 1953, HtrA, TspB, PilQ and OMP85.

and preferably:
a. at least one Neisserial adhesin selected from the group consisting of FhaB, Hsf and NadA;
b. at least one Neisserial autotransporter selected from the group consisting of Hsf, Hap and NadA;
c. at least one Neisserial toxin selected from the group consisting of FrpA, FrpC, and either or both of LPS immunotype L2 and LPS immunotype L3;
d. at least one Neisserial Fe acquisition protein selected from the group consisting of TbpA, TbpB, LbpA and LbpB; and
e. at least one Neisserial outer membrane protein selected from the group consisting of TspA, TspB, NspA, PilQ, OMP85, and PldA.

Preferably the first four (and most preferably all five) groups of antigen are represented in the pharmaceutical composition of the invention.

As previously mentioned where a protein is specifically mentioned herein, it is preferably a reference to a native, full-length protein but it may also encompass antigenic fragments thereof (particularly in the context of subunit vaccines). These are fragments containing or comprising at least 10 amino acids, preferably 20 amino acids, more preferably 30 amino acids, more preferably 40 amino acids or most preferably 50 amino acids, taken contiguously from the amino acid sequence of the protein. In addition, antigenic fragments denotes fragments that are immunologically reactive with antibodies generated against the Neisserial proteins or with antibodies generated by infection of a mammalian host with Neisseria. Antigenic fragments also includes fragments that when administered at an effective dose, elicit a protective immune response against Neisserial infection, more preferably it is protective against N. meningitidis and/or N. gonorrhoeae infection, most preferably it is protective against N. meningitidis serogroup B infection.

Also included in the invention are recombinant fusion proteins of Neisserial proteins of the invention, or fragments thereof. These may combine different Neisserial proteins or fragments thereof in the same protein. Alternatively, the invention also includes individual fusion proteins of Neisserial proteins or fragments thereof, as a fusion protein with heterologous sequences such as a provider of T-cell epitopes, or viral surface proteins such as influenza virus haemagglutinin, tetanus toxoid, diphtheria toxoid, CRM197.

Addition Antigens of the Invention

NMB references refer to reference numbers to sequences which can be accessed from www.neisseria.org.

1. Adhesins

Adhesins include FhaB (WO98/02547), NadA (J. Exp. Med (2002) 195:1445; NMB 1994), Hsf also known as NhhA (NMB 0992) (WO99/31132), Hap (NMB 1985)(WO99/55873), NspA (WO96/29412), MafA (NMB 0652) and MafB (NMB 0643) (Annu Rev Cell Dev Biol. 16; 423-457 (2000); Nature Biotech 20; 914-921 (2002)), Omp26 (NMB 0181), NMB 0315, NMB 0995, NMB 1119 and PilC (Mol. Microbiol. 1997, 23; 879-892). These are proteins that are involved in the binding of Neisseria to the surface of host cells. Hsf is an example of an adhesin, as well as being an autotransporter protein. Immunogenic compositions of the invention may therefore include combinations of Hsf and other autotransporter proteins where Hsf contributes in its capacity as an adhesin. These adhesins may be derived from Neisseria meningitidis or Neisseria gonorrhoeae or other Neisserial strains. The invention also includes other adhesins from Neisseria.

FhaB

This antigen has been described in WO98/02547 SEQ ID NO 38 (nucleotides 3083-9025)—see also NMB0497. The present inventors have found FhaB to be particularly effectively at inducing anti-adhesive antibodies alone and in particular with other antigens of the invention. Although full length FhaB could be used, the inventors have found that particular C-terminal truncates are surprisingly at least as effective and preferably even more effective in terms of cross-strain effect. Such truncates have also been advantageously shown to be far easier to clone. FhaB truncates of the invention typically correspond to the N-terminal two-thirds of the FhaB molecule, preferably the new C-terminus being situated at position 1200-1600, more preferably at position 1300-1500, and most preferably at position 1430-1440. Specific embodiments have the C-terminus at 1433 or 1436. Accordingly such FhaB truncates of the invention and vaccines comprising such truncates are preferred components of the combination immunogenic compositions of the invention. The N-terminus may also be truncated by up to 10, 20, 30, 40 or 50 amino acids.

2. Autotransporter Proteins

Autotransporter proteins typically are made up of a signal sequence, a passenger domain and an anchoring domain for attachment to the outer membrane. Examples of autotransporter proteins include Hsf (WO99/31132) (NMB 0992), HMW, Hia (van Ulsen et al Immunol. Med. Microbiol. 2001 32; 53-64), Hap (NMB 1985) (WO99/55873; van Ulsen et al Immunol. Med. Microbiol. 2001 32; 53-64), UspA, UspA2, NadA (NMB 1994) (Comanducci et al J. Exp. Med. 2002 195; 1445-1454), AspA (Infection and Immunity 2002, 70(8); 4447-4461; NMB 1029), Aida-1 like protein, SSh-2 and Tsh. NadA (J. Exp. Med (2002) 195:1445) is another example of an autotransporter proteins, as well as being an adhesin. Immunogenic compositions of the invention may therefore include combinations of NadA and adhesins where NadA contributes in its capacity as an autotransporter protein. These proteins may be derived from Neisseria meningitidis or Neisseria gonorrhoeae or other Neisserial strains. The invention also includes other autotransporter proteins from Neisseria.

Hsf

Hsf has a structure that is common to autotransporter proteins. For example, Hsf from N. meningitidis strain H44/76 consists of a signal sequence made up of amino acids 1-51, a head region at the amino terminus of the mature protein (amino acids 52-479) that is surface exposed and contains variable regions (amino acids 52-106, 121-124, 191-210 and 230-234), a neck region (amino acids 480-509), a hydrophobic alpha-helix region (amino acids 518-529) and an anchoring domain in which four transmembrane strands span the outer membrane (amino acids 539-591).

Although full length Hsf may be used in immunogenic compositions of the invention, various Hsf truncates and deletions may also be advantageously used depending on the type of vaccine.

Where Hsf is used in a subunit vaccine, it is preferred that a portion of the soluble passenger domain is used; for instance the complete domain of amino acids 52 to 479, most preferably a conserved portion thereof, for instance the particularly advantageous sequence of amino acids 134 to 479. Preferred forms of Hsf may be truncated so as to delete variable regions of the protein disclosed in WO01/55182. Preferred variants would include the deletion of one, two, three, four, or five variable regions as defined in WO01/55182. The above sequences and those described below, can be extended or truncated by up to 1, 3, 5, 7, 10 or 15 amino acids at either or both N or C termini.

Preferred fragments of Hsf therefore include the entire head region of Hsf, preferably containing amino acids 52-473. Additional preferred fragments of Hsf include surface exposed regions of the head including one or more of the following amino acid sequences; 52-62, 76-93, 116-134, 147-157, 157-175, 199-211, 230-252, 252-270, 284-306, 328-338, 362-391, 408-418, 430-440 and 469-479.

Where Hsf is present in an outer membrane vesicle preparation, it may be expressed as the full-length protein or preferably as an advantageous variant made up of a fusion of amino acids 1-51 and 134-591 (yielding a mature outer membrane protein of amino acid sequence 134 to the C-terminus). Preferred forms of Hsf may be truncated so as to delete variable regions of the protein disclosed in WO01/55182. Preferred variants would include the deletion of one, two, three, four, or five variable regions as defined in WO01/55182. Preferably the first and second variable regions are deleted. Preferred variants would delete residues from between amino acid sequence 52 through to 237 or 54 through to 237, more preferably deleting residues between amino acid 52 through to 133 or 55 through to 133. The mature protein would lack the signal peptide.

Hap

Computer analysis of the Hap-like protein from *Neisseria meningitidis* reveals at least three structural domains. Considering the Hap-like sequence from strain H44/76 as a reference, Domain 1 comprising amino-acid 1 to 42, encodes a sec-dependant signal peptide characteristic of the auto-transporter family, Domain 2 comprising amino-acids 43 to 950, encode the passenger domain likely to be surface exposed and accessible to the immune system, Domain 3, comprising residues 951 to the C-terminus (1457), is predicted to encode a beta-strands likely to assemble into a barrel-like structure and to be anchored into the outer-membrane. Since domains 2 is likely to be surface-exposed, well conserved (more than 80% in all strain tested) and could be produced as subunit antigens in *E. coli*, it represents an interesting vaccine candidates. Since domains 2 and 3 are likely to be surface-exposed, are well conserved (Pizza et al. (2000), Science 287: 1816-1820), they represent interesting vaccine candidates. Domain 2 is known as the passenger domain.

Immunogenic compositions of the invention may comprise the full-length Hap protein, preferably incorporated into an OMV preparation. Immunogenic compositions of the invention may also comprise the passenger domain of Hap which in strain H44/76 is composed of amino acid residues 43-950. This fragment of Hap would be particularly advantageously used in a subunit composition of the invention. The above sequence for the passenger domain of Hap can be extended or truncated by up to 1, 3, 5, 7, 10, 15, 20, 25, or 30 amino acids at either or both N or C termini.

3. Iron Acquisition Proteins

Iron acquisition proteins include TbpA (NMB 0461) (WO92/03467, U.S. Pat. No. 5,912,336, WO93/06861 and EP586266), TbpB (NMB 0460) (WO93/06861 and EP586266), LbpA (NMB 1540) (Med Microbiol (1999) 32:1117), TbpB (NMB 1541)(WO/99/09176), Hue (U73112.2) (Mol. Microbiol. 1997, 23; 737-749), Hub (NC_003116.1) (Mol. Microbiol. 1997, 23; 737-749), P2086 also known as XthA (NMB 0399) ($13^{th}$ International Pathogenic *Neisseria* Conference 2002), FbpA (NMB 0634), FbpB, BfrA (NMB 1207), BfrB (NMB 1206), Lipo28 also known as GNA2132 (NMB 2132), Sibp (NMB 1882), HmbR, HemH, Bcp (NMB 0750), Iron (III) ABC transporter-permease protein (Tettelin et al Science 287; 1809-1815 2000), Iron (III) ABC transporter—periplasmic (Tettelin et al Science 287; 1809-1815 2000), TonB-dependent receptor (NMB 0964 and NMB 0293)(Tettelin et al Science 287; 1809-1815 2000) and transferrin binding protein related protein (Tettelin et al Science 287; 1809-1815 2000). These proteins may be derived from *Neisseria meningitidis, Neisseria gonorrhoeae* or other Neisserial strains. The invention also includes other iron acquisition proteins from *Neisseria.*

TbpA

TbpA interacts with TbpB to form a protein complex on the outer membrane of *Neisseria*, which binds transferrin. Structurally, TbpA contains an intracellular N-terminal domain with a TonB box and plug domain, multiple transmembrane beta strands linked by short intracellular and longer extracellular loops.

Two families of TbpB have been distinguished, having a high molecular weight and a low molecular weight respectively. High and low molecular weight forms of TbpB associate with different families of TbpA which are distinguishable on the basis of homology. Despite being of similar molecular weight, they are known as the high molecular weight and low molecular weight families because of their association with the high or low molecular weight form of TbpB (Rokbi et al FEMS Microbiol. Lett. 100; 51, 1993). The terms TbpA(high) and TbpA(low) are used to refer to these two forms of TbpA, and similarly for TbpB. Immunogenic compositions of the invention may comprise TbpA and TbpB from serogroups A, B, C, Y and W-135 of *N. meningitidis* as well as iron acquisition proteins from other bacteria including *N. gonorrhoeae*. Transferrin binding proteins TbpA and TbpB have also been referred to as Tbp1 and Tbp2 respectively (Cornelissen et al Infection and Immunity 65; 822, 1997).

TbpA contains several distinct regions. For example, in the case of TbpA from *N. meningitidis* strain H44/76, the amino terminal 186 amino acids form an internal globular domain, 22 beta strands span the membrane, forming a beta barrel structure. These are linked by short intracellular loops and larger extracellular loops. Extracellular loops 2, 3 and 5 have the highest degree of sequence variability and loop 5 is surface exposed. Loops 5 and 4 are involved in ligand binding.

Preferred fragments of TbpA include the extracellular loops of TbpA. Using the sequence of TbpA from *N. meningitidis* strain H44/76, these loops correspond to amino acids 200-202 for loop1, amino acids 226-303 for loop 2, amino acids 348-395 for loop 3, amino acids 438-471 for loop 4, amino acids 512-576 for loop 5, amino acids 609-625 for loop 6, amino acids 661-671 for loop 7, amino acids 707-723 for loop 8, amino acids 769-790 for loop 9, amino acids 814-844 for loop 10 and amino acids 872-903 for loop 11. The corresponding sequences, after sequence alignment, in other Tbp proteins would also constitute preferred fragments. Most preferred fragments would include amino acid sequences constituting loop 2, loop 3, loop 4 or loop 5 of Tbp.

Where the immunogenic compositions of the invention comprise TbpA, it is preferable to include both TbpA(high) and TbpA (low).

Although TbpA is preferably presented in an OMV vaccine, it may also be part of a subunit vaccine. For instance, isolated iron acquisition proteins which could be introduced into an immunogenic composition of the invention are well known in the art (WO00/25811). They may be expressed in a bacterial host, extracted using detergent (for instance 2% Elugent) and purified by affinity chromatography or using standard column chromatography techniques well known to the art (Oakhill et al Biochem J. 2002 364; 613-6).

Where TbpA is presented in an OMV vaccine, its expression can be upregulated by genetic techniques discussed herein or in WO 01/09350, or may preferably be upregulated by growth of the parent strain under iron limitation conditions. This process will also result in the upregulation of variable iron-regulated proteins, particularly wild-type FrpB which may become immunodominant and it is therefore advantageous to downregulate the expression of (and preferably delete the genes encoding) such proteins (particularly wild-type FrpB) as described in WO 01/09350, or remove its immunodominant loops as described above, to ensure that the immunogenic composition of the invention elicits an immune response against antigens present in a wide range of Neisserial strains. If wild-type FrpB is deleted, an additional copy of a non immunodominant mutant FrpB gene may be introduced into the cell. It is preferred to have both TbpA(high) and TbpA(low) present in the immunogenic composition and this is preferably achieved by combining OMVs derived from two strains, expressing the alternative forms of TbpA.

4. Toxins

Toxins include FrpA (NMB 0585; NMB 1405), FrpA/C (see below for definition), FrpC NMB 1415; NMB 1405) (WO92/01460), NM-ADPRT (NMB 1343) (13$^{th}$ International Pathogenic *Neisseria* Conference 2002 Masignani et al p135), VapD (NMB 1753), lipopolysaccharide (LPS; also called lipooligosaccharide or LOS) immunotype L2 and LPS immunotype L3. FrpA and FrpC contain a region which is conserved between these two proteins and a preferred fragment of the proteins would be a polypeptide containing this conserved fragment, preferably comprising amino acids 227-1004 of the sequence of FrpA/C. These antigens may be derived from *Neisseria meningitidis* or *Neisseria gonorrhoeae* or other Neisserial strains. The invention also includes other toxins from *Neisseria*.

In an alternative embodiment, toxins may include antigens involved in the regulation of toxicity, for example OstA which functions in the synthesis of lipopolysaccharides.

FrpA and FrpC

Figure 4:
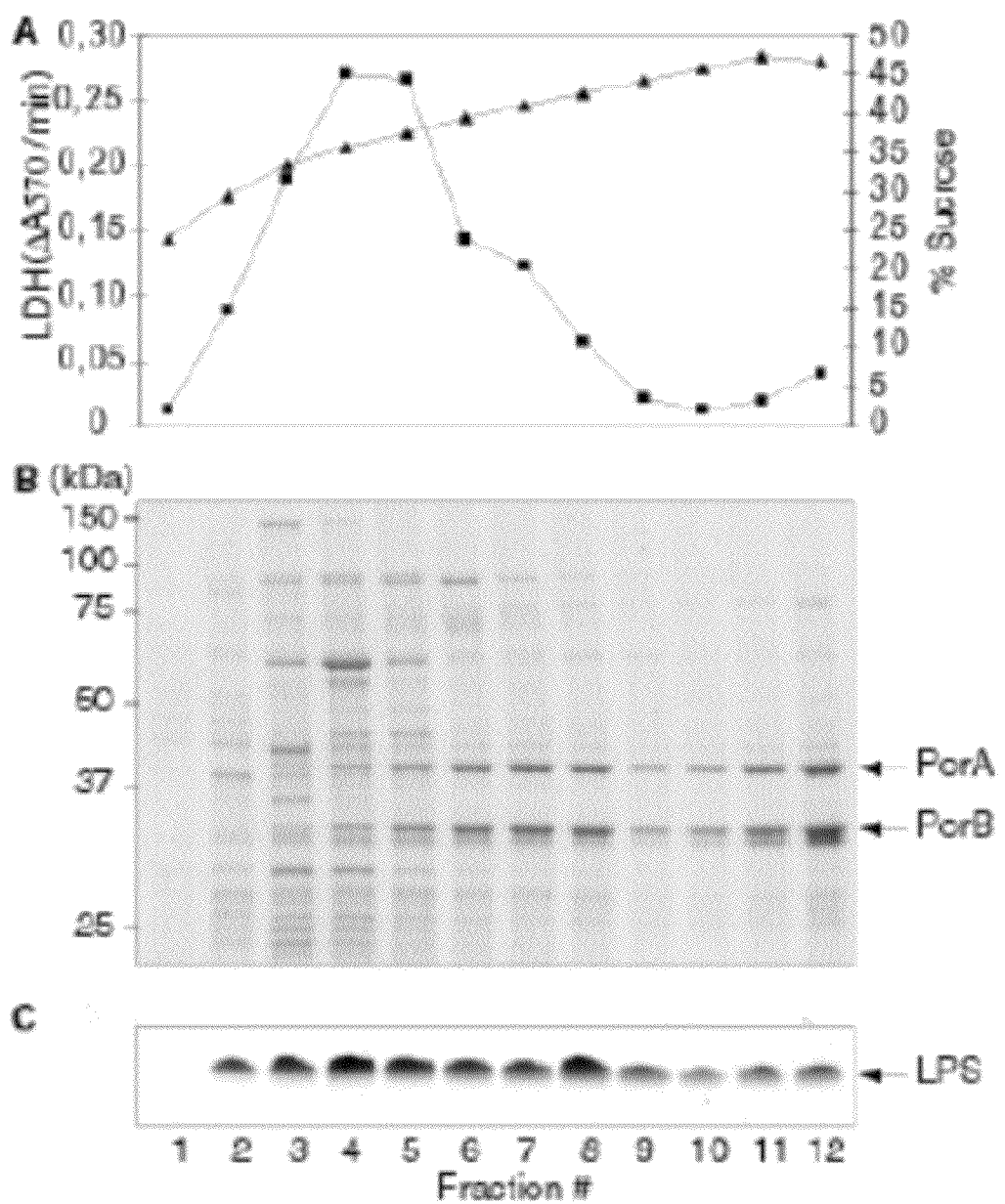
FIG. 4. Analysis of fractions obtained after isopycnic sucrose gradient centrifugation of wild-type Nme membranes. (A) Percentage sucrose (.), measured in a refractometer and LDH activity (|) in the different fractions. (B, C) Equal volumes of each fraction were precipitated with TCA and separated in denaturing SDS-PAGE followed by Coomassie blue staining (B) or separated on Tricine-SDS-PAGE followed by silver staining to visualize LPS(C). The positions of the major OMPs PorA and PorB are indicated. Molecular size markers are indicated in kDa.

*Neisseria meningitidis* encodes two RTX proteins, referred to as FrpA & FrpC secreted upon iron limitation (Thompson et al., (1993) J. Bacteriol. 175:811-818; Thompson et al., (1993) Infect. Immun. 61:2906-2911). The RTX (Repeat ToXin) protein family have in common a series of 9 amino acid repeat near their C-termini with the consensus: Leu Xaa Gly Gly Xaa Gly (Asn/Asp) Asp Xaa, SEQ ID NO: 16/SEQ ID NO:30. (LXGGXGN$_{/D}$DX). The repeats in *E. coli* HlyA are thought to be the site of Ca2+ binding. As represented in FIG. 4, meningococcal FrpA and FrpC proteins, as characterized in strain FAM20, share extensive amino-acid similarity in their central and C-terminal regions but very limited similarity (if any) at the N-terminus. Moreover, the region conserved between FrpA and FrpC exhibit some polymorphism due to repetition (13 times in FrpA and 43 times in FrpC) of a 9 amino acid motif.

Immunogenic compositions of the invention may comprise the full length FrpA and/or FrpC or preferably, a fragment comprising the sequence conserved between FrpA and FrpC. The conserved sequence is made up of repeat units of 9 amino acids. Immunogenic compositions of the invention would preferably comprise more that three repeats, more than 10 repeats, more than 13 repeats, more than 20 repeats or more than 23 repeats.

Such truncates have advantageous properties over the full length molecules, and vaccines comprising such antigens are preferred for being incorporated in the immunogenic compositions of the invention.

Sequences conserved between FrpA and FrpC are designated FrpA/C and wherever FrpA or FrpC forms a constituent of immunogenic compositions of the invention, FrpA/C could be advantageously used. Amino acids 277-1004 of the FrpA sequence is the preferred conserved region. The above sequence can be extended or truncated by up to 1, 3, 5, 7, 10, 15, 20, 25, or 30 amino acids at either or both N or C termini.

LPS

LPS (lipopolysaccharide, also known as LOS—lipooligosaccharide) is the endotoxin on the outer membrane of *Neisseria*. The polysaccharide moiety of the LPS is known to induce bactericidal antibodies.

Heterogeneity within the oligosaccharide moiety of the LPS generates structural and antigenic diversity among different neisserial strains (Griffiss et al. Inf. Immun. 1987; 55: 1792-1800). This has been used to subdivide meningococcal strains into 12 immunotypes (Scholtan et al. J Med Microbiol 1994, 41:236-243). Immunotypes L3, L7, & L9 are immunologically identical and are structurally similar (or even the same) and have therefore been designated L3,7,9 (or, for the purposes of this specification, generically as "L3"). Meningococcal LPS L3,7,9 (L3), L2 and L5 can be modified by sialylation, or by the addition of cytidine 5'-monophosphate-N-acetylneuraminic acid. Although L2, L4 and L6 LPS are distinguishable immunologically, they are structurally similar and where L2 is mentioned herein, either L4 or L6 may be optionally substituted within the scope of the invention. See M. P. Jennings et al, Microbiology 1999, 145, 3013-3021 and Mol Microbiol 2002, 43:931-43 for further illustration of LPS structure and heterogeneity.

Where LPS, preferably meningococcal LPS, is included in a vaccine of the invention, preferably and advantageously either or both of immunotypes L2 and L3 are present. LPS is preferably presented in an outer membrane vesicle (preferably where the vesicle is extracted with a low percentage detergent, more preferably 0-0.5%, 0.02-0.4%, 0.04-0.3%, 0.06-0.2%, 0.08-0.15% or 0.1%, most preferably deoxycholate [DOC]) but may also be part of a subunit vaccine. LPS may be isolated using well known procedure including the hot water-phenol procedure (Wesphal and Jann Meth. Carbo. Chem. 5; 83-91 1965). See also Galanos et al. 1969, Eur J Biochem 9:245-249, and Wu et al. 1987, Anal Bio Chem 160:281-289. LPS may be used plain or conjugated to a source of T-cell epitopes such as tetanus toxoid, Diphtheria toxoid, CRM-197 or OMV outer membrane proteins. Techniques for conjugating isolated LOS are also known (see for instance EP 941738 incorporated by reference herein).

Where LOS (in particular the LOS of the invention) is present in a bleb formulation the LOS is preferably conjugated in situ by methods allowing the conjugation of LOS to one or more outer membrane proteins also present on the bleb preparation (e.g. PorA or PorB in meningococcus).

This process can advantageously enhance the stability and/or immunogenicity (providing T-cell help) and/or antigenicity of the LOS antigen within the bleb formulation—thus giving T-cell help for the T-independent oligosaccharide immunogen in its most protective conformation—as LOS in its natural environment on the surface of meningococcal outer membrane. In addition, conjugation of the LOS within the bleb can result in a detoxification of the LOS (the Lipid A portion being stably buried in the outer membrane thus being less available to cause toxicity). Thus the detoxification methods mentioned herein of isolating blebs from htrB$^-$ or msbB$^-$ mutants, or by adding non toxic peptide functional equivalent of polymyxin B [a molecule with high affinity to Lipid A] to the composition (see WO 93/14115, WO 95/03327, Velucchi et al (1997) J Endotoxin Res 4: 1-12, and EP 976402 for further details of non-toxic peptide functional equivalents of polymyxin B—particularly the use of the peptide SAEP 2 (of sequence KTKCKFLKKC, SEQ ID NO: 17, where the 2 cysteines form a disulphide bridge)) may not be required (but which may be added in combination for additional security). Thus the inventors have found that a composition comprising blebs wherein LOS present in the blebs has been conjugated in an intra-bleb fashion to outer membrane proteins also present in the bleb can form the basis of a vaccine for the treatment or prevention of diseases caused by the organism from which the blebs have been derived, wherein such vaccine is substantially non-toxic and is capable of inducing a T-dependent bactericidal response against LOS in its native environment.

Such bleb preparations may be isolated from the bacterial in question (see WO 01/09350), and then subjected to known conjugation chemistries to link groups (e.g. NH$_2$ or COOH) on the oligosaccharide portion of LOS to groups (e.g. NH$_2$ or COOH) on bleb outer membrane proteins. Cross-linking techniques using glutaraldehyde, formaldehyde, or glutaraldehyde/formaldehyde mixes may be used, but it is preferred that more selective chemistries are used such as EDAC or EDAC/NHS (J. V. Staros, R. W. Wright and D. M. Swingle. Enhancement by N-hydroxysuccinimide of water-soluble carbodiimide-mediated coupling reactions. Analytical chemistry 156: 220-222 (1986); and Bioconjugates Techniques. Greg T. Hermanson (1996) pp 173-176). Other conjugation chemistries or treatments capable of creating covalent links between LOS and protein molecules that could be used are described in EP 941738.

Preferably the bleb preparations are conjugated in the absence of capsular polysaccharide. The blebs may be isolated from a strain which does not produce capsular polysaccharide (naturally or via mutation as described below), or may be purified from most and preferably all contaminating capsular polysaccharide. In this way, the intra-bleb LOS conjugation reaction is much more efficient.

Preferably more than 10, 20, 30, 40, 50, 60, 70, 80, 90, or 95% of the LOS present in the blebs is cross-linked/conjugated.

Intrableb conjugation should preferably incorporate 1, 2 or all 3 of the following process steps: conjugation pH should be greater than pH 7.0, preferably greater than or equal to pH 7.5 (most preferably under pH 9); conditions of 1-5% preferably 2-4% most preferably around 3% sucrose should be maintained during the reaction; NaCl should be minimised in the conjugation reaction, preferably under 0.1M, 0.05M, 0.01M, 0.005M, 0.001M, and most preferably not present at all. All these process features make sure that the blebs remain stable and in solution throughout the conjugation process.

The EDAC/NHS conjugation process is a preferred process for intra-bleb conjugation. EDAC/NHS is preferred to formaldehyde which can cross-link to too high an extent thus adversely affecting filterability. EDAC reacts with carboxylic acids (such as KDO in LOS) to create an active-ester intermediate. In the presence of an amine nucleophile (such as lysines in outer membrane proteins such as PorB), an amide bond is formed with release of an isourea by-product. However, the efficiency of an EDAC-mediated reaction may be increased through the formation of a Sulfo-NHS ester intermediate. The Sulfo-NHS ester survives in aqueous solution longer than the active ester formed from the reaction of EDAC alone with a carboxylate. Thus, higher yields of amide bond formation may be realized using this two-stage process. EDAC/NHS conjugation is discussed in J. V. Staros, R. W. Wright and D. M. Swingle. Enhancement by N-hydroxysuccinimide of water-soluble carbodiimide-mediated coupling reactions. Analytical chemistry 156: 220-222 (1986); and Bioconjugates Techniques. Greg T. Hermanson (1996) pp 173-176. Preferably 0.01-5 mg EDAC/mg bleb is used in the reaction, more preferably 0.05-1 mg EDAC/mg bleb. The amount of EDAC used depends on the amount of LOS present in the sample which in turn depends on the deoxycholate (DOC) % used to extract the blebs. At low % DOC (e.g. 0.1%), high amounts of EDAC are used (1 mg/mg and beyond), however at higher % DOC (e.g. 0.5%), lower amounts of EDAC are used (0.025-0.1 mg/mg) to avoid too much inter-bleb crosslinking.

A preferred process of the invention is therefore a process for producing intra-bleb conjugated LOS (preferably meningococcal) comprising the steps of conjugating blebs in the presence of EDAC/NHS at a pH between pH 7.0 and pH 9.0 (preferably around pH 7.5), in 1-5% (preferably around 3%) sucrose, and optionally in conditions substantially devoid of NaCl (as described above), and isolating the conjugated blebs from the reaction mix.

The reaction may be followed on Western separation gels of the reaction mixture using anti-LOS (e.g. anti-L2 or anti-L3) mAbs to show the increase of LOS molecular weight for a greater proportion of the LOS in the blebs as reaction time goes on.

Yields of 99% blebs can be recovered using such techniques.

EDAC was found to be an excellent intra-bleb cross-linking agent in that it cross-linked LOS to OMP sufficiently for improved LOS T-dependent immunogenicity, but did not cross link it to such a high degree that problems such as poor filterability, aggregation and inter-bleb cross-linking occurred. The morphology of the blebs generated is similar to that of unconjugated blebs (by electron microscope). In addition, the above protocol avoided an overly high cross-linking to take place (which can decrease the immunogenicity of protective OMPs naturally present on the surface of the bleb e.g. TbpA or Hsf).

It is preferred that the meningococcal strain from which the blebs are derived is a mutant strain that cannot produce capsular polysaccharide (in particular siaD$^-$). It is also preferred that immunogenic compositions effective against meningococcal disease comprise both an L2 and L3 bleb, wherein the L2 and L3 LOS are both conjugated to bleb outer membrane proteins. Furthermore, it is preferred that the LOS structure within the intra-bleb conjugated bleb is consistent with it having been derived from an IgtE$^-$ or, preferably, lgtB$^-$ meningococcal strain. Most preferably immunogenic compositions comprise intrableb-conjugated blebs: derived from a mutant meningococcal strain that cannot produce capsular polysaccharide and is IgtB⁻; comprising L2 and L3 blebs derived from mutant meningococcal strains that cannot produce capsular polysaccharide; comprising L2 and L3 blebs derived from mutant meningococcal strains that are IgtB⁻; or most preferably comprising L2 and L3 blebs derived from mutant meningococcal strains that cannot produce capsular polysaccharide and are IgtB⁻.

Typical L3 meningococcal strain that can be used for the present invention is H44/76 menB strain. A typical L2 strain is the B16B6 menB strain or the 39E meningococcus type C strain.

As stated above, the blebs of the invention have been detoxified to a degree by the act of conjugation, and need not be detoxified any further, however further detoxification methods may be used for additional security, for instance using blebs derived from a meningococcal strain that is htrB⁻ or msbB⁻ or adding a non-toxic peptide functional equivalent of polymyxin B [a molecule with high affinity to Lipid A] (preferably SEAP 2) to the bleb composition (as described above).

In the above way meningococcal blebs and immunogenic compositions comprising blebs are provided which have as an important antigen LOS which is substantially non-toxic, devoid of autoimmunity problems, has a T-dependent character, is present in its natural environment, and is capable of inducing a bactericidal antibody response against more than 90% of meningococcal strains (in the case of L2+L3 compositions).

5. Integral Outer Membrane Proteins

Other categories of Neisserial proteins may also be candidates for inclusion in the Neisserial vaccines of the invention and may be able to combine with other antigens in a surprisingly effective manner. Membrane associated proteins, particularly integral membrane proteins and most advantageously outer membrane proteins, especially integral outer membrane proteins may be used in the compositions of the present invention. An example of such a protein is PldA also known as Omp1A (NMB 0464) (WO00/15801) which is a Neisserial phospholipase outer membrane protein. Further examples are TspA (NMB 0341) (Infect. Immun. 1999, 67; 3533-3541) and TspB (T-cell stimulating protein) (WO 00/03003; NMB 1548, NMB 1628 or NMB 1747). Further examples include PilQ (NMB 1812) (WO99/61620), OMP85—also known as D15—(NMB 0182) (WO00/23593), NspA (U52066) (WO96/29412), FhaC (NMB 0496 or NMB 1780), PorB (NMB 2039) (Mol. Biol. Evol. 12; 363-370, 1995), HpuB (NC_003116.1), TdfH (NMB 1497) (Microbiology 2001, 147; 1277-1290), OstA (NMB 0280), MltA also known as GNA33 and Lipo30 (NMB0033), HtrA (NMB 0532; WO 99/55872), HimD (NMB 1302), HisD (NMB 1581), GNA 1870 (NMB 1870), HlpA (NMB 1946), NMB 1124, NMB 1162, NMB 1220, NMB 1313, NMB 1953, HtrA, TbpA (NMB 0461) (WO92/03467) (see also above under iron acquisition proteins) and LbpA (NMB 1541).

OMP85

OMP85/D15 is an outer membrane protein having a signal sequence, a N-terminal surface-exposed domain and an integral membrane domain for attachment to the outer membrane. Immunogenic compositions of the invention may also comprise the full length OMP85, preferably as part of an OMV preparation. Fragments of OMP85 may also be used in immunogenic compositions of the invention, in particularly, the N terminal surface-exposed domain of OMP85 made up of amino acid residues 1-475 or 50-475 is preferably incorporated into a subunit component of the immunogenic compositions of the invention. The above sequence for the N terminal surface-exposed domain of OMP85 can be extended or truncated by up to 1, 3, 5, 7, 10, 15, 20, 25, or 30 amino acids at either or both N or C termini. It is preferred that the signal sequence is omitted from the OMP85 fragment.

OstA

OstA functions in the transport of lipopolysaccharides and may be considered to be a regulator of toxicity. OstA is optionally included in the toxin category where the toxin category is broadened to contain regulators of toxicity as well as toxins.

Preferably the subunit composition comprises a chimeric Imp/OstA protein of the present invention together with:

i) at least one further antigen selected from the following list: FhaB, passenger domain of Hsf, passenger domain of Hap, NadA, N-terminal surface exposed domain of OMP85, FrpA, FrpC, FrpA/C, TpbA, TbpB, LpbA, LbpB, PldA, PilQ, NspA and either or both of LPS immunotype L2 and LPS immunotype L3; and/or ii) at least a Neisserial (preferably meningococcal) outer membrane vesicle (OMV) preparation. Preferably the OMV preparation has at least one antigen (more preferably 2, 3, 4 or 5) selected from the following list which has been recombinantly upregulated in the outer membrane vesicle: FhaB, Hsf, NspA, NadA, PilC, Hap, MafA, MafB, Omp26, NMB0315, NMB0995, NMB1119, IgA protease, AspA, TbpA high, TbpA low, TbpB high, TbpB low, LbpA, LbpB, P2086, HpuA, HpuB, Lipo28, Sibp, FbpA, BfrA, BfrB, Bcp, NMB0964 and NMB0293

When i) is present the additional antigen is preferably selected from one or more of the groups of proteins given above.

In another embodiment the outer membrane vesicle of the present invention has at least one further antigen (more preferably 2, 3, 4 or 5) is recombinantly upregulated in the outer membrane vesicle and selected from the following list: NspA, Hsf, Hap, OMP85, TbpA (high), TbpA (low), LbpA, TbpB, LbpB, PilQ and PldA; and optionally comprising either or both of LPS immunotype L2 and LPS immunotype L3. This outer membrane vesicle may be used with one or more further outer membrane vesicles in which has at least one further antigen (more preferably 2, 3, 4 or 5) is recombinantly upregulated in the outer membrane vesicle and selected from the following list: FrpB, NspA, Hsf, Hap, OMP85, TbpA (high), TbpA (low), LbpA, TbpB, LbpB, PilQ and PldA; and optionally comprising either or both of LPS immunotype L2 and LPS immunotype L3.

The immunogenic compositions of the invention may comprise antigens (proteins, LPS and polysaccharides) derived from *Neisseria meningitidis* serogroups A, B, C, Y, W-135 or *Neisseria gonorrhoeae*.

Further Combinations

The pharmaceutical composition of the invention may further comprise bacterial capsular polysaccharides or oligosaccharides. The capsular polysaccharides or oligosaccharides may be derived from one or more of: *Neisseria meningitidis* serogroup A, C, Y, and/or W-135, *Haemophilus influenzae* b, *Streptococcus pneumoniae*, Group A Streptococci, Group B Streptococci, *Staphylococcus aureus* and *Staphylococcus epidermidis*.

A further aspect of the invention are vaccine combinations comprising the antigenic composition of the invention with other antigens which are advantageously used against certain disease states including those associated with viral or Gram positive bacteria.

In one preferred combination, the pharmaceutical compositions of the invention are formulated with 1, 2, 3 or preferably all 4 of the following meningococcal capsular polysaccharides or oligosaccharides which may be plain or conjugated to a protein carrier: A, C, Y or W-135. Preferably the immunogenic compositions of the invention are formulated with A and C; or C; or C and Y. Such a vaccine containing proteins from *N. meningitidis* serogroup B may be advantageously used as a global meningococcus vaccine.

In a further preferred embodiment, the pharmaceutical compositions of the invention, preferably formulated with 1, 2, 3 or all 4 of the plain or conjugated meningococcal capsular polysaccharides or oligosaccharides A, C, Y or W-135 (as described above), are formulated with a conjugated *H. influenzae* b capsular polysaccharide (or oligosaccharides), and/or one or more plain or conjugated pneumococcal capsular polysaccharides (or oligosaccharides) (for instance those described below). Optionally, the vaccine may also comprise one or more protein antigens that can protect a host against *Streptococcus pneumoniae* infection. Such a vaccine may be advantageously used as a global meningitis vaccine.

In a still further preferred embodiment, the pharmaceutical composition of the invention is formulated with capsular polysaccharides or oligosaccharides derived from one or more of *Neisseria meningitidis, Haemophilus influenzae* b, *Streptococcus pneumoniae*, Group A Streptococci, Group B Streptococci, *Staphylococcus aureus* or *Staphylococcus epidermidis*. The pneumococcal capsular polysaccharide or oligosaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). A further preferred embodiment would contain the PRP capsular polysaccharides or oligosaccharides of *Haemophilus influenzae*. A further preferred embodiment would contain the Type 5, Type 8 or 336 capsular polysaccharides of *Staphylococcus aureus*. A further preferred embodiment would contain the Type I, Type II or Type III capsular polysaccharides of *Staphylococcus epidermidis*. A further preferred embodiment would contain the Type Ia, Type Ic, Type II or Type III capsular polysaccharides of Group B *streptococcus*. A further preferred embodiment would contain the capsular polysaccharides of Group A *streptococcus*, preferably further comprising at least one M protein and more preferably multiple types of M protein.

Such capsular polysaccharides or oligosaccharides of the invention may be unconjugated or conjugated to a carrier protein such as tetanus toxoid, tetanus toxoid fragment C, diphtheria toxoid, CRM197, pneumolysin, Protein D (U.S. Pat. No. 6,342,224). The polysaccharide or oligosaccharide conjugate may be prepared by any known coupling technique. For example the polysaccharide can be coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508. A further method involves the coupling of a cyanogen bromide activated polysaccharide derivatised with adipic acid hydrazide (ADH) to the protein carrier by Carbodiimide condensation (Chu C. et al Infect. Immunity, 1983 245 256).

Preferred pneumococcal proteins antigens are those pneumococcal proteins which are exposed on the outer surface of the pneumococcus (capable of being recognised by a host's immune system during at least part of the life cycle of the pneumococcus), or are proteins which are secreted or released by the pneumococcus. Most preferably, the protein is a toxin, adhesin, 2-component signal tranducer, or lipoprotein of *Streptococcus pneumoniae*, or fragments thereof. Particularly preferred proteins include, but are not limited to: pneumolysin (preferably detoxified by chemical treatment or mutation) [Mitchell et al. Nucleic Acids Res. 1990 Jul. 11; 18(13): 4010 "Comparison of pneumolysin genes and proteins from *Streptococcus pneumoniae* types 1 and 2.", Mitchell et al. Biochim Biophys Acta 1989 Jan. 23; 1007(1): 67-72 "Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (U.S. Pat. No. 5,804,193—Briles et al.); PspC and transmembrane deletion variants thereof (WO 97/09994—Briles et al); PsaA and transmembrane deletion variants thereof (Berry & Paton, Infect Immun 1996 December; 64(12):5255-62 "Sequence heterogeneity of PsaA, a 37-kilodalton putative adhesin essential for virulence of *Streptococcus pneumoniae*"); pneumococcal choline binding proteins and transmembrane deletion variants thereof; CbpA and transmembrane deletion variants thereof (WO 97/41151; WO 99/51266); Glyceraldehyde-3-phosphate—dehydrogenase (Infect. Immun. 1996 64:3544); HSP70 (WO 96/40928); PcpA (Sanchez-Beato et al. FEMS Microbiol Lett 1998, 164: 207-14); M like protein, (EP 0837130) and adhesin 18627, (EP 0834568). Further preferred pneumococcal protein antigens are those disclosed in WO 98/18931, particularly those selected in WO 98/18930 and PCT/US99/30390.

The pharmaceutical composition/vaccine of the invention may also optionally comprise outer membrane vesicle preparations made from other Gram negative bacteria, for example *Moraxella catarrhalis* or *Haemophilus influenzae*.

Compositions, Kits and Administration

A vaccine is a composition comprising at least one antigen which is capable of generating an immune response when administered to a host. Preferably, such vaccines are capable of generating a protective immune response against Neisserial, preferably *Neisseria meningitidis* and/or *Neisseria gonorrhoeae* infection.

The invention also relates to compositions comprising a Gram negative bacterium, a chimeric protein or an outer membrane vesicle preparation discussed herein. Such compositions of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a protein of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

The pharmaceutical compositions of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a protein or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgement of the attending practitioner. Suitable dosages, however, are in the range of 0.1-100 µg/kg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

All references or patent applications cited within this patent specification are incorporated by reference herein.

Preferred features and embodiment of the present invention will now be described further with reference to the following non-limiting Examples:

EXAMPLE 1

General Methods

Bacterial Strains and Growth Conditions. *Neisseria meningitidis* (Nme) H44/76, a serotype B strain, came from our laboratory collection. The H44/76lpxA mutant (Steeghs et al 1998; Nature 392; 449-450) and the H44/76 derived strain HA3003, where lpxA expression is controlled by the tac promoter (Steeghs et al 2001; EMBO J. 24; 6937-6945), were generously provided by L. Steeghs and P. van der Ley (Netherlands Vaccine Institute (NVI), Bilthoven, The Netherlands). Nme was grown on GC agar (Becton Dickinson) plates containing Vitox (Oxoid) and antibiotics when appropriate (kanamycin 100 µg/ml, chloramphenicol 5 µg/ml) in candle jars at 37° C. Liquid cultures were grown in tryptic soy broth (TSB) in plastic flasks at 37° C. with shaking. For sialylation experiments, 80 µM cytidine 5' monophospho-N-acetyl neuraminic acid (CMP-NANA, Sigma) was added for 2 h to the medium of bacteria growing in mid-log phase. *E. coli* strains DH5 α or TOP10F' (Invitrogen) were used for routine cloning. *E. coli* was propagated on LB plates. Antibiotics were added in the following concentrations: kanamycin 50 µg/ml, chloramphenicol 25 µg/ml and erythromycin 200 µg/ml.

Gel Electrophoresis and Immunoblotting.

SDS-Polyacrylamide gel electrophoresis (SDS-PAGE) under denaturing or semi-native conditions and immunoblotting were performed as described (Voulhoux et al 2003 Science 299; 262-265). For LPS evaluation, samples were boiled in SDS-PAGE sample buffer and subsequently incubated with 0.5 mg/ml proteinase K at 55° C. for one hour. After boiling for 10 min, lysates were run on 16% Tricine-SDS-PAGE (Lesse et al, 1990, J. Immunol. Methods. 126; 109-117) and stained with silver (Tsai et al 1982, Anal. Biochem. 119; 115-119).

Neuraminidase Treatment.

One ml of bacteria grown to mid-log phase was pelleted and washed with buffer A (20 mM Na2HPO4/NaH2PO4, 150 mM NaCl, 5 mM MgCl2, 5 mM CaCl2, pH 6.0). Bacteria were resuspended in 0.5 ml buffer A and 0.2 U/ml neuraminidase (type V, *Clostridium perfringens,* Sigma N-2876) was added for 60 min at 37° C. Next, bacteria were pelleted and processed for Tricine-SDS-PAGE. Cell envelopes were diluted in buffer A and incubated with 0.2 µml neuraminidase for 60 min at 37° C.

Isolation of Cellular Fractions.

Cell envelopes were prepared as described (Voulhoux et al 2003 Science 299; 262-265). Inner and outer membranes were separated by isopycnic sucrose-gradient centrifugation according to Masson and Holbein (Masson and Holbein 1983, J. Bacteriol. 154; 728-736) or, alternatively, according to the procedure of Shell et al. (Shell et al 2002, Infect. Immun. 70; 3744-3751). Lactate dehydrogenase activity was measured directly in the sucrose-gradient fractions (Westphal and Jann 1965; Method. Carbohydr. Chem. 5; 83-91). Equal volumes of each fraction were precipitated with 7% trichloroacetic acid (TCA) and analysed for proteins by SDS-PAGE and for LPS by Tricine-SDS-PAGE. To obtain extracellular growth medium, bacteria were removed from suspensions by centrifugation (15 min 6000 g). The supernatant was spun for 2 h at 100.000 g. Proteins and LPS were precipitated from the supernatants with 7% TCA. The precipitates were collected by centrifugation at 20.000 g for 30 min followed by an acetone wash.

LPS Quantification.

The LPS content of cell envelopes was determined by 3-deoxy-D-manno-octulosonic acid (KDO) measurement as described (Van Alphen et al 1978; J. Bacteriol. 134; 1089-1098).

Antibodies.

Overexpression of the Imp protein in the cell envelope of H44/76 was achieved by growing the imp mutant carrying the plasmid pEN11-Imp with 1 mM isopropyl-β-D-thiogalactopyranoside (IPTG). These induced cells were used to prepare outer membrane vesicles (Fredriksen et al 1991, NIPH Annals 14, 67-79) that were injected into mice to raise antiserum. Next, specific anti-Imp antibodies were purified by adsorption of the sera to purified Imp protein. For that end, inclusion bodies from strain BL21 pET11a-Imp were purified (Dekker et al 1995; Eur. J. Biochem. 232; 214-219), dissolved in 20 mM Tris/HCl, 100 mM glycine, 6 M urea pH 8, electrophoresed in 8% SDS-PAGE gels and blotted onto nitrocellulose. The Imp protein was visualized on the blot using 0.25% Ponceau S (Acros Organics) in 1% acetic acid. A strip containing the Imp protein was cut from the blot and used to adsorb specific anti-Imp antibodies from the sera of the immunized mice. Bound antibodies were eluted by a 5 min wash with 0.2 M glycine pH 3.0 followed by neutralization with 1 M Tris pH 10.8. The eluted antibodies were used for the specific detection of Imp on blots. Mouse monoclonal anti-FbpA and anti-PorA (MN23G2.38) antibodies were gifts from B. Kuipers (NVI, Bilthoven, The Netherlands).

Analysis of PL composition

Cells grown overnight on plate were harvested and resuspended in TSB. After subsequent dilution in 5 ml TSB to an OD550 of 0.1, cells were labeled for 7 h with 2 μCi [1-14C] sodium acetate at 37° C. Phospholipids were isolated from 1.4 ml of culture (Bligh and Dyer, 1959 Can. J. Med. Sci 37; 911-917), separated by TLC, and plates (silica gel 60, 20×10 cm, Merck) were developed with chloroform/methanol/acetic acid at a ratio of 65:25:10 and subjected to autoradiography.

LPS and Phospholipid Isolation and Quantification

SDS-PAGE under denaturing conditions was performed as described (Voulhoux et al., 2003 Science 299; 262-265). For LPS analysis, samples were boiled in SDS-PAGE sample buffer and subsequently incubated with 0.5 mg/ml proteinase K at 55° C. for one hour. After boiling for 10 min, lysates were analyzed on 16% Tricine-SDS-PAGE (Lesse et al., 1990 J. Immunol. Methods 126; 109-117) and stained with silver (Tsai and Frasch, 1982 Anal. Biochem. 119; 115-119). Cell envelopes were isolated as described previously (Voulhoux et al., 2003 Science 299; 262-265). The LPS content of cell envelopes was determined by KDO measurement as described (van Alphen et al., 1978 J. Bacteriol. 134; 1089-1098). Cells were harvested from plate and washed with a buffer containing 0.238% free acid HEPES, 0.04% KCl, 0.85% NaCl, 0.01% MgCl2.6H2O, 0.09% anhydrous glucose, and 0.5 mM CaCl2, adjusted with NaOH to pH 7.4. Phospholipids were isolated as described (Bligh and Dyer, 1959 Can. J. Med. Sci 37; 911-917) and the amount was quantified by determining the phosphorus content (Rouser et al., 1970 Lipids 5; 494-496).

Electron Microscopy

Cells were harvested from plate and chemically fixed, embedded in gelatin and cryosectioned. Ultrathin sections were observed with a Technai 10 EM at 100 kV.

EXAMPLE 2

Imp is Not Essential in *N. meningitidis*

Figure 1:
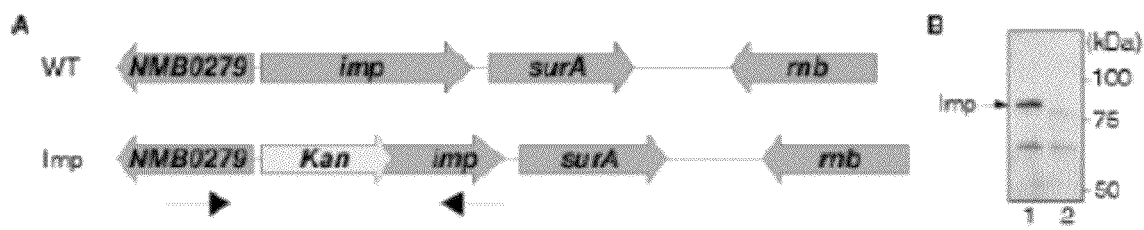
FIG. 1. Construction of an imp mutant strain. (A) Genomic organization of the imp locus in the wild-type (WT) and imp mutant. NMB0279 is annotated as a conserved hypothetical protein in the MC58 database (http://www.tigr.org). The surA gene (survival protein A) encodes a periplasmic chaperone involved in OMP biogenesis. mb: ribonuclease II. Arrows indicate the DNA region used for transformation. (B) Immunoblot of cell envelopes of wild-type (lane 1) and imp mutant (lane 2) separated on 8% SDS-PAGE and probed with anti-Imp antibodies. Molecular size markers are indicated in kDa.

A Neisserial imp mutant was constructed by allelic replacement of the imp gene in strain H44/76 with a copy containing a deletion-insertion mutation (FIG. 1A). We used the sequence of NMB0279 and NMB0280 from strain MC58 (http://www.tigr.org) to design primers to clone and subsequently delete the imp gene in Nme strain H44/76 (FIG. 1A). Briefly, part of the gene upstream of imp, NMB0279, was cloned from H44/76 DNA using primers A and B (Table 1). The 3' end of the imp gene was obtained by PCR with primers C and D. Both PCR products were cloned into pCR2.1-TOPO (Invitrogen), resulting in plasmids pCR2.1-NMB0279 and pCR2.1-3'Imp. An AccI-XbaI fragment of pCR2.1-NMB0279 was ligated into AccI-XbaI restricted pCR2.1-3'Imp. The resulting plasmid was cut with AccI to allow insertion of a kanamycin-resistance cassette. This cassette was PCR amplified from plasmid pACYC177 (New England Biolabs) using primers E and F (Table 1), which introduced terminal AccI sites and a Neisserial DNA uptake sequence.

The final construct, called pMB25, contained the kanamycin-resistance cassette in the same orientation as the transcription direction of the imp gene. Approximately 200 ng of a purified PCR product amplified from pMB25 with primers A and D was added to wild-type H44/76 bacteria growing in TSB plus 10 mM $MgCl_2$ for 6 h. Bacteria were plated on GC plates containing kanamycin. Transformants were screened by PCR using primer pairs AD, AF and DE. For complementation experiments, we cloned the imp gene from H44/76 genomic DNA by PCR using the primer pair D and G (Table 1).

Table 1. Oligonucleotides (primers) used in this study. Underlined sequences indicate restriction sites: AccI in primers B, C, E and F; NdeI in primers G and H, AatII in primer D and BamHI in primer I. Dashed line in primer F indicates the Neisserial DNA uptake sequence.

| | Sequence (5'-3') | Purpose |
|---|---|---|
| A | ATGCCTGCAACCTTCAAGTG, SEQ ID NO: 18 | 5' primer for cloning of NMB0279 |
| B | ATGTCGACAATCGCCCCTCAAGTCGGTTTG, SEQ ID NO: 19 | 3' primer for cloning of NMB0279 |
| C | ATGTCGACTACCTGCGGCCGGATTATGC, SEQ ID NO: 20 | 5' primer for cloning of 3' end of imp |
| D | ATGACGTCTCAGGGTCGTTTGTTGCGTCCGGC, SEQ ID NO: 21 | 3' primer for cloning of 3' end of imp |
| E | AGCGTCGACTTCAGACGGCCACGTTGTGTC, SEQ ID NO: 22 | 5' primer for cloning of Kan-cassette |
| F | AGCGTCGACGCTGAGGTCTGCCTCGTG, SEQ ID NO: 23 | 3' primer for cloning of Kan-cassette |
| G | ATCATATGGCTCGTTTATTTTCACTCAAACC, SEQ ID NO: 24 | 5' primer for cloning of complete imp gene into pEN11 |
| H | TGCATATGGATGCCGTTGCGGCGGAG, SEQ ID NO: 25 | 5' primer for cloning of imp into pET11a |
| I | TGGGATCCTCAGGGTCGTTTGTTGCGTCC, SEQ ID NO: 26 | 3' primer for cloning of imp into pET11a |

The PCR product was cloned in pCR2.1-TOPO, cut and ligated into pEN11 using NdeI and AatII restriction, resulting in plasmid pEN11-Imp. Plasmid pEN11, a *Neisseria*-replicative plasmid, is a derivative of RV2100, which contains the H44/76 omp85 gene behind a tandem lac promoter-operator (tac-lacUV5) sequence (Voulhoux et al 2003 Science 299; 262-265). In pEN11, the ATG initiation codon of the omp85 gene is replaced by an NdeI site to facilitate exchange of genes. The imp mutant was transformed with pEN11-Imp by coincubation of bacteria with plasmid for 6 h on plate (Voulhoux et al 2003 Science 299; 262-265). Transformants were selected on plates containing chloramphenicol and tested for the presence of pEN11-Imp and the chromosomal imp::kan allele by PCR. The H44/76 imp gene without its signal sequence was cloned in pET11a (Novagen) using primers H and I (Table 1). The resulting plasmid pET11a-Imp was introduced into *E. coli* strain BL21(DE3) (Novagen) to allow expression of the truncated imp gene from the T7 promoter present in pET11a.

Kanamycin-resistant transformants were tested by PCR for the absence of an intact copy of the imp gene and the presence of the imp::kan allele. Correct transformants were readily obtained, demonstrating that in contrast to *E. coli* (Braun & Silhavy 2002, Mol. Microbiol. 45; 1289-1302), imp is not an essential gene in Nme. The absence of the Imp protein in the mutants was confirmed by immunoblotting (FIG. 1B).

EXAMPLE 3

Phenotype of a Neisserial imp Mutant

Figure 2:
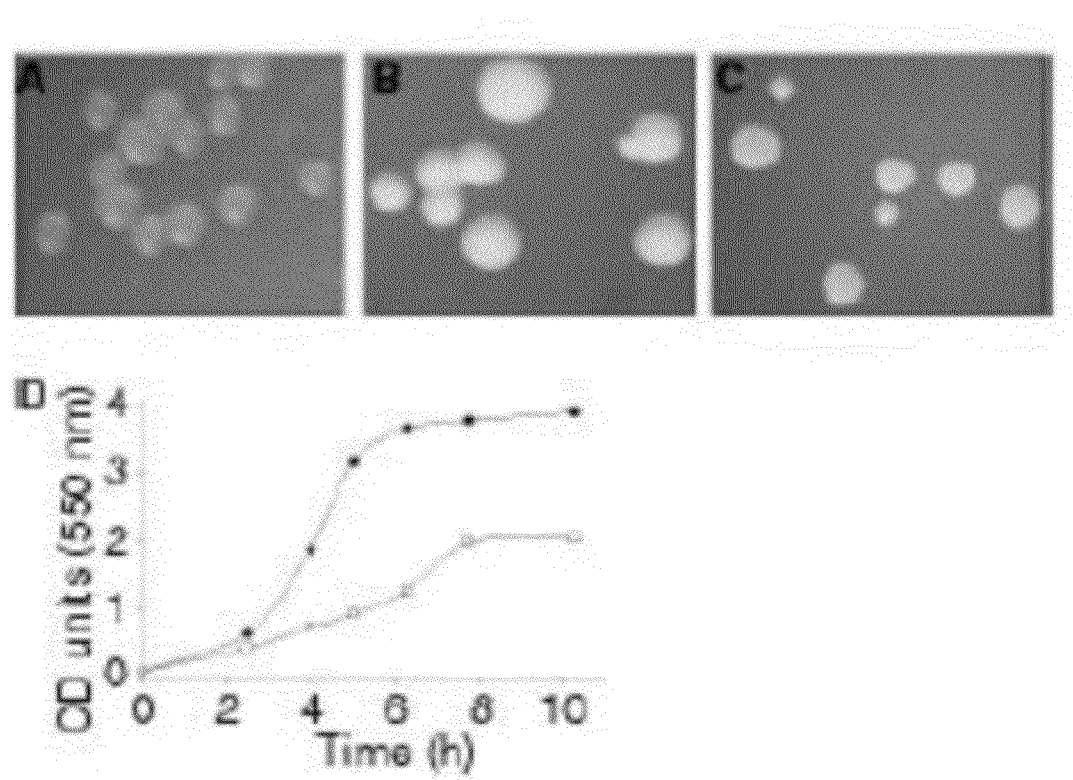
FIG. 2. Characteristics of an Nme imp mutant. (A-C) Colony morphology of wild-type (A), imp mutant (B) and lpxA mutant (C) bacteria. Colonies were observed with a binocular microscope using the shiny side of a flexible mirror. (D) Growth curve of wild-type (|) and imp mutant (.) bacteria in TSB.
Figure 3:
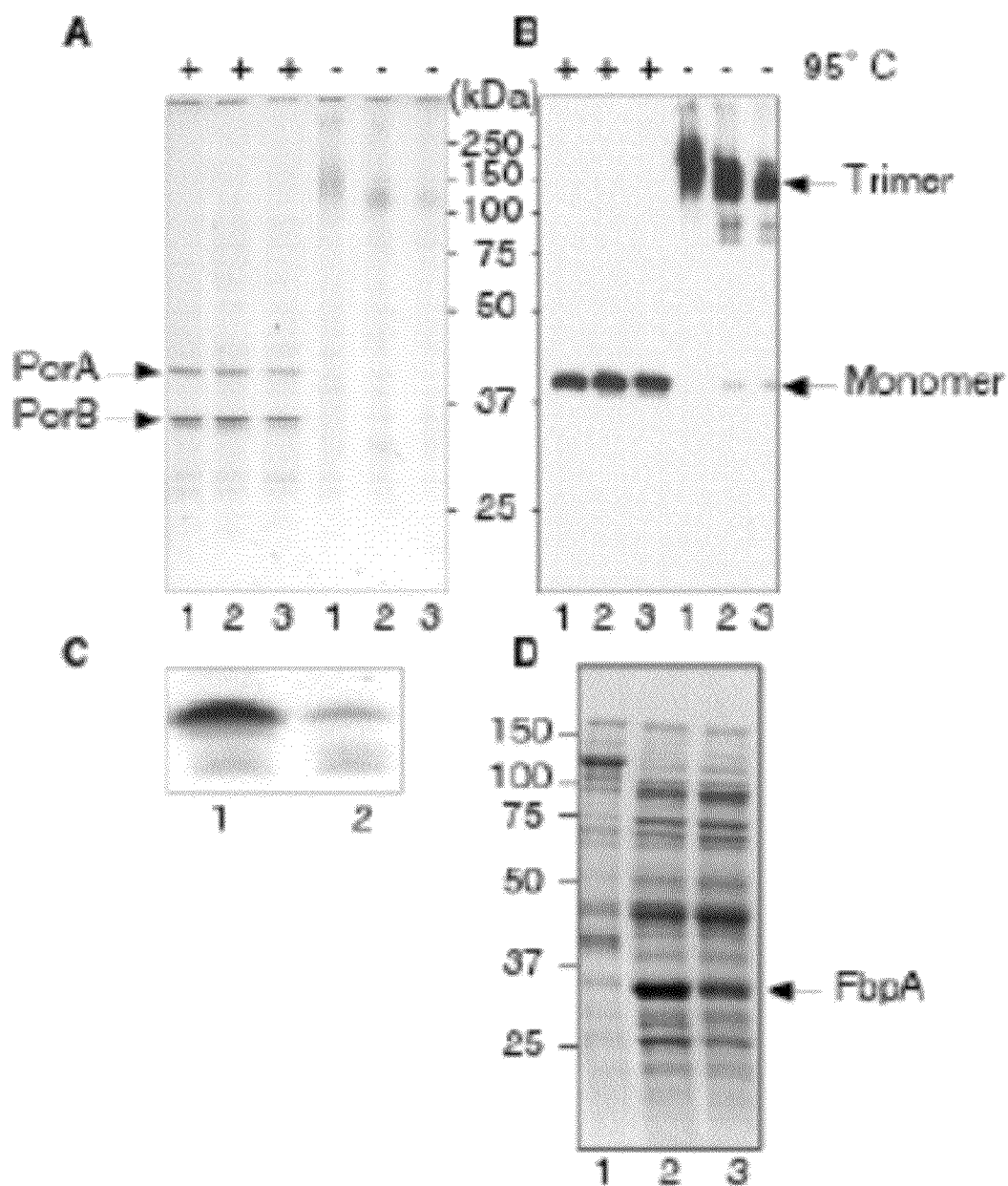
FIG. 3. Protein and LPS profiles of wild-type (lanes 1), imp mutant (lanes 2) and lpxA mutant (lanes 3) bacteria. (A, B) Cell envelopes were analysed by 10% SDS-PAGE in denaturing (95° C.+) or semi-native (95° C.−) conditions. Gels were stained with Coomassie blue (A) or blotted and probed with anti-PorA antibody (B). (C) Equal amounts of proteinase K-treated whole cell lysates were subjected to Tricine-SDS-PAGE and stained with silver to visualize LPS. (D) Equal volumes of extracellular growth media (100.000 g supernatant) were precipitated with TCA, subjected to 11% SDS-PAGE and stained with Coomassie blue. Molecular size markers (in kDa) are indicated.

A striking feature of the transformants was their intense colony opacity compared to wild-type colonies (FIG. 2A, B), a property also apparent for the LPS-deficient mutant (FIG. 2C). Furthermore, similar to the LPS-deficient strain (Steeghs et al 2001; EMBO J. 24; 6937-6945), the imp mutant bacteria grew slower and to a lower final optical density than wild-type bacteria (FIG. 2D). Analysis of the protein profiles of whole cell lysates (data not shown) or cell envelopes (FIG. 3A) in denaturing or semi-native SDS-PAGE showed no marked differences between wild-type and imp mutant bacteria. The major OMPs of Nme are the trimeric porins PorA and PorB. These trimers are very stable and do not dissociate into monomers during semi-native SDS-PAGE (Voulhoux et al 2003 Science 299; 262-265). When we analyzed cell envelopes of the imp mutant in semi-native conditions, most of the PorA protein was present in its trimeric form, as shown by immunoblotting (FIG. 3B). Only a small amount of monomeric porA was detected in the imp mutant analogous to the profile of the lpxA mutant (FIG. 3B) (Steeghs et al 2001; EMBO J. 24; 6937-6945). Thus, OMPs such as PorA and PorB are present in normal levels and are assembled correctly. In contrast, Tricine-SDS-PAGE analysis showed that the cellular LPS content was dramatically decreased in the imp mutant (FIG. 3C). Quantitative measurements of LPS, by determining the levels of KDO, an intrinsic component of the core region, confirmed this result: the imp mutant cell envelopes contained only 6.4 nmol KDO/mg protein, whereas wild-type levels were 95 nmol KDO/mg protein. The LPS of the imp mutant migrated at a similar position in the gel as wild-type LPS (FIG. 3C), indicative of similar sizes. The possibility that LPS was released by the imp mutant bacteria was investigated by analyzing extracellular growth media on Tricine SDS-PAGE. No enhanced release of LPS by the imp mutant bacteria was found (data not shown). In contrast, the wild-type and imp mutant showed very different extracellular protein profiles (FIG. 3D). The major protein present in the medium of the imp mutant was an approximately 35-kDa protein, which could be identified by immunoblotting as FbpA (data not shown), a periplasmic iron transporter (Ferreiros et al 1999. Comp. Biochem. Physiol. 123; 1-7). Similar high levels of FbpA were found in the extracellular medium of the lpxA mutant (FIG. 3D). These results indicate periplasmic leakage occurring in the imp and lpxA mutants, a phenomenon also reported for *E. coli* mutants expressing reduced amount of LPS (Nurminen et al 1997' Microbiology 143; 1533-1537). Complementation of the imp mutation by introduction of the imp gene on a plasmid under the control of an IPTG-regulatable promoter into the imp mutant resulted in complete restoration of all wild-type phenotypic traits described above in the presence of IPTG (data not shown), demonstrating that the imp mutant phenotype is directly related to Imp deficiency. Thus, the imp mutant demonstrates a similar phenotype as the lpxA mutant, indicative of a role of Imp in LPS biogenesis. In contrast to the lpxA mutant however, the imp mutant still produced a low amount of apparently full-length LPS. The presence of intact LPS molecules argues against a defect in LPS biosynthesis in the imp mutant. The low levels of LPS found may rather result from feedback inhibition on LPS synthesis by mislocalized LPS.

EXAMPLE 4

Localisation of LPS in Imp Mutant Strains by Membrane Separation

In order to localize the LPS produced by the imp mutant, we performed sucrose-gradient density centrifugation to separate inner and outer membranes. Despite many attempts using different protocols, we never obtained satisfactory membrane separations even of wild-type cells. As expected, the inner membrane marker, lactate dehydrogenase, fractionated to the lighter density fractions (FIG. 4A), whereas the OM porins fractionated mostly to the heavier fractions (FIG. 4B). However, LPS was found in almost every fraction of the gradient (FIG. 4C) and did not co-fractionate with the porins. Difficulties with Neisserial membrane separations were also appreciated previously (Masson & Holbein 1983, J. Bioteriol. 154; 728-736). The LPS of the imp mutant fractionated similarly in sucrose gradients as the LPS of the wild-type strain (data not shown), but because of the non-conclusive results with the wild-type membranes, we would not want to draw any conclusion from these results. Instead, we designed an alternative method to assess LPS localization in the imp mutant.

EXAMPLE 5

Surface Accessibility of LPS

Figure 5:
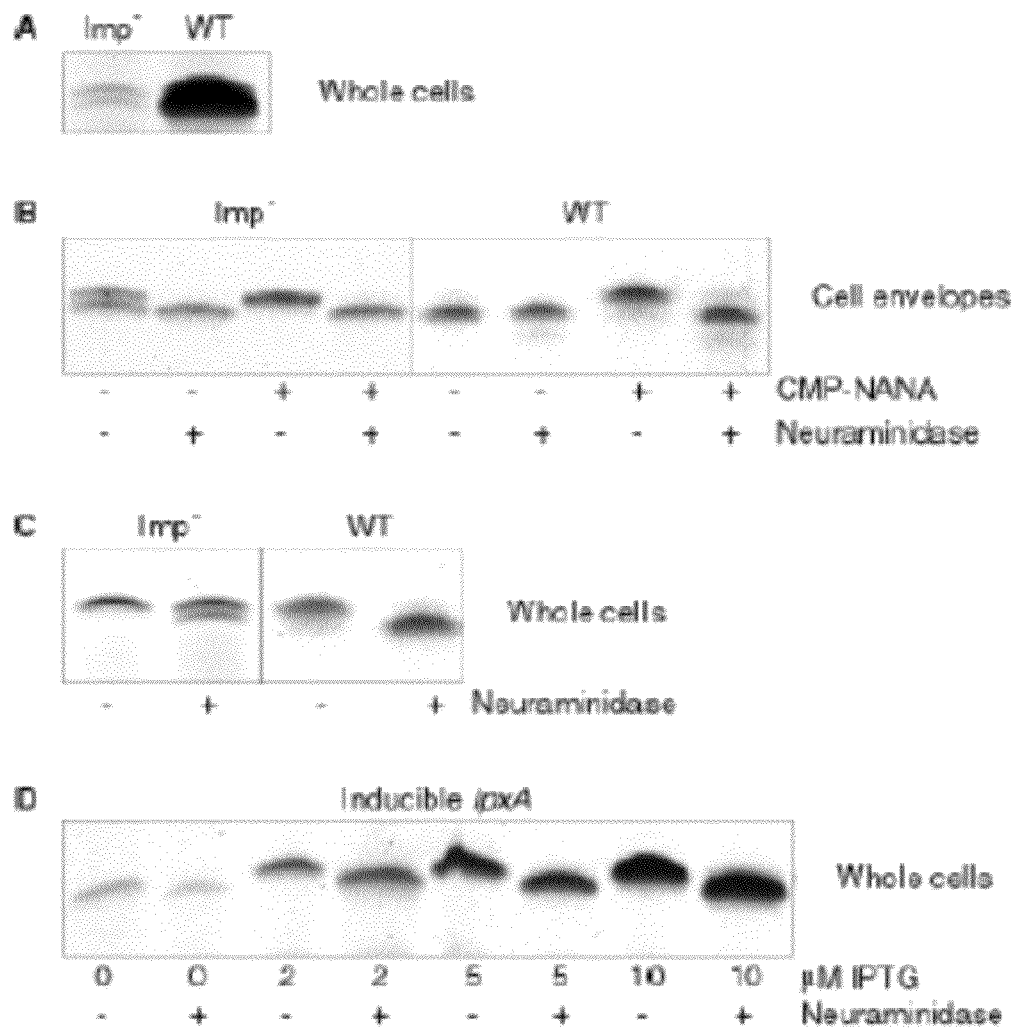
FIG. 5. Surface accessibility of LPS. All panels show silver-stained Tricine SDS-PAGE gels containing samples treated with proteinase K before loading. (A) Equal amounts of whole cell lysates of the indicated strains were loaded on the same gel. (B) Cell envelopes of bacteria grown the presence or absence of 80 µM CMP-NANA. Where indicated, the cell envelopes were treated with neuraminidase before electrophoresis. (C) Intact bacteria grown in the presence of 80 µM CMP-NANA were treated with neuraminidase and subsequently processed for Tricine-SDS-PAGE. In panels B and C five times as much material of the imp mutant samples was loaded compared to wild-type samples. Wild type and imp mutant samples were electrophoresed and stained on separate gels, to obtain optimal visibility of the LPS bands of both variants. (D) The inducible lpxA mutant was grown in the presence of the indicated IPTG concentrations plus 80 µM CMP-NANA. Intact cells were treated with neuraminidase as indicated. Equal amounts of cell lysates were run on the same gel.

Neisseriae do not synthesize O-antigen. The terminal oligosaccharide portion of the core of Neisserial LPS is variable due to phase-variable expression of the glycosyltransferases involved. Consequently, many different so-called LPS immunotypes exist. The L3 immunotype contains a lacto-N-neotetraose unit as terminal oligosaccharide of the α-chain, which can be further extended by a sialic acid residue. Meningococci are capable of sialylating the lacto-N-neotetraose unit by using endogeneously produced CMP-NANA as substrate donor or by utilizing this nucleotide sugar when added to the growth medium (Kahler & Stephens 1998, Crit. Rev. Microbiol. 24; 281-334). The sialic acid residue can be removed from LPS by treating intact bacteria with neuraminidase (Ram et al 1998, J. Exp. Med. 187; 743-752). We utilized this feature to assess the cell surface location of LPS. The results described so far were obtained with an Nme L8 immunotype that cannot be sialylated. To exploit the neuraminidase assay, we constructed an imp mutant in an L3 background. The phenotype of this mutant, in terms of colony opacity, growth characteristics, release of periplasmic protein (data not shown) and low LPS content (FIG. 5A), was identical to that of the L8 imp mutant. The LPS of the L3 imp mutant appeared in silver-stained Tricine-SDS-PAGE gels as two bands (FIG. 5A, B). After neuraminidase treatment of cell envelopes, all LPS migrated at the lower position (FIG. 5B), demonstrating that the higher band corresponds to sialylated LPS. After growth of the mutant in the presence of CMP-NANA, all LPS migrated at the higher position, and was completely converted to the lower migrating form upon neuraminidase treatment of cell envelopes (FIG. 5B). Thus, the L3 imp mutant produces LPS with a full-length α-chain which can be completely sialylated and subsequently be desialylated with neuraminidase. Wild-type bacteria produced sialylated LPS only when CMP-NANA was added to the growth medium (FIG. 5B); apparently the endogeneous CMP-NANA levels are rate-limiting when regular high levels of LPS are produced.

To test whether LPS was exposed at the cell surface, we treated intact bacteria grown in the presence of CMP-NANA with neuraminidase. Only a minor part of LPS was desialylated in the intact imp mutant cells, indicating that most of the LPS was not accessible to neuraminidase at the cell surface (FIG. 5C). The small amount of LPS that was accessible, possibly resulted from the leakiness of the mutant cells, as revealed by the enhanced protein release observed (FIG. 3D). In contrast, sialylated LPS present in wild-type cells was completely desialylated and thus fully exposed at the cell surface as expected (FIG. 5C). To address whether the difference in neuraminidase accessibility between wild-type and imp mutant bacteria was influenced in any way by the large difference in total LPS present, we performed similar assays in a strain where lpxA expression is regulatable with IPTG (Steeghs et al 2001; EMBO J. 24; 6937-6945). This strain was grown in the presence of CMP-NANA and various concentrations of IPTG. Expression of LPS was dependent on the IPTG concentration used, although we detected some LPS even in the absence of IPTG (FIG. 5D); apparently the IPTG-inducible promoter was not completely silent. Nevertheless, at all different cellular LPS levels, cell surface localization of LPS was evident as inferred from its full accessibility to neuraminidase in intact cells (FIG. 5D). These data further validate the assay used and therefore strengthen our conclusion that LPS is mostly absent from the cell surface in the imp mutant. Thus, Imp functions in LPS transport to the outer leaflet of the OM.

EXAMPLE 6

Imp Homologs in Other Bacteria

The sequence of the Nme MC58 imp gene NMB0280 (http://www.tigr.org) was used as a query to search microbial genomes for Imp homologues using BLAST. Molecules involved in the biogenesis of well-conserved structures such as LPS are likely highly conserved. This is indeed the case for the imp gene, since homologs can be found in most Gram-negative, but not in Gram-positive bacteria (Braun & Silhavy 2002, Mol. Microbiol. 45; 1289-1302). The absence of an imp homolog in some Gram-negative bacteria appears to correlate with the absence of LPS, since we were unable to find imp homologs in bacteria that posses an outer membrane, but lack LPS biosynthesis genes (Raetz et al 2002, Annu. Rev. Biochem. 71; 635-700), such as *Thermotoga maritima, Deinococcus radiodurans* and the spirochaetes *Borrelia burgdorfferi* and *Treponema pallidum*. This observation further reinforces the notion of Imp functioning as an LPS transporter.

EXAMPLE 7

Topology Model of Imp

Figure 6:
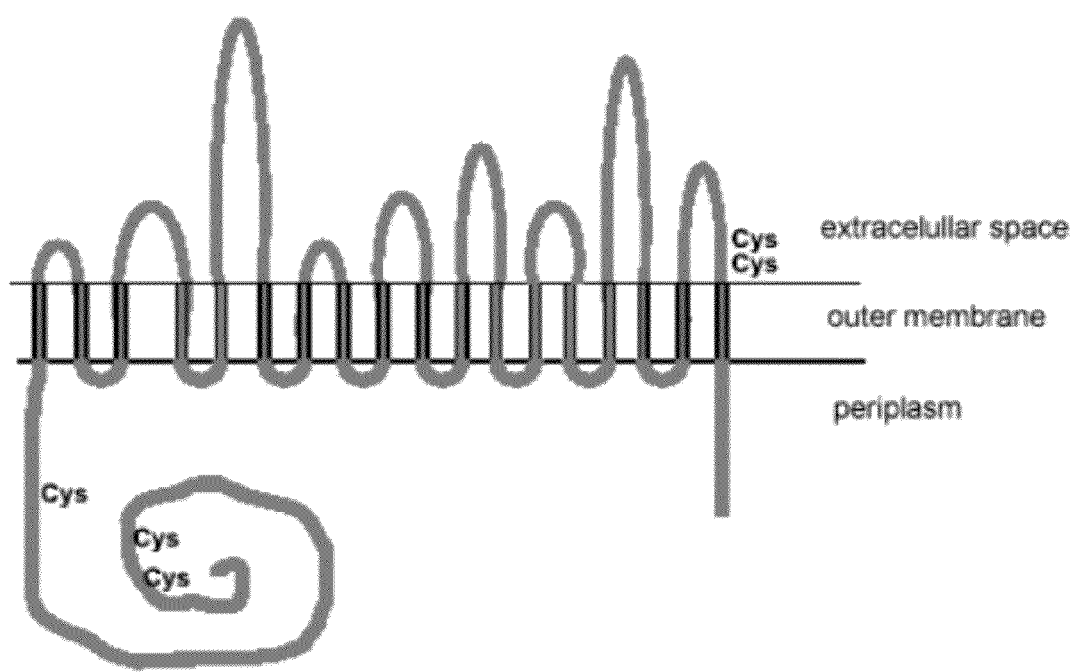
FIG. 6. Topology models of Neisserial Imp.

In order to understand the mechanism of Imp-mediated LPS transport, a topology model was made of Neisserial Imp. Our topology model predicts 18 transmembrane beta strands. With short periplasmic turns and some very long (60 amino acid residues) extracellular loops (FIG. 6A). The long loops are quite remarkable since they are very well conserved among Neisserial Imp proteins (FIG. 7).

Discussion

LPS is an essential component of the outer membrane of most Gram-negative bacteria and a causative agent of severe septic shock in humans. Its biogenesis has been studied for a long time, resulting in the identification of many proteins involved in its biosynthesis. However, the final step of LPS biogenesis, i.e. the transport of completed LPS molecules from the periplasmic leaflet of the IM to the bacterial cell surface has remained elusive. We have now identified for the first time a protein required for this LPS transport pathway. A Neisserial imp mutant produced drastically reduced amounts of full-length LPS. Although we were unable to determine exactly the cellular location of the limited amount of LPS that accumulated in the imp mutant, the neuraminidase accessibility assay clearly showed that the vast majority of this LPS was not accessible at the cell surface. Since Imp itself is an OMP, as shown by its presence in purified *E. coli* outer membranes and indicated by its high content of aromatic residues (Braun & Silhavy 2002, Mol. Microbiol. 45; 1289-1302) typical of β-barrel OMPs, Imp is likely the transporter that mediates the flip-flopping of LPS over the OM, although an additional role of Imp in transport through the periplasm cannot be excluded at this stage. The strongly decreased amounts of LPS in the imp mutant might be due to feed-back inhibition of LPS biosynthesis by mislocalized LPS.

Braun and Silhavy (Braun & Silhavy 2002, Mol. Microbiol. 45; 1289-1302) reported that depletion of Imp in a conditional *E. coli* mutant resulted in the appearance of novel, high-density membranes found in sucrose gradient fractionations. This higher density might result from an increased protein to lipid ratio. Consistently, whereas OMP assembly appeared unaffected by Imp depletion, both in *E. coli* (Braun & Silhavy 2002, Mol. Microbiol. 45; 1289-1302) and in Nme (this study), we demonstrated now that Imp depletion results in decreased levels of LPS in the OM, thus changing the protein:lipid ratio. Also, the observations that missense mutations in the *E. coli* imp gene resulted in increased sensitivity to hydrophobic agents (Sampson et al 1989 Genetics 122; 491-501: Alono et al 1994, Appl. Environ. Microbiol. 60; 4624-4626) can now be understood: these mutants likely suffered from reduced levels of LPS, a property known to affect the integrity of the OM (Nurminen et al 1997, Microbiology 143; 1533-1537).

Previously, another essential OMP, Omp85, has been suggested to be involved in LPS transport (Nurminen et al 1997, Microbiology 143; 1533-1537). However, we have demonstrated a strong OMP assembly defect in an Omp85-depleted strain (Voulhoux et al 2003 Science 299; 262-265). Thus, any effect of Omp85 depletion on LPS biogenesis might be a consequence of the misassembly of Imp. Furthermore, the demonstration of an interaction of Omp85 with non-native porin (Voulhoux et al 2003 Science 299; 262-265), the presence of an omp85 homolog in Gram-negative bacteria lacking LPS biosynthesis genes and the high conservation of Imp in Gram-negative bacteria, except in those that lack LPS-biosynthesis genes (this study), all argue for a direct role of Omp85 in OMP assembly and of Imp in LPS transport. With the identification of the functions of Omp85 and Imp, major progress in understanding the biogenesis of the bacterial outer membrane can now be made.

The Imp protein is an attractive target for the development of novel antibacterial substances, in light of its high conservation, cell surface localization and essential role in most Gram-negatives. Additionally, Neisserial imp mutant strains might be useful as vaccine strains. Neisserial vaccines consist of outer membrane vesicles that are treated with detergents to remove the majority of LPS in order to prevent toxic reactions in vaccinees. This procedure unfortunately removes also potentially important vaccine components such as cell-surface exposed lipoproteins. Vaccines prepared in this way contain approximately 7% of normal LPS levels (Fredriksen et al 1991, NIPH Annals 14, 67-79). Our data show that that is about the level of LPS left in the imp mutant. Thus, deletion of the imp gene in a vaccine strain relieves the need for detergent extraction and thereby the loss of potentially important vaccine components.

The Imp protein was named after the phenotype of the imp missense mutants (increased membrane permeability). We propose to change this name now that we have established the function of Imp. We suggest to name the gene IpxZ, in line with the Ipx designation used for LPS biogenesis genes and the Z to signify that the imp gene product mediates the final step in LPS biogenesis.

EXAMPLE 8

Construction of Plasmids and msbA-Mutant Strains

Figure 9:
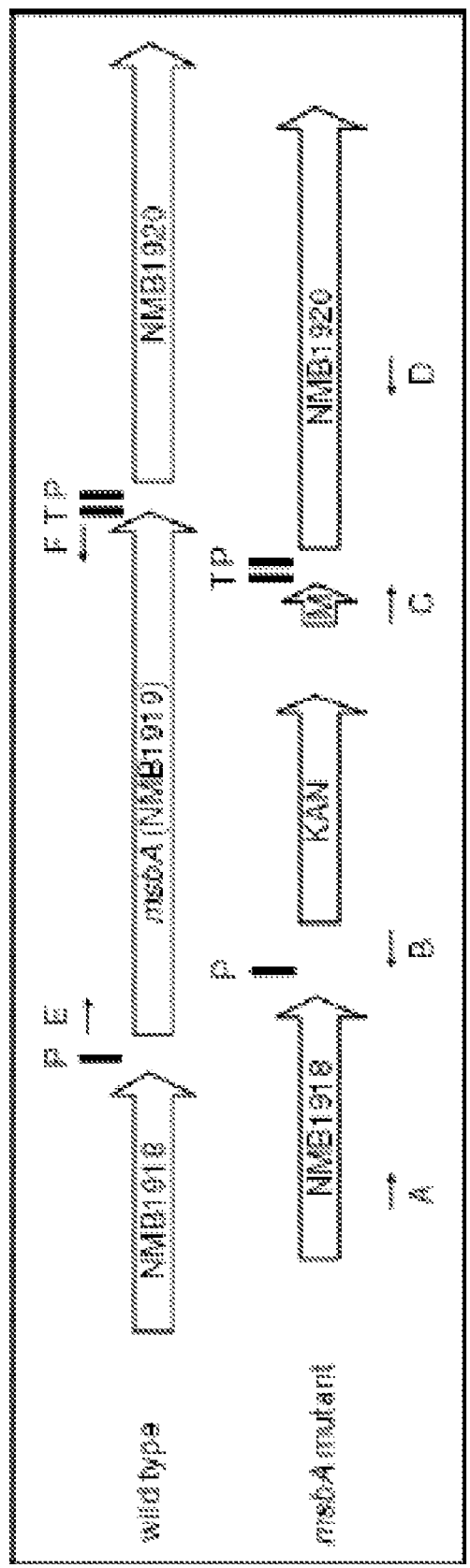
FIG. 9. Genetic organization of the msbA locus in the wild-type strain and the constructed msbA mutant.

To disrupt the msbA gene in *N. meningitidis*, we made use of the available genome sequence of strain MC58 (Tettelin et al., 2000 Science 287; 1809-1815) to design PCR primers (FIG. 9). Briefly, parts of the genes upstream and downstream of msbA, designated NMB1918 and NMB1920, respectively, were amplified by PCR from genomic DNA of H44/76 using Tad polymerase and primer pairs NB and C/D, respectively (FIG. 9). Both PCR products were cloned into pCRII-TOPO (Invitrogen), resulting in plasmids pCRIINMB1918 and pCRII-NMB1920, respectively. An AccI-KpnI fragment of pCRIINMB1918 was ligated into AccI-KpnI digested pCRII-NMB1920. The resulting plasmid was cut with AccI to allow for the insertion of a kanamycin-resistance cassette derived from pMB25 (Bos et al., 2004 Proc. Natl. Acad. Sci. USA). The final construct, called pBTmsbA:: kan, contained the kanamycin-resistance cassette in the same orientation as originally the msbA gene and was used as the template for amplification of the disruption fragment by PCR with primer pair ND (FIG. 9). Approximately 200 ng of this PCR product was added together with 5 mM MgCl2 to H44/76 or HB-1 bacteria that were subsequently grown on plate for 6 h. Hereafter; bacteria were transferred to plates containing kanamycin. The correct gene replacement in kanamycin-resistant transformants was confirmed by PCR using primer pair ND.

For complementation experiments, we cloned the msbA gene from H44/76 genomic DNA by PCR with primer pair E/F (FIG. 9) using the High Fidelity Kit (Roche) according to manufacturer's protocol. The PCR product was cloned into pCRII-TOPO, ligated into pEN11 (Bos et al., 2004) after NdeI and AatII restriction, resulting in plasmid pEN11-msbA. The msbA mutant derived from strain H44/76 was transformed with pEN11-msbA by coincubation of bacteria with plasmid and 5 mM MgCl2 for 6 h on plate. Transformants were selected on plates containing chloramphenicol and repeatedly restreaked on plates containing 100 µM isopropyl-β-D-thiogalactopyranoside before performing complementation experiments. All enzymes were provided by Fermentas, except where indicated otherwise.

EXAMPLE 9

MsbA is not essential for *N. meningitidis*

The genomes of *N. meningitidis* strains MC58 (Tettelin et al., 2000) and Z2491 (Parkhill et al., 2000 Nature 404; 502-506) were searched with the default search matrix of the tBlastn program (Altschul et al., 1997 Nucleic Acids Res. 25; 3389-3402) using the amino acid sequence of *E. coli* MsbA as a probe (http://www.ncbi.nlm.nih.gov/blast). The amino acid sequence of the putative MsbA protein encoded by the MC58 gene NMB1919 displayed 32% identity and 52% similarity to that of *E. coli* MsbA. A similar degree of homology (31% identity and 52% similarity, respectively) was found for the putative MsbA protein of Z2491. An msbA mutant was constructed by allelic replacement in *N. meningitidis* strain H44/76 (FIG. 9). Kanamycin-resistant transformants were analyzed by PCR to verify the absence of an intact copy of the msbA gene and the presence of the msbA::kan allele. Since correct transformants were obtained at high frequency, it appears that in *N. meningitidis*, in contrast to *E. coli* (Zhou et al., 1998 J. Biol. Chem. 273; 12466-12475), MsbA is not essential for Viability

EXAMPLE 10

LPS Content of the msbA Mutant

Proteinase K-treated cell lysates from approximately 2.107 cells (based upon the estimation that an optical density at 550 nm (OD550) of 1 represents 1.109 cells/ml) from both wild-type and msbA-mutant cells were analyzed by Tricine-SDS-PAGE (FIG. 10A). Whereas LPS could clearly be detected on the gels in the cell lysate from the wild-type strain, it was barely visible in the cell lysate of the msbA mutant strain (FIG. 10A). Apparently, the msbA mutation has a strong impact on LPS synthesis, possibly due to some feedback inhibition mechanism caused by LPS stalled in the transport pathway, as previously observed in the imp mutant (Bos et al., 2004 Proc. Natl. Acad. Sci. USA). To quantify the LPS content, we determined the amount of 3-deoxy-D-mannooctulosonic acid (KDO), a structural component typical for LPS, in wild-type and mutant cells. Cell envelopes of the msbA mutant cells contained an LPS to protein ratio of 7% when compared to wild-type cells and similar to that in the imp mutant (FIG. 10B). Since a putative transcriptional terminator is present immediately downstream of the msbA gene (FIG. 9), the decreased LPS content in the msbA mutant was expected to be a direct consequence of the inactivation of the msbA gene and not of any polar effects of the mutation on downstream located genes. This supposition was confirmed in a complementation experiment. When plasmid pEN11-msbA, carrying a wild-type msbA gene, was introduced into the msbA mutant, the LPS to protein ratio was restored to nearly wild-type levels (FIG. 10B).

EXAMPLE 11

Growth Characteristics

As described previously for the lpxA mutant (Steeghs et al., 1998 Nature 392; 449-450) and the imp mutant (Bos et al., 2004 Proc. Natl. Acad. Sci. USA), the generation time of the msbA null mutant was strongly reduced during exponential growth as compared to the wild type and the cultures did not reach the same final OD as those of the wild-type strain (FIG. 11). Additionally, after 16 h growth at 37° C. the colonies of the msbA mutant, like those of the lpxA and imp mutants (Bos et al., 2004 Proc. Natl. Acad. Sci. USA), were smaller than those of the wild type and they also had an opaque appearance, in contrast to those formed by the wild-type strain (data not shown). Interestingly, the colonies of the msbA mutant were heterogeneous, with either smooth-edged or lobated-edged colonies (data not shown). The ratio of these two types of colonies seemed to increase from ~1 to ~20 in favor of the latter when samples were taken at different points during exponential growth (data not shown). N. meningitidis cells grown in liquid culture undergo autolysis, several hours after entering the stationary growth phase as shown in FIG. 11. This is described as being a result of the activity of the OM phospholipase A (OMPLA) (submitted OMPLA paper M.P. Bos). In the case of the msbA mutant, autolysis was retarded (FIG. 11). The cells did eventually lyze, but only after prolonged incubation periods (data not shown), a phenotype which was also observed for the imp mutant (unpublished results). Possibly, OMPLA requires LPS for activity, as has been described previously for another OM enzyme, i.e. the protease OmpT of E. coli (Kramer et al., 2002 Eur. J. Biochem. 269; 1746-1752).

EXAMPLE 12

Electron Microscopy and Cell Envelope Protein Profile

To determine whether the msbA mutant cells still have a double membrane, we prepared ultrathin sections and examined them by electron microscopy (FIGS. 12A,B). Indeed, a double membrane was clearly visible indicating that both IM and OM were still present. Apparently, the msbA mutation did not prevent the formation of an outer membrane. Additionally, analysis of the cell envelope protein profiles indicated that the expression of the major OM proteins PorA and PorB is not compromised in the msbA mutant (FIG. 12C). These results are comparable to those obtained with the lpxA (Steeghs et al., 1998 Nature 392; 449-450) and imp (Bos et al., 2004 Proc. Natl. Acad. Sci. USA) mutants. In conclusion, it appears that the msbA mutant is still able to assemble an OM, suggesting that PL transport is not compromised in the msbA mutant.

EXAMPLE 13

Phospholipid Composition of the msbA Mutant

To investigate whether all major PL species were produced in the msbA mutant, cells were labeled with [14C] sodium acetate, and PL were extracted and analyzed by thin layer chromatography (TLC) (FIG. 13A). N. meningitidis was previously reported to produce large amounts of phosphatidyletanolamine (PE) and phosphatidylglycerol (PG), minor amounts of phosphatidic acid (PA) and trace amounts of cardiolipin (CL) (Rahman et al., 2000 Microbiology 146; 1901-1911). When the PL profile of the msbA mutant was compared with that of the wild-type strain, no drastic change in PE content was observed (FIG. 13A). However, the amount of PG relative to that of PA and CL, which run at the same position in the TLC system used here, seemed clearly decreased (FIG. 13A). The same characteristics were found for the imp mutant (data not shown). The lack of LPS in the OM of LPS biogenesis mutants must be compensated by other lipidic components to form an OM. To investigate whether the msbA mutant produced more PL than did wild-type cells, PL were extracted from cells grown on plate and quantified by phosphorus determination. The msbA mutant derived from wild-type strain H44/76, which possesses a capsule, showed no increase in the total amount of PL (data not shown). Strikingly, however, the msbA mutant of strain HB-1, which produces no capsule, showed a considerable ($p<0.06$) increase in the total amount of PL compared to its parental strain (FIG. 13B). Apparently, in this strain, increased PL levels compensate the lack of LPS, whereas in the msbA mutant of strain H44/76 the lack of LPS might by compensated by increased amounts of capsule, which is anchored via its lipid tail in the outer leaflet of the outer membrane.

EXAMPLE 14

Complementation of a Temperature-Sensitive msbA Mutant of E. coli

The results presented so far suggest that in N. meningitidis MsbA is required only for LPS transport, whereas in E. coli, MsbA has been reported to be required for transport of both LPS and PL (Zhou et al., 1998 J. Biol. Chem. 273; 12466-12475). This discrepancy could be explained by assuming that the two MsbA proteins have overlapping, but different functions. To test this possibility, we investigated whether N. meningitidis msbA can complement an E. coli msbA mutation. The growth of the E. coli K-12 temperature-sensitive msbA strain WD2 is arrested at 44° C. (Doerrler et al., 2001 J. Biol. Chem. 276; 11461-11464). When pEN11-msbA, containing the msbA gene of N. meningitidis, was introduced into WD2, growth was fully restored at 44° C. to wild-type levels (data not shown). Apparently, the Neisserial MsbA protein can functionally complement the E. coli MsbA.

Discussion

Based on the analysis of a temperature-sensitive msbA mutant of E. coli, MsbA has been suggested to be involved in both LPS and PL transport (Zhou et al., 1998 J. Biol. Chem. 273; 12466-12475). However, recent in vitro analysis indicated that, in contrast to several other integral IM proteins, MsbA reconstituted in proteoliposomes did not stimulate PL flip-flop (Kol et al., 2003 J. Biol. Chem. 278; 24586-24593). It was postulated that a subset of proteins, characterized by a small number of transmembrane helices, facilitate lipid translocation via the protein-lipid interface (Kol et al., 2004 Biochemistry 43; 2673-2681). These proteins could be involved in this process, because they display more dynamic behavior and engage in less stable protein-lipid interactions than larger membrane proteins (Kol et al., 2004 Biochemistry 43; 2673-2681). However, it remained a possibility that MsbA is required for the release of PL from the outer leaflet of the IM for subsequent transport through the periplasm to the OM. To investigate whether MsbA has a role in PL transport, we made use of the ability of N. meningitidis to survive without LPS. The expectation was that it would be impossible to generate an msbA mutant if the MsbA protein had an essential role in the transport of PL, whereas the gene would be dispensable if its product were involved in LPS transport only. We found that an msbA disruption mutant could be created, thereby excluding an essential role for MsbA in PL transport. The mutant showed drastically reduced LPS levels, consistent with a role for MsbA in LPS biogenesis. The reduced levels of LPS in the msbA mutant might be the result of feedback regulation on LPS synthesis by LPS molecules stalled in the transport pathway, similarly as previously reported for the imp mutant (Bos et al., 2004 Proc. Natl. Acad. Sci. USA). Although the growth rate was clearly affected by the msbA mutation, an OM was still present and the major OM protein profile was similar to that of the wild type. All the major PL were produced in the msbA mutant, although the amount of PG seemed somewhat decreased, whereas the total amount of PA and CL seemed somewhat increased. The change in the PL profile could be a response to the loss of LPS from the OM, as the imp mutant showed the same phenotype in this respect. In addition, in the msbA mutant derived from HB-1, which lacks a capsule, PL were overproduced in such amounts, that they could form the outer leaflet in the OM, thereby replacing LPS. Similarly, it has been shown previously in *E. coli* that mutations in the LPS biosynthesis genes, htrB (lpxL) (Karow et al., 1992 J. Bacteriol. 174; 7407-7418) and lpxC (Kloser et al., 1998 Mol. Microbiol. 27; 1003-1008) gave rise to higher PL levels. However, such an increase in PL content was not observed in the msbA mutant of the capsule-producing strain H44/76.

Previously, the impossibility to create an lpxA mutation in a *N. meningitidis* strain lacking capsule was reported (Steeghs et al., 2001 EMBO J. 20; 6937-6945). Possibly, the small amount of LPS still made in the msbA mutant allowed for the construction of an msbA mutant in this background, even if these LPS molecules were not correctly localized. Importantly, a low-copy vector containing the msbA gene of *N. meningitidis* could complement a temperature-sensitive msbA mutant of *E. coli*. Since *N. meningitidis* MsbA is involved in LPS transport only, this result suggests that MsbA of *E. coli* is not required for PL transport either. The accumulation of PL in the IM observed in such an *E. coli* mutant at the restrictive temperature (Doerrler et al., 2001 J. Biol. Chem. 276; 11461-11464) could then be explained as a secondary effect of the defective LPS transport.

The invention claimed is:

1. An outer membrane vesicle preparation from a Neisserial bacterium, wherein expression of the MsbA protein in said bacterium is functionally downregulated by disrupting the MsbA gene such that the level of lipopolysaccharide in the outer membrane is decreased compared to a wild-type Neisserial bacterium.

2. A pharmaceutical composition comprising the outer membrane vesicle preparation of claim 1 and a pharmaceutically acceptable carrier.

* * * * *

SEQUENCE LISTING

```
<160> NUMBER OF SEQ ID NOS: 30

<210> SEQ ID NO 1
<211> LENGTH: 802
<212> TYPE: PRT
<213> ORGANISM: Neisseria

<400> SEQUENCE: 1

Leu Ala Arg Leu Phe Ser Leu Lys Pro Leu Val Leu Ala Leu Gly Leu
1               5                   10                  15

Cys Phe Gly Thr His Cys Ala Ala Asp Ala Val Ala Ala Glu Glu
            20                  25                  30

Thr Asp Asn Pro Thr Ala Gly Glu Ser Val Arg Ser Val Ser Glu Pro
        35                  40                  45

Ile Gln Pro Thr Ser Leu Ser Leu Gly Ser Thr Cys Leu Phe Cys Ser
    50                  55                  60

Asn Glu Ser Gly Ser Pro Glu Arg Thr Glu Ala Ala Val Gln Gly Ser
65                  70                  75                  80

Gly Glu Ala Ser Ile Pro Glu Asp Tyr Thr Arg Ile Val Ala Asp Arg
                85                  90                  95

Met Glu Gly Gln Ser Gln Val Gln Val Arg Ala Glu Gly Asn Val Val
            100                 105                 110

Val Glu Arg Asn Arg Thr Thr Leu Asn Thr Asp Trp Ala Asp Tyr Asp
        115                 120                 125

Gln Ser Gly Asp Thr Val Thr Ala Gly Asp Arg Phe Ala Leu Gln Gln
    130                 135                 140

Asp Gly Thr Leu Ile Arg Gly Glu Thr Leu Thr Tyr Asn Leu Glu Gln
145                 150                 155                 160

Gln Thr Gly Glu Ala His Asn Val Arg Met Glu Ile Glu Gln Gly Gly
                165                 170                 175

Arg Arg Leu Gln Ser Val Ser Arg Thr Ala Glu Met Leu Gly Glu Gly
            180                 185                 190

His Tyr Lys Leu Thr Glu Thr Gln Phe Asn Thr Cys Ser Ala Gly Asp
        195                 200                 205

Ala Gly Trp Tyr Val Lys Ala Ala Ser Val Glu Ala Asp Arg Glu Lys
    210                 215                 220

Gly Ile Gly Val Ala Lys His Ala Ala Phe Val Phe Gly Gly Val Pro
225                 230                 235                 240

Ile Phe Tyr Thr Pro Trp Ala Asp Phe Pro Leu Asp Gly Asn Arg Lys
                245                 250                 255
```

```
Ser Gly Leu Leu Val Pro Ser Leu Ser Ala Gly Ser Asp Gly Val Ser
            260                 265                 270

Leu Ser Val Pro Tyr Tyr Phe Asn Leu Ala Pro Asn Leu Asp Ala Thr
        275                 280                 285

Phe Ala Pro Ser Val Ile Gly Glu Arg Gly Ala Val Phe Asp Gly Gln
290                 295                 300

Val Arg Tyr Leu Arg Pro Asp Tyr Ala Gly Gln Ser Asp Leu Thr Trp
305                 310                 315                 320

Leu Pro His Asp Lys Ser Gly Arg Asn Asn Arg Tyr Gln Ala Lys
                325                 330                 335

Trp Gln His Arg His Asp Ile Ser Asp Thr Leu Gln Ala Gly Val Asp
            340                 345                 350

Phe Asn Gln Val Ser Asp Ser Gly Tyr Tyr Arg Asp Phe Tyr Gly Asn
        355                 360                 365

Lys Glu Ile Ala Gly Asn Val Asn Leu Asn Arg Val Trp Leu Asp
370                 375                 380

Tyr Gly Gly Arg Ala Ala Gly Gly Ser Leu Asn Ala Gly Leu Ser Val
385                 390                 395                 400

Leu Lys Tyr Gln Thr Leu Ala Asn Gln Ser Gly Tyr Lys Asp Lys Pro
                405                 410                 415

Tyr Ala Leu Met Pro Arg Leu Ser Val Glu Trp Arg Lys Asn Thr Gly
            420                 425                 430

Arg Ala Gln Ile Gly Val Ser Ala Gln Phe Thr Arg Phe Ser His Asp
        435                 440                 445

Ser Arg Gln Asp Gly Ser Arg Leu Val Val Tyr Pro Asp Ile Lys Trp
    450                 455                 460

Asp Phe Ser Asn Ser Trp Gly Tyr Val Arg Pro Lys Leu Gly Leu His
465                 470                 475                 480

Ala Thr Tyr Tyr Ser Leu Asn Arg Phe Gly Ser Gln Glu Ala Arg Arg
                485                 490                 495

Val Ser Arg Thr Leu Pro Ile Val Asn Ile Asp Ser Gly Ala Thr Phe
            500                 505                 510

Glu Arg Asn Thr Arg Met Phe Gly Gly Glu Val Leu Gln Thr Leu Glu
        515                 520                 525

Pro Arg Leu Phe Tyr Asn Tyr Ile Pro Ala Lys Ser Gln Asn Asp Leu
    530                 535                 540

Pro Asn Phe Asp Ser Ser Glu Ser Ser Phe Gly Tyr Gly Gln Leu Phe
545                 550                 555                 560

Arg Glu Asn Leu Tyr Tyr Gly Asn Asp Arg Ile Asn Thr Ala Asn Ser
                565                 570                 575

Leu Ser Ala Ala Val Gln Ser Arg Ile Leu Asp Gly Ala Thr Gly Glu
            580                 585                 590

Glu Arg Phe Arg Ala Gly Ile Gly Gln Lys Phe Tyr Phe Lys Asp Asp
        595                 600                 605

Ala Val Met Leu Asp Gly Ser Val Gly Lys Lys Pro Arg Asn Arg Ser
    610                 615                 620

Asp Trp Val Ala Phe Ala Ser Gly Ser Ile Gly Ser Arg Phe Ile Leu
625                 630                 635                 640

Asp Ser Ser Ile His Tyr Asn Gln Asn Asp Lys Arg Ala Glu Asn Tyr
                645                 650                 655

Ala Val Gly Ala Ser Tyr Arg Pro Ala Gln Gly Lys Val Leu Asn Ala
            660                 665                 670

Arg Tyr Lys Tyr Gly Arg Asn Glu Lys Ile Tyr Leu Lys Ser Asp Gly
        675                 680                 685
```

```
Ser Tyr Phe Tyr Asp Lys Leu Ser Gln Leu Asp Leu Ser Ala Gln Trp
    690                 695                 700

Pro Leu Thr Arg Asn Leu Ser Ala Val Val Arg Tyr Asn Tyr Gly Phe
705                 710                 715                 720

Glu Ala Lys Lys Pro Ile Glu Val Leu Ala Gly Ala Glu Tyr Lys Ser
                725                 730                 735

Ser Cys Gly Cys Trp Gly Ala Gly Val Tyr Ala Gln Arg Tyr Val Thr
            740                 745                 750

Gly Glu Asn Thr Tyr Lys Asn Ala Val Phe Phe Ser Leu Gln Leu Lys
        755                 760                 765

Asp Leu Ser Ser Val Gly Arg Asn Pro Ala Asp Arg Met Asp Val Ala
770                 775                 780

Val Pro Gly Tyr Ile Thr Ala His Ser Leu Ser Ala Gly Arg Asn Lys
785                 790                 795                 800

Arg Pro

<210> SEQ ID NO 2
<211> LENGTH: 621
<212> TYPE: PRT
<213> ORGANISM: N. meningitidis

<400> SEQUENCE: 2

Met Ile Glu Lys Leu Thr Phe Gly Leu Phe Lys Lys Glu Asp Ala Arg
  1               5                  10                  15

Ser Phe Met Arg Leu Met Ala Tyr Val Arg Pro Tyr Lys Ile Arg Ile
             20                  25                  30

Val Ala Ala Leu Ile Ala Ile Phe Gly Val Ala Ala Thr Glu Ser Tyr
         35                  40                  45

Leu Ala Ala Phe Ile Ala Pro Leu Ile Asn His Gly Phe Ser Ala Pro
 50                  55                  60

Ala Ala Pro Pro Glu Leu Ser Ala Ala Gly Ile Ile Ser Thr Leu
 65                  70                  75                  80

Gln Asn Trp Arg Glu Gln Phe Thr Tyr Met Val Trp Gly Thr Glu Asn
             85                  90                  95

Lys Ile Trp Thr Val Pro Leu Phe Leu Ile Ile Leu Val Val Ile Arg
            100                 105                 110

Gly Ile Cys Arg Phe Thr Ser Thr Tyr Leu Met Thr Trp Val Ser Val
            115                 120                 125

Met Thr Ile Ser Lys Ile Arg Lys Asp Met Phe Ala Lys Met Leu Thr
130                 135                 140

Leu Ser Ser Arg Tyr His Gln Glu Thr Pro Ser Gly Thr Val Leu Met
145                 150                 155                 160

Asn Met Leu Asn Leu Thr Glu Gln Ser Val Ser Asn Ala Ser Asp Ile
                165                 170                 175

Phe Thr Val Leu Thr Arg Asp Thr Met Ile Val Thr Gly Leu Thr Ile
            180                 185                 190

Val Leu Leu Tyr Leu Asn Trp Gln Leu Ser Leu Ile Val Val Leu Met
        195                 200                 205

Phe Pro Leu Leu Ser Leu Leu Ser Arg Tyr Tyr Arg Asp Arg Leu Lys
    210                 215                 220

His Val Ile Ser Asp Ser Gln Lys Ser Ile Gly Thr Met Asn Asn Val
225                 230                 235                 240

Ile Ala Glu Thr His Gln Gly His Arg Val Val Lys Leu Phe Asn Gly
                245                 250                 255
```

```
Gln Ala Gln Ala Ala Asn Arg Phe Asp Ala Val Asn Arg Thr Ile Val
            260                 265                 270

Arg Leu Ser Lys Lys Ile Thr Gln Ala Thr Ala Ala His Ser Pro Phe
        275                 280                 285

Ser Glu Leu Ile Ala Ser Ile Ala Leu Ala Val Ile Phe Ile Ala
    290                 295                 300

Leu Trp Gln Ser Gln Asn Gly Tyr Thr Thr Ile Gly Glu Phe Met Ala
305                 310                 315                 320

Phe Ile Val Ala Met Leu Gln Met Tyr Ala Pro Ile Lys Ser Leu Ala
                325                 330                 335

Asn Ile Ser Ile Pro Met Gln Thr Met Phe Leu Ala Ala Asp Gly Val
            340                 345                 350

Cys Ala Phe Leu Asp Thr Pro Pro Glu Gln Asp Lys Gly Thr Leu Ala
        355                 360                 365

Pro Gln Arg Val Glu Gly Arg Ile Ser Phe Arg Asn Val Asp Val Glu
    370                 375                 380

Tyr Arg Ser Asp Gly Ile Lys Ala Leu Asp Asn Phe Asn Leu Asp Ile
385                 390                 395                 400

Arg Gln Gly Glu Arg Val Ala Leu Val Gly Arg Ser Gly Ser Gly Lys
                405                 410                 415

Ser Thr Val Val Asn Leu Leu Pro Arg Phe Val Glu Pro Ser Ala Gly
            420                 425                 430

Asn Ile Cys Ile Asp Gly Ile Asp Ile Ala Asp Ile Lys Leu Asp Cys
        435                 440                 445

Leu Arg Ala Gln Phe Ala Leu Val Ser Gln Asp Val Phe Leu Phe Asp
    450                 455                 460

Asp Thr Leu Phe Glu Asn Val Arg Tyr Ser Arg Pro Asp Ala Gly Glu
465                 470                 475                 480

Ala Glu Val Leu Phe Ala Leu Gln Thr Ala Asn Leu Gln Ser Leu Ile
                485                 490                 495

Asp Ser Ser Pro Leu Gly Leu His Gln Pro Ile Gly Ser Asn Gly Ser
            500                 505                 510

Asn Leu Ser Gly Gly Gln Arg Gln Arg Val Ala Ile Ala Arg Ala Ile
        515                 520                 525

Leu Lys Asp Ala Pro Ile Leu Leu Leu Asp Glu Ala Thr Ser Ala Leu
    530                 535                 540

Asp Asn Glu Ser Glu Arg Leu Val Gln Gln Ala Leu Glu Arg Leu Met
545                 550                 555                 560

Glu Asn Arg Thr Gly Ile Ile Val Ala His Arg Leu Thr Thr Ile Glu
                565                 570                 575

Gly Ala Asp Arg Ile Ile Val Met Asp Asp Gly Lys Ile Ile Glu Gln
            580                 585                 590

Gly Thr His Glu Gln Leu Met Ser Gln Asn Gly Tyr Tyr Thr Met Leu
        595                 600                 605

Arg Asn Ile Ser Asn Lys Asp Ala Ala Val Arg Thr Ala
    610                 615                 620

<210> SEQ ID NO 3
<211> LENGTH: 1866
<212> TYPE: DNA
<213> ORGANISM: N. meningitidis

<400> SEQUENCE: 3
atgatagaaa aactgacttt cggactgttt aaaaaagaag acgcgcgcag ctttatgcgc      60
ctgatggcgt acgtccgccc ctacaaaatc cgcatcgttg ccgccctgat tgccattttc     120
```

-continued

```
ggcgttgccg ccaccgaaag ctaccttgcc gccttcatcg cccccctgat taaccacggc    180
ttttccgcac ctgccgcgcc gcccgagctg tctgccgccg ccggcatcat ttccaccctg    240
caaaactggc gcgaacagtt tacctatatg gtttgggggga cggaaaacaa aatctggacc    300
gtcccgctct tcctcatcat cctcgtcgtc atccgtggca tctgccgctt taccagcacc    360
tatctgatga cttgggtctc cgtgatgacc atcagcaaaa tccgcaaaga tatgtttgcc    420
aaaatgctga ccctttcctc ccgctaccat caggaaacgc cgtccggcac cgtactgatg    480
aatatgctca acctgaccga acagtcggtc agcaacgcca cgacatctt caccgtcctc    540 acgcgcgaca cgatgatcgt taccggcctg accatcgtcc tgctttacct caactggcag    600
ctcagcctca tcgtcgtcct gatgttcccc ctgctctccc tgctctcgcg ctactaccgc    660
gaccgtctga acacgtcat ttccgactcg caaaaaagca taggcacgat gaacaacgtg    720
attgccgaaa cccatcaggg acaccgcgtc gtcaagctgt tcaacgggca ggcgcaggcg    780
gcaaaccggt tcgacgcggt caaccgcacc atcgtccgcc tcagcaaaaa aatcacgcag    840
gcaacggcgg cacattcccc gttcagcgaa ctgatcgcct cgatcgccct cgccgtcgtc    900
atcttcatcg ccctgtggca aagccaaaac ggctacacca ccatcggcga atttatggca    960
ttcatcgtcg cgatgctgca aatgtacgcc cccatcaaaa gccttgccaa catcagcatc   1020
cctatgcaga cgatgttcct cgccgccgac ggtgtatgtg catttctcga caccccgccc   1080
gaacaggaca agggcacgct cgcaccgcag cgtgtcgaag ggcgcatcag cttccgcaac   1140
gtcgatgtcg aataccgttc agacggcatc aaagccctcg acaacttcaa cctcgacatc   1200
agacaaggcg aacgcgtcgc cctggtcgga cgttccggca gcggcaaatc caccgtcgtc   1260
aacctgctgc cccgctttgt cgaaccgtct gccggcaaca tctgcataga cggtatcgac   1320
atcgccgaca tcaaactcga ctgcctgcgc gcccaattcg ccctcgtctc ccaagacgta   1380
ttcctgtttg acgacaccct gtttgaaaac gtccgataca gccgtcccga cgcgggcgaa   1440
gccgaagtcc tgttcgccct ccaaaccgcc aacctgcaaa gcctgattga cagctccccg   1500
ctcggactgc accagcccat cggatcgaac ggcagcaact tatccggcgg acagcggcaa   1560
cgcgtcgcca ttgcccgcgc cattttgaaa gacgcgccga tattattatt ggacgaagcc   1620
accagcgcat tagacaacga atccgaacgc ctcgtccaac aggcgctcga acgcctgatg   1680
gaaaaccgca ccggcatcat cgtcgcccac cgcctgacca ccatcgaagg ggccgaccgc   1740
atcatcgtga tggacgacgg caaaatcatc gaacaaggca cacacgaaca actgatgtcc   1800
caaaacggtt actacacgat gttacgcaat atctcaaaca aagatgccgc cgtccggacg   1860
gcataa                                                              1866
```

<210> SEQ ID NO 4
<211> LENGTH: 623
<212> TYPE: PRT
<213> ORGANISM: B. parapertussis

<400> SEQUENCE: 4

Met Leu Ala Trp Arg Pro Gly Arg Pro Asp Gly Cys Gln Ala Ala Gly
 1               5                  10                  15

Gly Arg Arg Tyr Asn Pro Gly His Asp Cys Ile Lys Ala Ser Val Ser
             20                  25                  30

Leu Asn Ser Ala Ala Arg Asn Ala Pro Ala Gly Ser Gln Pro Val Lys
         35                  40                  45

Ala Glu Leu Trp Lys Arg Val Tyr Ser Arg Val Gly Ser Tyr Trp Lys
     50                  55                  60

-continued

Gly Leu Val Leu Ala Val Leu Met Ala Gly Ala Ala Thr Gln
65                  70                  75                  80

Pro Thr Leu Ala Val Ile Met Lys Pro Leu Leu Asp Asp Gly Phe Ser
                85                  90                  95

Gly Ala Lys Pro His Tyr Val Trp Phe Leu Pro Leu Ala Val Val Gly
            100                 105                 110

Leu Ile Leu Leu Arg Gly Ile Cys Asn Phe Phe Ser Asp Tyr Leu Leu
        115                 120                 125

Ala Trp Val Ala Asn Asn Val Leu Arg Gly Ile Arg Gly Glu Met Phe
    130                 135                 140

Glu Arg Leu Leu Gly Leu Pro Asp Ala Asp Phe Lys Arg Gly Asp Thr
145                 150                 155                 160

Gly Arg Leu Leu Asn Arg Phe Thr Ile Asp Ala Gly Asn Val Thr Gly
                165                 170                 175

Tyr Ala Thr Asp Val Ile Thr Val Leu Val Arg Glu Thr Leu Val Val
            180                 185                 190

Ile Ala Leu Ile Gly Val Leu Leu Tyr Met Ser Trp Ala Leu Thr Leu
        195                 200                 205

Ile Ile Leu Val Met Leu Pro Val Ser Val Gly Ile Ala Arg Ala Phe
    210                 215                 220

Thr Arg Arg Leu Arg Arg Ile Asn Arg Glu Thr Val Asn Met Asn Ala
225                 230                 235                 240

Glu Leu Thr Arg Val Val Ser Glu Gly Ile Asp Gly Gln Arg Val Ile
                245                 250                 255

Lys Leu Phe Asp Gly Tyr Asp Ala Glu Arg Arg Arg Phe Asp Phe Val
            260                 265                 270

Asn Ser Arg Leu Arg Arg Phe Ala Met Arg Ser Ala Thr Ala Asp Ala
        275                 280                 285

Ala Leu Thr Pro Leu Thr Gln Val Cys Ile Ser Val Ala Val Gly Ala
    290                 295                 300

Val Ile Ala Val Ala Leu Ser Gln Ala Asn Ser Gly Ala Leu Thr Val
305                 310                 315                 320

Gly Ser Phe Ala Ser Phe Met Ala Ala Leu Ala Gln Ile Phe Asp Pro
                325                 330                 335

Ile Lys Arg Leu Thr Asn Leu Ala Gly Lys Met Gln Lys Met Leu Val
            340                 345                 350

Ala Ala Glu Ser Val Phe Thr Leu Val Asp Gln Thr Pro Glu Ala Asp
        355                 360                 365

Ala Gly Thr Arg Ala Leu Pro Glu Pro Val Arg Gly Lys Val Glu Phe
    370                 375                 380

Arg Ala Val Ser His Arg Phe Pro Asp Ala Asp Arg Asp Thr Val Ser
385                 390                 395                 400

Ala Val Ser Phe Leu Val Glu Pro Gly Gln Thr Val Ala Leu Val Gly
                405                 410                 415

Arg Ser Gly Ser Gly Lys Thr Thr Leu Val Asn Met Leu Pro Arg Phe
            420                 425                 430

Val Leu Pro Asp Gly Gly Asp Ile Leu Phe Asp Asp Val Pro Ile Gln
        435                 440                 445

Asp Leu Thr Leu Arg Ser Leu Arg Ser His Leu Ser Leu Val Ser Gln
    450                 455                 460

Asp Val Val Leu Phe Asp Asp Thr Ile Ala Ala Asn Val Gly Tyr Gly
465                 470                 475                 480

Ala Gly Gly Thr Val Asp Asp Ala Arg Val Arg Asp Ala Leu Ala Ala

```
                        485                 490                 495
Ala Asn Leu Leu Glu Phe Val Asp Gly Leu Pro Leu Gly Ile His Thr
                500                 505                 510

Pro Val Gly Gln Asn Ala Ala Arg Leu Ser Gly Gly Gln Arg Gln Arg
            515                 520                 525

Leu Ala Ile Ala Arg Ala Leu Ile Lys Asn Ala Pro Val Leu Ile Leu
        530                 535                 540

Asp Glu Ala Thr Ser Ala Leu Asp Asn Glu Ser Glu Arg Gln Val Gln
545                 550                 555                 560

Ala Ser Leu Glu Arg Leu Met Arg Gly Arg Thr Thr Leu Val Ile Ala
                565                 570                 575

His Arg Leu Ser Thr Val Gln Asn Ala Asp Arg Ile Ile Val Leu Asp
                580                 585                 590

Ala Gly Lys Ile Val Glu His Gly Pro His Ser Glu Leu Leu Ala Ala
            595                 600                 605

Asn Gly Leu Tyr Ala Ser Leu Tyr Asn Met Gln Phe Arg Glu Asp
        610                 615                 620

<210> SEQ ID NO 5
<211> LENGTH: 1872
<212> TYPE: DNA
<213> ORGANISM: B. pertussis

<400> SEQUENCE: 5
atgctggcgt ggcggccggg tcggccggac ggttgtcagg cggcgggtgg ccgacggtac      60
aatcccgggc acgattgtat taaagcgagt gtttccttga attctgccgc acgcaatgcg     120
cccgccggct cccagccggt caaggccgaa ctctggaagc gggtctacag ccgcgtaggc     180
tcttactgga aggggctggt gctggccgtc ctgctgatgg ccggcgccgc cgcgacccag     240
cccacgctgg cagtcatcat gaagccgctg ctcgacgatg gcttctcggg cgccaagccg     300
cattatgtct ggttcctgcc gctggcggtg gtggggctga tcctgctgcg cggaatctgc     360
aatttcttca gcgactacct gctggcctgg gtggccaaca acgtgctgcg cggcatccgg     420
ggcgagatgt tcgagcggct gctgggcctg cccgatgccg acttcaagcg cggcgacacc     480
ggccgcctgc tcaaccgctt caccatcgac gcgggcaacg tcaccggcta cgccaccgac     540
gtcatcacgg tgctggtgcg cgaaaccctg gtcgtcatcg ccctgatcgg cgtgctgctg     600
tacatgtcgt gggcgctgac gctgatcatc ctcgtcatgc tgccggtgtc ggtgggcatc     660
gcccgcgcct tcacgcgccg gctgccgccg atcaaccgcg aaaccgtcaa catgaacgcc     720
gagctcaccc gcgtggtcag cgagggcatc gacgggcagc gtgtcatcaa gctgttcgac     780
ggctatgacg ccgagcgccg ccgtttcgac ttcgtcaact cgcgcctgcg ccgcttcgcg     840
atgcgcagcg ccaccgccga cgcggcgctc acgccgctca cgcaggtgtg catctcggtc     900
gccgtgggcg cggtcatcgc cgtggccctc agccaggcca acagcggcgc gctcaccgtc     960
ggcagcttcg cctcgttcat ggccgcgctg gcgcagatct tcgatccgat caagcgcctg    1020
accaacctgg ccggcaaaat gcagaaaatg ctggtggccg ccgaaagcgt gttcaccctg    1080
gtggaccaga cgcccgaggc cgacgccggc acgcgcgcct gcccgaacc ggtgcgcggc    1140 aaggtcgaat ccgtgcggt cagccatcgc ttccccgacg ccgatcgcga taccgtcagc    1200
gccgtgtcgt tcctggtcga gccgggccag accgtgcccc tggtcggacg ctcgggcagc    1260
ggcaagacca ctctggtcaa catgctgccg cgctttgtcc tgcccgatgg cggcgacatc    1320
ctgttcgacg atgtgcccat ccaggatctc accttgcgca gcctgcgctc gcatctgtcg    1380
```

-continued

```
ctggtcagcc aggacgtggt gctgttcgac gacaccattg ccgccaacgt gggttatggc    1440
gccggcggca ccgtcgacga cgcgcgcgtt cgcgacgcgc tggccgcggc caacctgctg    1500
gagttcgtcg acggcttgcc gctgggcatc cacacgccgg tgggccagaa tgccgcccgc    1560
ctgtcgggcg ccagcgcca gcgcctggcg atcgcccgcg ccctgatcaa gaacgcgccc    1620
gtcctgatcc tcgacgaggc gacctcggcg ctggacaacg aatccgagcg ccaggtgcag    1680
gcatcgctgg agcggctgat gcgcgggcgc accacgctgg tcatcgccca ccggctgtcc    1740
accgtgcaga acgccgaccg catcatcgtg ctggacgccg gcaagatcgt cgagcacggg    1800
ccgcacagcg agctgttggc cgccaacggc ctgtacgcct cgctctacaa catgcagttc    1860
cgcgaggact ga                                                       1872
```

```
<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cccaaagcga agtggtcgaa                                                20

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gtcgactatc ggtagggcgg gaactg                                         26

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gtcgacgacc gcatcatcgt gatgga                                         26

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ttcgtcgctg ccgacctgtt                                                20

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
ttcatatgat agaaaaactg actttcgg                                       28

<210> SEQ ID NO 11
```

```
<211> LENGTH: 27
<212> TYPE: DNA
<213> ORGANISM: Artificial Sequence
<220> FEATURE:
<223> OTHER INFORMATION: Primer

<400> SEQUENCE: 11
gacgtcccat tcggacggc attttgt                                        27

<210> SEQ ID NO 12
<211> LENGTH: 31
<212> TYPE: PRT
<213> ORGANISM: Neisseria

<400> SEQUENCE: 12

Arg His Ala Asn Val Gly Arg Asn Ala Phe Glu Leu Phe Leu Ile Gly
1               5                   10                  15

Ser Gly Ser Asp Gln Ala Lys Gly Thr Asp Pro Leu Lys Asn His
            20                  25                  30

<210> SEQ ID NO 13
<211> LENGTH: 29
<212> TYPE: PRT
<213> ORGANISM: Neisseria

<400> SEQUENCE: 13

Lys Gly Lys Asn Pro Asp Glu Leu Ala Tyr Leu Ala Gly Asp Gln Lys
1               5                   10                  15

Arg Tyr Ser Thr Lys Arg Ala Ser Ser Ser Trp Ser Thr
            20                  25

<210> SEQ ID NO 14
<211> LENGTH: 27
<212> TYPE: PRT
<213> ORGANISM: Neisseria

<400> SEQUENCE: 14

Phe Ala Val Asp Tyr Thr Arg Tyr Lys Asn Tyr Lys Ala Pro Ser Thr
1               5                   10                  15

Asp Phe Lys Leu Tyr Ser Ile Gly Ala Ser Ala
            20                  25

<210> SEQ ID NO 15
<211> LENGTH: 28
<212> TYPE: PRT
<213> ORGANISM: Neisseria

<400> SEQUENCE: 15

Ala Arg Leu Ser Leu Asn Arg Ala Ser Val Asp Leu Gly Gly Ser Asp
1               5                   10                  15

Ser Phe Ser Gln Thr Ser Ile Gly Leu Gly Val Leu
            20                  25

<210> SEQ ID NO 16
<211> LENGTH: 9
<212> TYPE: PRT
<213> ORGANISM: N. meningitidis
<220> FEATURE:
<221> NAME/KEY: VARIANT
<222> LOCATION: 2, 5, 9
<223> OTHER INFORMATION: Xaa = Any Amino Acid

<400> SEQUENCE: 16

Leu Xaa Gly Gly Xaa Gly Asn Asp Xaa
1               5
```

```
<210> SEQ ID NO 17
<211> LENGTH: 10
<212> TYPE: PRT
<213> ORGANISM: Artificial Sequence
<220> FEATURE:
<223> OTHER INFORMATION: SAEP2 peptide

<400> SEQUENCE: 17

Lys Thr Lys Cys Lys Phe Leu Lys Lys Cys
 1               5                  10

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
atgcctgcaa ccttcaagtg                                           20

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
atgtcgacaa tcgcccctca agtcggtttg                                30

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
atgtcgacta cctgcggccg gattatgc                                  28

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
atgacgtctc agggtcgttt gttgcgtccg gc                             32

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
agcgtcgact tcagacggcc acgttgtgtc                                30

<210> SEQ ID NO 23
<211> LENGTH: 27
<212> TYPE: DNA
<213> ORGANISM: Artificial Sequence
<220> FEATURE:
```

```
<223> OTHER INFORMATION: Primer

<400> SEQUENCE: 23
agcgtcgacg ctgaggtctg cctcgtg                                       27

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
atcatatggc tcgtttattt tcactcaaac c                                  31

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
tgcatatgga tgccgttgcg gcggag                                        26

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
tgggatcctc agggtcgttt gttgcgtcc                                     29

<210> SEQ ID NO 27
<211> LENGTH: 802
<212> TYPE: PRT
<213> ORGANISM: N. meningitidis

<400> SEQUENCE: 27
```

Leu Ala Arg Leu Phe Ser Leu Lys Pro Leu Val Leu Ala Leu Gly Phe
1               5                   10                  15

Cys Phe Gly Thr His Cys Ala Ala Ala Asp Ala Val Ala Ala Glu Glu
                20                  25                  30

Thr Asp Asn Pro Thr Ala Gly Gly Ser Val Arg Ser Val Ser Glu Pro
            35                  40                  45

Ile Gln Pro Thr Ser Leu Ser Leu Gly Ser Thr Cys Leu Phe Cys Ser
        50                  55                  60

Asn Glu Ser Gly Ser Pro Glu Arg Thr Glu Ala Ala Val Arg Gly Ser
65                  70                  75                  80

Gly Glu Ala Ser Ile Pro Glu Asp Tyr Thr Arg Ile Val Ala Asp Lys
                85                  90                  95

Val Glu Gly Gln Ser Gln Val Gln Val Arg Ala Glu Gly Asn Val Val
            100                 105                 110

Val Glu Arg Asn Arg Thr Thr Leu Asn Thr Asp Trp Ala Asp Tyr Asp
        115                 120                 125

Gln Ser Gly Asp Thr Val Thr Ala Gly Asp Arg Phe Ala Leu Gln Gln
    130                 135                 140

Asp Gly Thr Leu Ile Arg Gly Glu Thr Leu Thr Tyr Asn Leu Glu Gln
145                 150                 155                 160

-continued

```
Gln Thr Gly Glu Ala His Asn Val Arg Met Glu Thr His Gly Gly
            165                 170                 175

Arg Arg Leu Gln Ser Val Ser Arg Thr Ala Glu Met Leu Gly Glu Gly
            180                 185                 190

His Tyr Lys Leu Thr Glu Thr Gln Phe Asn Thr Cys Ser Ala Gly Asp
            195                 200                 205

Ala Gly Trp Tyr Val Lys Ala Ala Ser Val Glu Ala Asp Arg Glu Lys
        210                 215                 220

Gly Ile Gly Val Ala Lys His Ala Ala Phe Val Phe Gly Val Pro
225                 230                 235                 240

Ile Phe Tyr Thr Pro Trp Ala Asp Phe Pro Leu Asp Gly Asn Arg Lys
            245                 250                 255

Ser Gly Leu Leu Val Pro Ser Leu Ser Ala Gly Ser Asp Gly Val Ser
            260                 265                 270

Leu Ser Val Pro Tyr Tyr Phe Asn Leu Ala Pro Asn Leu Asp Ala Thr
            275                 280                 285

Phe Ala Pro Ser Val Ile Gly Glu Arg Gly Ala Val Phe Asp Gly Gln
            290                 295                 300

Val Arg Tyr Leu Arg Pro Asp Tyr Ala Gly Gln Ser Asp Leu Thr Trp
305                 310                 315                 320

Leu Pro His Asp Lys Lys Ser Gly Arg Asn Asn Arg Tyr Gln Ala Lys
            325                 330                 335

Trp Gln His Arg His Asp Ile Ser Asp Thr Leu Gln Ala Gly Val Asp
            340                 345                 350

Phe Asn Gln Val Ser Asp Ser Gly Tyr Tyr Arg Asp Phe Tyr Gly Asn
            355                 360                 365

Lys Glu Ile Ala Gly Asn Val Asn Leu Asn Arg Arg Val Trp Leu Asp
        370                 375                 380

Tyr Gly Gly Arg Ala Ala Gly Gly Ser Leu Asn Ala Gly Leu Ser Val
385                 390                 395                 400

Leu Lys Tyr Gln Thr Leu Ala Asn Gln Ser Gly Tyr Lys Asp Lys Pro
            405                 410                 415

Tyr Ala Leu Met Pro Arg Leu Ser Ala Asp Trp Arg Lys Asn Thr Gly
            420                 425                 430

Arg Ala Gln Ile Gly Val Ser Ala Gln Phe Thr Arg Phe Ser His Asp
            435                 440                 445

Ser Arg Gln Asp Gly Ser Arg Leu Val Val Tyr Pro Asp Ile Lys Trp
            450                 455                 460

Asp Phe Ser Asn Ser Trp Gly Tyr Val Arg Pro Lys Leu Gly Leu His
465                 470                 475                 480

Ala Thr Tyr Tyr Ser Leu Asn Arg Phe Gly Ser Gln Glu Ala Arg Arg
            485                 490                 495

Val Ser Arg Thr Leu Pro Ile Val Asn Ile Asp Ser Gly Ala Thr Phe
            500                 505                 510

Glu Arg Asn Thr Arg Met Phe Gly Gly Val Leu Gln Thr Leu Glu
            515                 520                 525

Pro Arg Leu Phe Tyr Asn Tyr Ile Pro Ala Lys Ser Gln Asn Asp Leu
            530                 535                 540

Pro Asn Phe Asp Ser Ser Glu Ser Ser Phe Gly Tyr Gly Gln Leu Phe
545                 550                 555                 560

Arg Glu Asn Leu Tyr Tyr Gly Asn Asp Arg Ile Asn Thr Ala Asn Ser
            565                 570                 575

Leu Ser Ala Ala Val Gln Ser Arg Ile Leu Asp Gly Ala Thr Gly Glu
            580                 585                 590
```

```
Glu Arg Phe Arg Ala Gly Ile Gly Gln Lys Phe Tyr Phe Lys Asp Asp
        595                 600                 605

Ala Val Met Leu Asp Gly Ser Val Gly Lys Lys Pro Arg Asn Arg Ser
    610                 615                 620

Asp Trp Val Ala Phe Ala Ser Gly Ser Ile Gly Ser Arg Phe Ile Leu
625                 630                 635                 640

Asp Ser Ser Ile His Tyr Asn Gln Asn Asp Lys Arg Ala Glu Asn Tyr
                645                 650                 655

Ala Val Gly Ala Ser Tyr Arg Pro Ala Gln Gly Lys Val Leu Asn Ala
            660                 665                 670

Arg Tyr Lys Tyr Gly Arg Asn Glu Lys Ile Tyr Leu Lys Ser Asp Gly
        675                 680                 685

Ser Tyr Phe Tyr Asp Lys Leu Ser Gln Leu Asp Leu Ser Ala Gln Trp
    690                 695                 700

Pro Leu Thr Arg Asn Leu Ser Ala Val Val Arg Tyr Asn Tyr Gly Phe
705                 710                 715                 720

Glu Ala Lys Lys Pro Ile Glu Met Leu Ala Gly Ala Glu Tyr Lys Ser
                725                 730                 735

Ser Cys Gly Cys Trp Gly Ala Gly Val Tyr Ala Gln Arg Tyr Val Thr
            740                 745                 750

Gly Glu Asn Thr Tyr Lys Asn Ala Val Phe Phe Ser Leu Gln Leu Lys
        755                 760                 765

Asp Leu Ser Ser Val Gly Arg Asn Pro Ala Asp Arg Met Asp Val Ala
    770                 775                 780

Val Pro Gly Tyr Ile Pro Ala His Ser Leu Ser Ala Gly Arg Asn Lys
785                 790                 795                 800

Arg Pro

<210> SEQ ID NO 28
<211> LENGTH: 802
<212> TYPE: PRT
<213> ORGANISM: N. meningitidis

<400> SEQUENCE: 28

Leu Ala Arg Leu Phe Ser Leu Lys Pro Leu Val Leu Ala Leu Gly Leu
1               5                   10                  15

Cys Phe Gly Thr His Cys Ala Ala Asp Ala Val Ala Ala Glu Glu
                20                  25                  30

Thr Asp Asn Pro Thr Ala Gly Glu Ser Val Arg Ser Val Ser Glu Pro
            35                  40                  45

Ile Gln Pro Thr Ser Leu Ser Leu Gly Ser Thr Cys Leu Phe Cys Ser
    50                  55                  60

Asn Glu Ser Gly Ser Pro Glu Arg Thr Glu Ala Ala Val Gln Gly Ser
65                  70                  75                  80

Gly Glu Ala Ser Ile Pro Glu Asp Tyr Thr Arg Ile Val Ala Asp Arg
                85                  90                  95

Met Glu Gly Gln Ser Gln Val Gln Val Arg Ala Glu Gly Asn Val Val
            100                 105                 110

Val Glu Arg Asn Arg Thr Thr Leu Asn Thr Asp Trp Ala Asp Tyr Asp
        115                 120                 125

Gln Ser Gly Asp Thr Val Thr Ala Gly Asp Arg Phe Ala Leu Gln Gln
    130                 135                 140

Asp Gly Thr Leu Ile Arg Gly Glu Thr Leu Thr Tyr Asn Leu Glu Gln
145                 150                 155                 160
```

-continued

```
Gln Thr Gly Glu Ala His Asn Val Arg Met Glu Ile Glu Gln Gly Gly
                165                 170                 175
Arg Arg Leu Gln Ser Val Ser Arg Thr Ala Glu Met Leu Gly Glu Gly
            180                 185                 190
His Tyr Lys Leu Thr Glu Thr Gln Phe Asn Thr Cys Ser Ala Gly Asp
        195                 200                 205
Ala Gly Trp Tyr Val Lys Ala Ala Ser Val Glu Ala Asp Arg Glu Lys
    210                 215                 220
Gly Ile Gly Val Ala Lys His Ala Ala Phe Val Phe Gly Gly Val Pro
225                 230                 235                 240
Ile Phe Tyr Thr Pro Trp Ala Asp Phe Pro Leu Asp Gly Asn Arg Lys
                245                 250                 255
Ser Gly Leu Leu Val Pro Ser Leu Ser Ala Gly Ser Asp Gly Val Ser
            260                 265                 270
Leu Ser Val Pro Tyr Tyr Phe Asn Leu Ala Pro Asn Leu Asp Ala Thr
        275                 280                 285
Phe Ala Pro Ser Val Ile Gly Glu Arg Gly Ala Val Phe Asp Gly Gln
    290                 295                 300
Val Arg Tyr Leu Arg Pro Asp Tyr Ala Gly Gln Ser Asp Leu Thr Trp
305                 310                 315                 320
Leu Pro His Asp Lys Lys Ser Gly Arg Asn Asn Arg Tyr Gln Ala Lys
                325                 330                 335
Trp Gln His Arg His Asp Ile Ser Asp Thr Leu Gln Ala Gly Val Asp
            340                 345                 350
Phe Asn Gln Val Ser Asp Ser Gly Tyr Tyr Arg Asp Phe Tyr Gly Asn
        355                 360                 365
Lys Glu Ile Ala Gly Asn Val Asn Leu Asn Arg Arg Val Trp Leu Asp
    370                 375                 380
Tyr Gly Gly Arg Ala Ala Gly Gly Ser Leu Asn Ala Gly Leu Ser Val
385                 390                 395                 400
Leu Lys Tyr Gln Thr Leu Ala Asn Gln Ser Gly Tyr Lys Asp Lys Pro
                405                 410                 415
Tyr Ala Leu Met Pro Arg Leu Ser Val Glu Trp Arg Lys Asn Thr Gly
            420                 425                 430
Arg Ala Gln Ile Gly Val Ser Ala Gln Phe Thr Arg Phe Ser His Asp
        435                 440                 445
Ser Arg Gln Asp Gly Ser Arg Leu Val Val Tyr Pro Asp Ile Lys Trp
    450                 455                 460
Asp Phe Ser Asn Ser Trp Gly Tyr Val Arg Pro Lys Leu Gly Leu His
465                 470                 475                 480
Ala Thr Tyr Tyr Ser Leu Asn Arg Phe Gly Ser Gln Glu Ala Arg Arg
                485                 490                 495
Val Ser Arg Thr Leu Pro Ile Val Asn Ile Asp Ser Gly Ala Thr Phe
            500                 505                 510
Glu Arg Asn Thr Arg Met Phe Gly Gly Glu Val Leu Gln Thr Leu Glu
        515                 520                 525
Pro Arg Leu Phe Tyr Asn Tyr Ile Pro Ala Lys Ser Gln Asn Asp Leu
    530                 535                 540
Pro Asn Phe Asp Ser Ser Glu Ser Ser Phe Gly Tyr Gly Gln Leu Phe
545                 550                 555                 560
Arg Glu Asn Leu Tyr Tyr Gly Asn Asp Arg Ile Asn Thr Ala Asn Ser
                565                 570                 575
Leu Ser Ala Ala Val Gln Ser Arg Ile Leu Asp Gly Ala Thr Gly Glu
            580                 585                 590
```

```
Glu Arg Phe Arg Ala Gly Ile Gly Gln Lys Phe Tyr Phe Lys Asp Asp
            595                 600                 605

Ala Val Met Leu Asp Gly Ser Val Gly Lys Lys Pro Arg Asn Arg Ser
            610                 615                 620

Asp Trp Val Ala Phe Ala Ser Gly Ser Ile Gly Ser Arg Phe Ile Leu
625                 630                 635                 640

Asp Ser Ser Ile His Tyr Asn Gln Asn Asp Lys Arg Ala Glu Asn Tyr
                645                 650                 655

Ala Val Gly Ala Ser Tyr Arg Pro Ala Gln Gly Lys Val Leu Asn Ala
            660                 665                 670

Arg Tyr Lys Tyr Gly Arg Asn Glu Lys Ile Tyr Leu Lys Ser Asp Gly
            675                 680                 685

Ser Tyr Phe Tyr Asp Lys Leu Ser Gln Leu Asp Leu Ser Ala Gln Trp
            690                 695                 700

Pro Leu Thr Arg Asn Leu Ser Ala Val Val Arg Tyr Asn Tyr Gly Phe
705                 710                 715                 720

Glu Ala Lys Lys Pro Ile Glu Val Leu Ala Gly Ala Glu Tyr Lys Ser
                725                 730                 735

Ser Cys Gly Cys Trp Gly Ala Gly Val Tyr Ala Gln Arg Tyr Val Thr
            740                 745                 750

Gly Glu Asn Thr Tyr Lys Asn Ala Val Phe Phe Ser Leu Gln Leu Lys
            755                 760                 765

Asp Leu Ser Ser Val Gly Arg Asn Pro Ala Asp Arg Met Asp Val Ala
            770                 775                 780

Val Pro Gly Tyr Ile Thr Ala His Ser Leu Ser Ala Gly Arg Asn Lys
785                 790                 795                 800

Arg Pro

<210> SEQ ID NO 29
<211> LENGTH: 802
<212> TYPE: PRT
<213> ORGANISM: N. meningitidis

<400> SEQUENCE: 29

Met Ala Arg Leu Phe Ser Leu Lys Pro Leu Val Leu Ala Leu Gly Phe
1               5                   10                  15

Cys Phe Gly Thr His Cys Ala Ala Asp Ala Val Ala Ala Glu Glu
            20                  25                  30

Thr Asp Asn Pro Thr Ala Gly Gly Ser Val Arg Ser Val Ser Glu Pro
            35                  40                  45

Ile Gln Pro Thr Ser Leu Ser Leu Gly Ser Thr Cys Leu Phe Cys Ser
50                  55                  60

Asn Glu Ser Gly Ser Pro Glu Arg Thr Glu Ala Ala Val Gln Gly Ser
65                  70                  75                  80

Gly Glu Ala Ser Ile Pro Glu Asp Tyr Thr Arg Ile Val Ala Asp Arg
                85                  90                  95

Met Glu Gly Gln Ser Gln Val Gln Val Arg Ala Glu Gly Asn Val Val
            100                 105                 110

Val Glu Arg Asn Arg Thr Thr Leu Asn Ala Asp Trp Ala Asp Tyr Asp
            115                 120                 125

Gln Ser Gly Asp Thr Val Thr Ala Gly Asp Arg Phe Ala Leu Gln Gln
130                 135                 140

Asp Gly Thr Leu Ile Arg Gly Glu Thr Leu Thr Tyr Asn Leu Glu Gln
145                 150                 155                 160
```

-continued

```
Gln Thr Gly Glu Ala His Asn Val Arg Met Glu Thr His Gly Gly
            165                 170                 175

Arg Arg Leu Gln Ser Val Ser Arg Thr Ala Glu Met Leu Gly Glu Gly
            180                 185                 190

His Tyr Lys Leu Thr Glu Thr Gln Phe Asn Thr Cys Ser Ala Gly Asp
            195                 200                 205

Ala Gly Trp Tyr Val Lys Ala Ala Ser Val Glu Ala Asp Arg Glu Lys
        210                 215                 220

Gly Ile Gly Val Ala Lys His Ala Ala Phe Val Phe Gly Gly Val Pro
225                 230                 235                 240

Ile Phe Tyr Thr Pro Trp Ala Asp Phe Pro Leu Asp Gly Asn Arg Lys
            245                 250                 255

Ser Gly Leu Leu Val Pro Ser Leu Ser Ala Gly Ser Asp Gly Val Ser
            260                 265                 270

Leu Ser Val Pro Tyr Tyr Phe Asn Leu Ala Pro Asn Leu Asp Ala Thr
            275                 280                 285

Phe Ala Pro Gly Val Ile Gly Glu Arg Gly Ala Val Phe Asp Gly Gln
            290                 295                 300

Val Arg Tyr Leu Arg Pro Asp Tyr Ala Gly Gln Ser Asp Leu Thr Trp
305                 310                 315                 320

Leu Pro His Asp Lys Lys Ser Gly Arg Asn Asn Arg Tyr Gln Ala Lys
            325                 330                 335

Trp Gln His Arg His Asp Ile Ser Asp Thr Leu Gln Ala Gly Val Asp
            340                 345                 350

Phe Asn Gln Val Ser Asp Ser Gly Tyr Tyr Arg Asp Phe Tyr Gly Asn
            355                 360                 365

Lys Glu Ile Ala Gly Asn Val Asn Leu Asn Arg Arg Val Trp Leu Asp
370                 375                 380

Tyr Gly Gly Arg Ala Ala Gly Gly Ser Leu Asn Ala Gly Leu Ser Val
385                 390                 395                 400

Leu Lys Tyr Gln Thr Leu Ala Asn Gln Ser Gly Tyr Lys Asp Lys Pro
            405                 410                 415

Tyr Ala Leu Met Pro Arg Leu Ser Ala Asp Trp Arg Lys Asn Thr Gly
            420                 425                 430

Arg Ala Gln Ile Gly Val Ser Ala Gln Phe Thr Arg Phe Ser His Asp
            435                 440                 445

Ser Arg Gln Asp Gly Ser Arg Leu Val Val Tyr Pro Asp Ile Lys Trp
450                 455                 460

Asp Phe Ser Asn Ser Trp Gly Tyr Val Arg Pro Lys Leu Gly Leu His
465                 470                 475                 480

Ala Thr Tyr Tyr Ser Leu Asn Arg Phe Gly Ser Gln Glu Ala Arg Arg
            485                 490                 495

Val Ser Arg Thr Leu Pro Ile Val Asn Ile Asp Ser Gly Met Thr Phe
            500                 505                 510

Glu Arg Asn Thr Arg Met Phe Gly Gly Val Leu Gln Thr Leu Glu
            515                 520                 525

Pro Arg Leu Phe Tyr Asn Tyr Ile Pro Ala Lys Ser Gln Asn Asp Leu
            530                 535                 540

Pro Asn Phe Asp Ser Ser Glu Ser Ser Phe Gly Tyr Gly Leu Phe
545                 550                 555                 560

Arg Glu Asn Leu Tyr Tyr Gly Asn Asp Arg Ile Asn Thr Ala Asn Ser
            565                 570                 575

Leu Ser Ala Ala Val Gln Ser Arg Ile Leu Asp Gly Ala Thr Gly Glu
            580                 585                 590
```

```
Glu Arg Phe Arg Ala Gly Ile Gly Gln Lys Phe Tyr Phe Lys Asn Asp
            595                 600                 605

Ala Val Met Leu Asp Gly Ser Val Gly Lys Lys Pro Arg Ser Arg Ser
            610                 615                 620

Asp Trp Val Ala Phe Ala Ser Ser Gly Ile Gly Ser Arg Phe Ile Leu
625                 630                 635                 640

Asp Ser Ser Ile His Tyr Asn Gln Asn Asp Lys Arg Ala Glu Asn Tyr
                645                 650                 655

Ala Val Gly Ala Ser Tyr Arg Pro Ala Gln Gly Lys Val Leu Asn Ala
            660                 665                 670

Arg Tyr Lys Tyr Gly Arg Asn Glu Lys Ile Tyr Leu Lys Ser Asp Gly
            675                 680                 685

Ser Tyr Phe Tyr Asp Lys Leu Ser Gln Leu Asp Leu Ser Ala Gln Trp
            690                 695                 700

Pro Leu Thr Arg Asn Leu Ser Ala Val Val Arg Tyr Asn Tyr Gly Phe
705                 710                 715                 720

Glu Ala Lys Lys Pro Ile Glu Val Leu Ala Gly Ala Glu Tyr Lys Ser
                725                 730                 735

Ser Cys Gly Cys Trp Gly Ala Gly Val Tyr Ala Gln Arg Tyr Val Thr
            740                 745                 750

Gly Glu Asn Thr Tyr Lys Asn Ala Val Phe Phe Ser Leu Gln Leu Lys
            755                 760                 765

Asp Leu Ser Ser Val Gly Arg Asn Pro Ala Asp Arg Met Asp Val Ala
            770                 775                 780

Val Pro Gly Tyr Ile Pro Ala His Ser Leu Ser Ala Gly Arg Asn Lys
785                 790                 795                 800

Arg Pro

<210> SEQ ID NO 30
<211> LENGTH: 9
<212> TYPE: PRT
<213> ORGANISM: N. meningitidis
<220> FEATURE:
<221> NAME/KEY: VARIANT
<222> LOCATION: 2, 5, 9
<223> OTHER INFORMATION: Xaa = Any Amino Acid

<400> SEQUENCE: 30

Leu Xaa Gly Gly Xaa Gly Asp Asp Xaa
 1               5
```